US007276364B1

(12) United States Patent
Madison et al.

(10) Patent No.: US 7,276,364 B1
(45) Date of Patent: Oct. 2, 2007

(54) NUCLEIC ACIDS ENCODING ENDOTHELIASES, ENDOTHELIASES AND USES THEREOF

(75) Inventors: Edwin L. Madison, San Diego, CA (US); Edgar O. Ong, San Diego, CA (US)

(73) Assignee: Dendreon Corporation, Seattle, WA (US)

( * ) Notice: Subject to any disclaimer, the term of this patent is extended or adjusted under 35 U.S.C. 154(b) by 0 days.

(21) Appl. No.: 09/717,473

(22) Filed: Nov. 20, 2000

Related U.S. Application Data

(63) Continuation of application No. PCT/US00/31803, filed on Nov. 17, 2000.

(60) Provisional application No. 60/234,840, filed on Sep. 22, 2000.

(51) Int. Cl.
*C12N 9/50* (2006.01)
*C12N 9/00* (2006.01)
*C07H 21/04* (2006.01)

(52) U.S. Cl. .............................. 435/219; 435/4; 435/6; 435/69.1; 435/183; 536/23.2

(58) Field of Classification Search ................ 435/183, 435/188, 195, 212, 213, 217, 218, 219, 226, 435/4, 6, 23.24, 69.1, 252.3, 320.1, 200, 435/440; 530/412, 419, 421, 810, 812, 815, 530/816, 827, 23.2, 23.5, 23.7
See application file for complete search history.

(56) References Cited

U.S. PATENT DOCUMENTS

| | | | |
|---|---|---|---|
| 3,536,809 A | 10/1970 | Applezweig | 424/28 |
| 3,598,123 A | 8/1971 | Zaffaroni | 128/268 |
| 3,630,200 A | 12/1971 | Higuchi | 128/260 |
| 3,843,443 A | 10/1974 | Fishman | 195/63 |
| 3,846,770 A | 11/1974 | Theeuwes et al. | 128/260 |
| 3,916,899 A | 11/1975 | Theeuwes et al. | 128/260 |
| 3,940,475 A | 2/1976 | Gross | 424/1 |
| 4,006,117 A | 2/1977 | Merrifield et al. | 260/45.9 NP |
| 4,008,719 A | 2/1977 | Theeuwes et al. | 128/260 |
| 4,179,337 A | 12/1979 | Davis et al. | 435/181 |
| 4,301,144 A | 11/1981 | Iwashita et al. | 424/78 |
| 4,496,689 A | 1/1985 | Mitra | 525/54.1 |
| 4,507,230 A | 3/1985 | Tam et al. | 260/112.5 R |
| 4,522,811 A | 6/1985 | Eppstein et al. | 514/2 |
| 4,640,835 A | 2/1987 | Shimizu et al. | 424/94 |
| 4,670,417 A | 6/1987 | Iwasaki et al. | 514/6 |
| 4,687,610 A | 8/1987 | Vassilatos | 264/211.14 |
| 4,769,027 A | 9/1988 | Baker et al. | 424/493 |
| 4,791,192 A | 12/1988 | Nakagawa et al. | 530/399 |
| 4,908,405 A | 3/1990 | Bayer et al. | 525/61 |
| 4,946,778 A | 8/1990 | Ladner et al. | 435/69.8 |
| 4,952,496 A | 8/1990 | Studier et al. | 435/91 |
| 4,980,286 A | 12/1990 | Morgan et al. | 435/172.3 |
| 5,059,595 A | 10/1991 | Le Grazie | 424/468 |
| 5,073,543 A | 12/1991 | Marshall et al. | 514/21 |
| 5,120,548 A | 6/1992 | McClelland et al. | 424/473 |
| 5,215,899 A | 6/1993 | Dattagupta | 435/6 |
| 5,225,539 A | 7/1993 | Winter | 530/387.3 |
| 5,270,170 A | 12/1993 | Schatz et al. | 435/7.37 |
| 5,292,814 A | 3/1994 | Bayer et al. | 525/243 |
| 5,346,823 A | 9/1994 | Estell et al. | 435/222 |
| 5,354,566 A | 10/1994 | Addesso et al. | 426/9 |
| 5,389,449 A | 2/1995 | Afeyan et al. | 428/523 |
| 5,436,128 A | 7/1995 | Harpold et al. | 435/6 |
| 5,482,848 A | 1/1996 | Dickson et al. | 435/219 |
| 5,589,154 A | 12/1996 | Anderson | 424/1.41 |
| 5,591,767 A | 1/1997 | Mohr et al. | 514/413 |
| 5,593,990 A | 1/1997 | D'Amato | 514/235.2 |
| 5,612,474 A | 3/1997 | Patel | 536/27.14 |
| 5,629,327 A | 5/1997 | D'Amato | 514/323 |
| 5,639,476 A | 6/1997 | Oshlack et al. | 424/468 |
| 5,674,533 A | 10/1997 | Santus et al. | 424/493 |
| 5,712,291 A | 1/1998 | D'Amato | 514/323 |
| 5,733,566 A | 3/1998 | Lewis | 424/426 |
| 5,792,616 A | 8/1998 | Persico et al. | 435/7.21 |
| 5,804,410 A * | 9/1998 | Yamaoka et al. | |
| 5,902,723 A | 5/1999 | Dower et al. | 435/6 |
| 5,925,525 A | 7/1999 | Fodor et al. | 435/6 |
| 5,972,616 A * | 10/1999 | O'Brien et al. | |
| 6,121,238 A | 9/2000 | Dower et al. | 514/13 |
| 6,294,663 B1 | 9/2001 | O'Brien et al. | 536/23.5 |
| 37,857 A1 | 3/2002 | Semple et al. | 514/19 |
| 6,365,391 B1 | 4/2002 | Webster et al. | 435/183 |

(Continued)

FOREIGN PATENT DOCUMENTS

| | | |
|---|---|---|
| AU | 200010689 | 9/2000 |
| EP | 0257352 | 3/1988 |
| EP | 0613683 A1 | 9/1994 |
| EP | 0613683 B1 | 9/1994 |
| WO | 8809810 | 12/1988 |
| WO | 8910134 | 11/1989 |
| WO | 9011364 | 10/1990 |
| WO | 9206180 | 4/1992 |
| WO | 9220316 | 11/1992 |

(Continued)

OTHER PUBLICATIONS

Yamaoka et al. J. Biol. Chem., 1998, vol. 273:11895-11901.*

(Continued)

*Primary Examiner*—Manjunath Rao
(74) *Attorney, Agent, or Firm*—Stephanie Seidman; Frank J. Miskiel; Fish & Richardson P.C.

(57) ABSTRACT

Provided herein are endotheliases and portions, particularly, the protease domains, and nucleic acids that encode the endotheliases. The endotheliases are transmembrane proteases expressed in endothelial cells. The nucleic acids and encoded proteins and protease domain portions thereof are used in a variety of prognostic, diagnostic, therapeutic and screening methods, including methods for screening for compounds that modulate angiogenesis.

32 Claims, 1 Drawing Sheet

U.S. PATENT DOCUMENTS

| | | | |
|---|---|---|---|
| 107,266 A1 | 8/2002 | Lim-Wilby et al. | 514/339 |
| 160,962 A1 | 10/2002 | Saksena et al. | 514/19 |
| 8,372 A1 | 1/2003 | Madison et al. | 435/226 |
| 2002/0019006 A1 | 2/2002 | Yuan et al. | 435/6 |
| 2002/0064856 A1* | 5/2002 | Plowman et al. | 435/226 |
| 2002/0119130 A1* | 8/2002 | Eaton et al. | 435/226 |
| 2003/0073129 A1* | 4/2003 | Baker et al. | 435/7.1 |
| 2003/0175938 A1* | 9/2003 | Shi et al. | 435/226 |
| 2003/0232349 A1* | 12/2003 | Delegeane et al. | 435/6 |

FOREIGN PATENT DOCUMENTS

| | | | |
|---|---|---|---|
| WO | 9222635 | | 12/1992 |
| WO | 9314188 | | 7/1993 |
| WO | 9320221 | | 10/1993 |
| WO | 9325221 | | 12/1993 |
| WO | 9408598 | | 4/1994 |
| WO | 9417784 | | 8/1994 |
| WO | 9511755 | | 5/1995 |
| WO | 9523222 | | 8/1995 |
| WO | 9534326 | | 12/1995 |
| WO | 8603840 | | 7/1996 |
| WO | 9630353 | | 10/1996 |
| WO | 9721690 | | 6/1997 |
| WO | 9917790 | | 4/1999 |
| WO | 9936550 | | 7/1999 |
| WO | 9942120 | | 8/1999 |
| WO | 9946281 | | 9/1999 |
| WO | 0012708 | | 3/2000 |
| WO | 0050061 | | 8/2000 |
| WO | 0052044 | | 9/2000 |
| WO | 0053232 | | 9/2000 |
| WO | 0053756 | | 9/2000 |
| WO | 0055124 | | 9/2000 |
| WO | 0068247 | | 11/2000 |
| WO | 0078961 | A1 | 12/2000 |
| WO | 0104141 | A2 | 1/2001 |
| WO | 0127624 | A2 | 4/2001 |
| WO | 0136351 | | 5/2001 |
| WO | 0136604 | | 5/2001 |
| WO | 0136645 | | 5/2001 |
| WO | 0146407 | | 6/2001 |
| WO | 0149864 | | 7/2001 |
| WO | 0154477 | | 8/2001 |
| WO | 0155441 | A2 | 8/2001 |
| WO | 0157194 | | 8/2001 |
| WO | 0168848 | | 9/2001 |
| WO | 0175067 | A2 | 10/2001 |
| WO | 0200860 | | 1/2002 |
| WO | 0206453 | A2 | 1/2002 |
| WO | 0208251 | | 1/2002 |
| WO | 02008187 | | 1/2002 |
| WO | 02095007 | | 2/2002 |
| WO | 0220475 | | 3/2002 |
| WO | 0226947 | A2 | 4/2002 |
| WO | 02048097 | | 6/2002 |
| WO | 02072786 | | 9/2002 |
| WO | 02077263 | | 10/2002 |
| WO | 02077267 | | 10/2002 |
| WO | 02092841 | | 11/2002 |
| WO | 03004681 | | 1/2003 |

OTHER PUBLICATIONS

Sequence alignment for Shi et al.*
Sequence alignment for Baker et al.*
Sequence alignment for Eaton et al.*
Sequence alignment for Xiao et al. (DNA).*
Sequence alignment for Xiao et al. (polypeptide).*
Sequence alignment for Ni et al.*
Derwent#007409639, WPI Acc. No. 1988-043574/198807, for European Patent Application, EP 257352, "Determining free portion of e.g. thyroxine in presence of binder—by reaction with antibody which does not effect bound-unbound equilibrium, then reacting cross reactive tracer with antibody".

Harris et al., "Rapid and general profiling of protease specificity by using combinatorial flurogenic substrate libraries," *PNAS* 97: 7754-7759 (2000).

Liu et al., "Eradication of large colon tumor xenografts by targeted delivery of maytansinoids", *Proc Natl Acad Sci USA*, 93:8618-8623 (1996).

Pastan et al., "Recombinant Toxins for Cancer Treatment", *Science*, 254:1173-1177; (1991).

Schmidt, M. and W. Wels, "Targeted inhibition of tumour cell growth by a bispecific single-chian toxin containing an antibody domain and TGFα", *British Journal of Cancer*, 74:853-862 (1996).

Abraham et al., "Immunochemical Identification of the Serine Protease Inhibitor $α_1$-Antichymotrypsin in the Brain Amyloid Deposits of Alzheimer's Disease", *Cell*, 52:487-501; (1988).

Alam et al., "Reporter Genes: Application to the Study of Mammalian Gene Transcription", *Anal. Biochem.*, 188:245-254; (1990).

Alonso et al., "Effects of synthetic urokinase inhibitors on local invasion and metastasis in a murine mammary tumor model", *Breast Cancer Res. Treat.*, 40:209-223; (1996).

Appel et al., "The *Drosophila* Stubble-stubbloid gene encodes an apparent transmembrane serine protease required for epithelial morphogenesis", *Proc. Natl. Acad. Sci. U.S.A.*, 90:4937-4941; (1993).

Avery et al., "Systemic Amiloride Inhibits Experimentally Induced Neovascularization", *Arch. Ophthalmol.*, 108:1474-1476; (1990).

Bains et al., "Effects of LEX032, a novel recombinant serine protease inhibitor, on $N^G$-nitro-L-arginine methyl ester induced leukocyte-endothelial cell", *Eur. J. Pharmacol.*, 356:67-72; (1998).

Baker et al., "A Scintillation Proximity Assay for UDP-GalNAc:Polypeptide, N-Acetylgalactosaminyltransferase", *Anal. Biochem.*, 239:20-24; (1996).

Batra et al., "Insertion of Constant Region Domains of Human $IgG_1$ Into CD4-PE40 Increases Its Plasma Half-life", *Molecular Immunol.*, 30(4):379-386; (1993).

Baum et al., "Development of a Scintillation Proximity Assay for Human Cytomegalovirus Protease Using $^{33}$Phosphorous", *Anal. Biochem.*, 237:129-134; (1996).

Beck et al., "Identification of Efficiently Cleaved Substrates for HIV-1 Protease Using a Phage Display Library and Use in Inhibitor Development", *Virology*, 274(2):391-401; (2000).

Berger et al., "Structure of the mouse gene for the serine protease inhibitor neuroserpin (P/12)", *Gene*, 214:25-33; (1998).

Benoist et al., "In vivo sequence requirements of the SV40 early promoter region", *Nature*, 290:304-310; (1981).

Billström et al., "The Urokinase Inhibitor p-Aminobenzamidine Inhibits Growth of a Human Prostate Tumor in SCID Mice", *Int. J. Cancer*, 61:542-547; (1995).

Blanton et al., "Characterization of a native and recombinant *Schistosoma haematobium* serine protease inhibitor gene product", *Mol. Biochem. Parasitol.*, 63:1-11; (1994).

Boesen et al., "Circumvention of chemotherapy-induced myelosuppression by transfer of the *mdr1* gene", 6:291-302; (1994).

Bourinbaiar et al., "Effect of Serine Protease Inhibitor, N-α-Tosyl-L-lysyl-Chloromethyl Ketone (TLCK), on Cell-Mediated and Cell-Free HIV-1 Spread", *Cell. Immuno.*, 155:230-236; (1994).

Bout et al., "Lung Gene Therapy: In Vivo Adenovirus-Mediated Gene Transfer to Rhesus Monkey Airway Epithelium", *Human Gene Therapy*, 5:3-10; (1994).

Braunwalder et al., "Application of Scintillating Microtiter Plates to Measure Phosphopeptide Interactions with the GRB2-SH2 Binding Domain", *J. Biomol. Screening*, 1(1):23-26; (1996).

Brinster et al., "Regulation of metallothionein-thymidine kinase fusion plasmids injected into mouse eggs", *Nature*, 296:39-42; (1982).

Brooks et al., "Use of the 10-Day-Old Chick embryo Model for Studying Angiogenesis", *Methods in Molecular Biology*, 129:257-269; (1999).

Capecchi et al., "Altering the Genome by Homologous Recombination", *Science*, 244:1288-1292; (1989).

Chait et al., "Weighing Naked Proteins: Practical, High-Accuracy Mass Measurement of Peptides and Proteins", *Science*, 257:1885-1894; (1992).

Chen et al., "IL-1β Induces Serine Protease Inhibitor 3 (SPI-3) Gene Expression in Rat Pancreatic β-Cells. Detection by Differential display of Messenger RNA", *CYTOKINE*, 11(11):856-862; (1999).

Chen et al., "Interaction of Phosphorylated FcγeRIγ Immunoglobulin Receptor Tyrosine Activation Motif-based Peptides with Dual and Single SH2 Domains of p72$^{syk}$", *J. Biol. Chem.*, 271(41):25308-25315; (1996).

Cline et al., "Perspectives for Gene Therapy: Inserting New Genetic Information into Mammalian Cells by Physical Techniques and Viral Vectors", *Pharmac. Ther.*, 29:69-92; (1985).

Clowes et al., "Long-Term Biological Response of Injured Rat Carotid Artery Seeded with Smooth Muscle Cells Expressing Retrovirally Introduced Human Genes". *J. Clin. Invest.*, 93:644-651; (1994).

Cole et al., in *Monoclonal Antibodies and Cancer Therapy*, "The EBV-Hybridoma Technique and Its Application to Human Lung Cancer", *Alan R. Liss, Inc.*, pp. 77-96; (1985).

Coombs et al., "Revisiting Catalysis by Chymotrypsin Family Serine Proteases Using Peptide Substrates and Inhibitors with Unnatural Main Chains", *J. Biol. Chem.*, 274(34):24074-24074; (1999).

Coombs et al., "Substrate specificity of prostate-specific antigen (PSA)", *Chem. Biol.*, 5(9):475-488; (1998).

Coombs et al., "Directing Sequence-Specific Proteolysis to New Targets. The Influence Of Loop Size And Target Sequence Of Selective Proteolysis By Tissue-Type Plasminogen Activator And Urokinase-Type Plasminogen Activator", *J. Biol. Chem.*, 273(8):4323-4328; (1998).

Coombs et al., "Distinct Mechanisms Contribute to Stringent Substrate Specificity of Tissue-type Plasminogen Activator", *J. Biol. Chem.*, 271(8):4461-4467; (1996).

Cote et al., "Generation of human monoclonal antibodies reactive with cellular antigens", *Proc. Natl. Acad. Sci. U.S.A.*, 80:2026-2030; (1983).

Cotten et al., "Receptor-Mediated Transport of DNA into Eukaryotic Cells", *Meth. Enzymol.*, 218:619-645; (1993).

Crowley et al., "Prevention of metastasis by inhibition of the urokinase receptor", *Proc. Natl. Acad. Sci. U.S.A..*, 90:5021-5025; (1993).

Cumber et al., "Structural Features of the Antibody-A Chain Linkage that Influences the Activity and Stability of Rictin A Chain Immunotoxins", *Bioconj. Chem.*, 3:397-401; (1992).

Cwirla et al., "Peptides on phage: A vast library of peptides for identifying ligands", *Proc. Natl. Acad. Sci. U.S.A.*, 87:6378-6382; (1990).

Delaria et al., "Characterization of Placental Bikunin, a Novel Human Serine Protease Inhibitor", *J. Biol. Chem.*, 272(18):12209-12214; (1997).

Dillon, "Regulating gene expression in gene therapy", *TIBTECH*, 11(5):167-173; (1993).

Ding et al., "Origins of the specificty of tissue-type plasminogen activator", *Proc. Natl. Acad. Sci. U.S.A.*, 92(17):7627-7631; (1995).

Dodet, "Commerical prospects for gene therapy—a company survey", *TIBTECH*, 11(5):182-189; (1993).

Dower et al., "The Search for Molecular Diversity (II): Recombinant and Synthetic Randomized Peptide Libraries", *An. Rep. Med. Chem.*, 26:271-280; (1991).

Dryjanski et al., "*N*-Tosyl-L-phenylalanine Chloromethyl Ketone, a Serine Protease Inhibitor, Identifies Glutamate 398 at the Coenzyme-Binding Site of Human Aldehyde Dehydrogenase. Evidence for a Second "Naked Anion" at the Active Site", *Biochem.*, 37(40):14151-14156; (1998).

Dufer et al., "Differential Effect of the Serine Protease Inhibitor Phenyl Methyl Sulfonyl Fluoride on Cytochemically Detectable Esterases in Human Leucocytes and Platelets", *Scand. J. Haematol.*, 32(1):25-32; (1984).

Dzau et al., "Gene therapy for cadiovascular disease", *TIBTECH*, 11(5):205-210; (1993).

Eck et al., "Structure of TNF-α: Implications for Receptor Binding", *J. Biol. Chem.*, 26:17605; (1989).

Edwards et al., "Inhibition of elastase by a synthetic cotton-bound serine protease inhibitor: in vitro kinetics and inhibitor release", *Wound Repair Regen.*, 7(2):106-118; (1999).

Erickson et al., "Design, Activity, and 2.8 Å Crystal Structure of a C2 Symmetric Inhibitor Complexed to HIV-1 Protease", *Science*, 249:527-533; (1990).

Evans et al., "Design of Nonpeptidal Ligands for a Peptide Receptor: Cholecystokinin Antagonists", *J. Med. Chem.*, 30:1229-1239; (1987).

Farley et al., "Cloning and sequence analysis of rat hepsin, a cell surface serine proteinase", *BioChem. Biophys. Acta*, 1173:350-352; (1993).

Fattom et al., "Comparative Immunogenicity of Conjugates Composed of the *Staphylococcus aureus* Type 8 Capsular Polysaccharide Bound to Carrier Proteins by Adipic Acid Dihydrazide or *N*-Succinimidyl-3-(2-Pyridyldithio)propionate", *Infection & Immun.*, 60(1):584-589; (1992).

Fauchere, "Elements for the Rational Design of Peptide Drugs", *Adv. Drug Res.*, 15:29-69; (1986).

Fay et al., "Platelets inhibit fibrinolysis in vitro by both plasminogen activator inhibitor dependent and -independent mechanisms", *Blood*, 83(2):351-356; (1994).

Feinstein et al., "Thrombin, Collagen and A23187 Stimulated Endogenous Platelet Arachidonate Metabolism: Differential Inhibition by $PGE_1$, Local Anesthetics and a Serine-Protease Inhibitor", *Prostaglandins*, 14(6):1075-1093; (1977).

Findeis et al., "Targeted delivery of DNA for gene therapy via receptors", *TIBTECH*, 11(5):202-205; (1993).

Forney et al., "Interaction of the human Serine Protease Inhibitor α-1-Antitrypsin with *Cryptosporidium Parvum*", *J. Parasitol.*, 82(3):496-502; (1996).

Friedmann et al., "Gene Therapy for disorders of the nervous system", *TIBTECH*, 11(5):192-197; (1993).

Fujise et al., "A tissue plasminogen activator/P-selectin fusion protein is an effective thrombolytic agent", *Circulation*, 95(3):715-722; (1997).

Gante, "Peptidomimetics-tailored Enzyme Inhibitors", *Angew. Chem. Int. Ed. Engl.*, 33:1699-1720; (1994).

Gautier et al., "α-DNA IV: α-anomeric and β-anomeric tetrathymidylates covalently linked to intercalating oxazolopyridocarbazole. Synthesis, physicochemical properties and poly (rA) binding", *Nucl. Acids Res.*, 15:6625-6641; (1987).

Gething et al., "Varients of human tissue-type plasminogen activator that lack specific structural domains of the heavy chain", *EMBO J.*, 7(9):2731-2740; (1988).

Ghendler et al., "Schistosoma mansoni: Isolation and Characterization of Smpi56, a Novel Serine Protease Inhibitor", *Exp. Parasitol.*, 78:121-131; (1994).

Goldmacher et al., Photoactivation of "Toxin Conjugates", *Bioconj. Chem.*, 3:104-107; (1992).

Goldspiel et al., "Human gene therapy", *Clinical Frontiers, Clinical Therapy*, 12:488-505; (1993).

Gonzalez et al., "Voltage Sensing by Fluorescence Resonance Energy Transfer in Single Cells", *Biophys. J.*, 69:1272-1280; (1995).

Grossman et al., "Retroviruses: delivery vehicle to the liver", *Curr. Opin. in Genetics and Devel.*, 3:110-114; (1993).

Hamdaoui et al., "Purification of a Novel, Heat-Stable Serine Protease Inhibitor Protein from Ovaries of the Desert Locust, *Schistocerca gregaria*", *Biochem. Biophys. Res. Commun.*, 238:357-360; (1997).

Hameed et al., "3,4-Dichloroisocoumarin Serine Protease Inhibitor Induces DNA Fragmentation and Apoptosis in susceptible Target Cells", *DCI and Apoptosis, Proc. Soc. Exp. Biol. Med.*, 219(2):132-137; (1998).

Harper et al., "Reaction of Serine Proteases with Substituted Isocoumarins: Discovery of 3,4-Dichloroisocoumarin, a New General Mechanism Based Serine Protease Inhibitor" *Biochem.*, 24:1831-1841; (1985).

Hazum et al., "A Photocleavable Protecting Group for the Thiol Function of Cysteine", Department of Organic Chemistry, The Weizmann Institute of Science Rehovot, Israel, *Pept., Proc. Eur. Pept. Symp.*, 16th, Brunfeldt, K (ED), pp. 105-110; (1981).

Hervio et al., "Negative selectivity and the evolution of protease cascades: the specificity of plasmin for peptide and protein substrates", *Chem. Biol.*, 7(6):443-453; (2000).

Hesse et al., "Effects of the Serine Protease Inhibitor Gabexate Mesilate on Purified Pancreatic Phospholipids $A_2$", *Pharmacol. Res. Commun.*, 16(7):637-645; (1984).

Hill et al., "A new intracellular serine protease inhibitor expressed in the rat pituitary gland complexes with granzyme B", *FEBS Lett.*, 440:361-364; (1998).

Hiwasa et al., "Potent growth-suppressive activity of a serine protease inhibitor, ONO-3403, toward malignant human neuroblastoma cell lines", *Cancer Lett.*, 126:221-225; (1998).

Holmes, "Primary Structure of Human $\alpha_2$-Antiplasmin, a serine Protease Inhibitor (Serpin)", *J. Biol. Chem.*, 262(4):1659-1664; (1987).

Holstein et al., "The primitive metazoan *Hydra* expresses antistasin, a serine protease inhibitor of vertebrate blood coagulation: cDNA cloning, cellular localisation and development regulation", *FEBS Lett.*, 309(3):288-292; (1992).

Hooper et al., "Type II Transmembrane Serine Proteases", *J. Biol. Chem.*, 276:857-860; (2001).

Houenou et al., "A serine protease inhibitor, protease nexin I, rescues motoneurons from naturally occurring and axotomy-induced cell death", *Proc. Natl. Acad. Sci. U.S.A..*, 92:895-899; (1995).

Hruby et al., "Emerging approaches in the molecular design of receptor-selective peptide ligands: conformational, topographical and dynamic considerations", *Biochem J.*, 268:249-262; (1990).

Huang et al., "Serine protease inhibitor TPCK prevents Taxol-induced cell death and blocks c-Raf-1 and Bcl-5 phosphorylation in human breast carcinoma cells", *Oncogene*, 18:3431-3439; (1999).

Huse et al., "Generation of a Large Combinatorial Library of the Immunoglobulin Repertoire in Phage Lambda", *Science*, 246:1275-1281; (1989).

Huston et al., "Protein engineering of antibody binding sites: Recovery of specific activity in an anti-digoxin single-chain Fv analogue produced in *Escherichia coli*", *Proc. Natl. Acad. Sci. U.S.A.* 85:5879-5883; (1988).

Iijima et al., "Stage-Specific Inhibition of *Xenopus* Embryogenesis by Aprotinin, a Serine Protease Inhibitor", *J. Biochem. (Tokyo)*, 126:912-916; (1999).

Inoue et al., "Sequence-dependent hydrolysis of RNA using modified oligonucleotide splints and RNase H", *FEBS Lett.* 215(2):327-330; (1987).

Inoue et al., "Synthesis and Hybridization studies on two complementary nona(2'-O-methyl)ribonucleotides", *Nucl. Acids Res.* 15(15):6131-6148; (1987).

Jacquinet et al., "Cloning, genomic organization, chromosomal assignment and expression of a novel mosaic serine proteinase: epitheliasin", *FEBS Lett.*, 468:93-100; (2000).

Jameson et al., "Fluorescence Anisotropy Applied to Biomolecular Interactions", *Methods Enzymol.*, 246:283-300; (1995).

Jankun et al., "Inhibitors of Urokinase Reduce Size of Prostate Cancer Xenografts in Severe Combined Immunodeficient Mice", *Canc. Res.*, 57:559-563; (1997).

Jessop et al., "Effects of Serine Protease Inhibitor, Tame, on IL-1β in LPS-Stimulated Human Monocytes: Relationship Between Synthesis and Release of a 33-kDa Precursor and the 17-kDa Biologically Active Species", *Inflammation*, 17(5):613-631; (1993).

Ji et al., "Two-dimensional electrophoretic analysis of proteins expressed by normal and cancerous human crypts: Application of mass spectrometry to peptide-mass fingerprinting", *Electrophoresis*, 15:391-405; (1994).

Jolley, "Fluorescence Polarization Assays for the Detection of Proteases and Their Inhibitors", *J. Biomol. Screening*, 1(1):33-38; (1996).

Kalaria et al., "Serine Protease Inhibitor Antithrombin III and Its Messenger RNA in the Pathogenesis of alzheimer's Disease", *Am. J. Pathol.*, 143(3):886-893; (1993).

Kaminogo et al., "Combination of Serine Protease Inhibitor FUT-175 and Thromboxane Synthtase Inhibitor OKY-046 Decreases Cerebral Vasospasm in Patients with Subarachnoid Hemorrhage", *Neurol. Med. Chir. (Tokyo)*, 38:704-709; (1998).

Kawaguchi et al., "Purification and Cloning of hepatocyte Growth Factor Activator Inhibitor Type 2, a Kunitz-type serine Protease Inhibitor", *J. Biol. Chem.*, 272(44):27558-27564; (1997).

Ke et al., "Distinguishing the Specificities of Closely Related Proteases. Role of P3 In Substrate And Inhibitor Discrimination Between Tissue-type Plasminogen Activator And Urokinase", *J. Biol. Chem.*, 272(26):16603-16609; (1997).

Ke et al., "Rapid and efficient site-directed mutagenesis by single-tube 'megaprimer' PCR method", *Nucl. Acids Res.*, 25(16):3371-13372; (1997).

Ke et al., "Identification of a Hydrophobic Exosite on Tissue Type Plasminogen Activator That Modulates Specificity for Plasminogen", *J. Biol. Chem.*, 272(3):1811-1816; (1997).

Ke et al., "Optimal Subsite Occupancy and Design of a Selective Inhibitor of Urokinase", *J. Biol. Chem.*, 272(33):20456-20462; (1997).

Kiem et al., "Retrovirus-Mediated Gene Transduction Into Canine Peripheral Blood Repopulating Cells", *Blood* 83(6):1467-1473; (1994).

Kim et al., "Cloning and chromosomal mapping of a gene isolated from thymic stromal cells encoding a new mouse type II membrane serine protease, epithin, containing four LDL receptor modules and two CUB", *Immunogenetics*, 49:420-428; (1999).

Kim et al., "A Cysteine-Rich Serine Protease Inhibitor (Guamerin II) from the Non-Blood Sucking Leech *Whitmania Edentual*: Biochemical Characterization and Amino Acid Sequence Analysis", *J. Enzym. Inhib.*, 10:81-91; (1996).

Kitamoto et al., "Enterokinase, the initiator of intestinal digestion, is a mosaic protease composed of a distinctive assortment of domains", *Proc. Natl. Acad. Sci. U.S.A.*, 91:7588-7592; (1994).

Kitamoto et al., "cDNA Sequence and Chromosomal Localization of Human Enterokinase, the Proteolytic of Trypsinogen", *Biochem.*, 34(14):4562-4568; (1995).

Kobayashi et al., "Inhibition of Metastasis of Lewis Lung Carcinoma by a Synthetic Peptide within Growth Factor-like Domain of Urokinase in the Experimental and Spontaneous Metastasis Model", *Int. J. Canc.*, 57:727-733; (1994).

Köhler et al., "Continuous cultures of fused cells secreting antibody of predefined specificity", *Nature*, 526:495-497; (1975).

Koller et al., "Inactivating the $\beta_2$-microglobulin locus in mouse embryonic stem cells by homologous recombination", *Proc. Natl. Acad. Sci. USA* 86:8932-8935; (1989).

Kozak, "Structural Features in Eukaryotic mRNAs That Modulate the Initiation of Translation", *J. Biol. Chem.*, 266(30):19867-19870; (1991).

Kozarsky et al., "Gene therapy: adenovirus vectors", *Genetics and Development*, 3:499-503; (1993).

Kozbor et al., "The production of monoclonal antibodies from human lymphocytes", *Immunology Today* 4(3):72-79; (1983).

Ladurner et al., "Glutamine, Alanine or Glycine Repeats Inserted into the Loop of a Protein Have Minimal Effects on Stability and Folding Rates", *J. Mol. Biol.*, 273:330-337; (1997).

Le Cam et al., "Growth Hormone-Mediated Transcriptional Activation of the Rat Serine Protease Inhibitor 2.1 Gene Involves Both Interleukin-1 β-Sensitive and -Insensitive Pathways", *Biochem. Biophys. Res. Commun.*, 253(2):311-314; (1998).

Lee et al., "Activation of Hepatocyte Growth Factor and Urokinase/Plasminogen Activator by Matriptase, an Epithelial Membrane Serine Protease", *J. Biol. Chem.*, 275(47):36720-36725; (2000).

Lemaitre et al., "Specific antiviral activity of a poly(L-lysine)-conjugated oligodeoxyribonucleotide sequence complementary to vesicular stomatitis virus N protein mRNA initiation site", *Proc. Natl. Acad. Sci. U.S.A.*, 84:648-652; (1987).

Lerner et al., "High Throughput Screen for Inhibitors of Bacterial DNA Topoisomerase I Using the Scintillation Proximity Assay", *J. Biomol. Screening*, 1(3):135-143; (1996).

Letsinger et al., "Cholesteryl-conjugated oligonucleotides: Synthesis, properties, and activity as inhibitors of replication of human immunodeficiency virus in cell culture", *Proc. Natl. Acad. Sci. U.S.A.*, 86:6553-6556; (1989).

Leytus et al., "A Novel Trypsin-like Serine Protease (Hepsin) with a Putative Transmembrane domain Expressed by Human Liver and Hepatoma Cells", *Biochem.*, 27:1067-1074; (1988).

Lin et al., "Molecular Cloning of cDNA for Matriptase, a Matrix-degrading Serine Protease with Trypsin-like Activity", *J. Biol. Chem.*, 274(26):18231-18236; (1999).

Lin et al., "Purification and Characterization of a Complex Containing Matriptase and a Kunitz-type Serine Protease Inhibitor from Human Milk", *J. Biol. Chem.*, 274(26):18237-18242; (1999).

Lin et al., "Characterization of a Novel, Membrane-bound, 80-kDa Matrix-degrading Protease from Human Breast Cancer Cells", *J. Biol. Chem.*, 272(14):9147-9152; (1997).

Lindmark et al., "Pulmonary Function in Middle-aged Women with Heterozygous Deficiency of the Serine Protease Inhibitor Alpha-antichymotrypsin", *Am. Rev. Respir. Des.*, 141:884-888; (1990).

Liu et al., "Identification of a Novel Serine Protease-like Gene, the Expression of Which Is Down-Regulated during Breast Cancer Progression", *Cancer Res.*, 56:3371-3379 (1996).

Liu et al., "Matrix Localization of Tissue Factor Pathway Inhibitor-2/Matrix-Associated Serine Protease Inhibitor (TFPI-2/MSPI) Involves Arginine-Mediated Ionic Interactions with Heparin and Dermatan Sulfate: Heparin Accelerates the Activity of TFPI-2/MSPI toward Plasmin", *Arch. Biochem. Biophys.*, 370(1):112-118; (1999).

Loeffler et al., "Gene Transfer into Primary and Established Mammalian Cell Lines with Lipopolyamine-Coated DNA", *Meth. Enzymol.*, 217:599-618; (1993).

Lundqvist et al., Original Research Papers, "The Serine protease inhibitor diisopropylfluorophosphate inhibits neutrophil NADPH-oxidase activity induced by the calcium ionophore ionomycin and serum opsonised yeast particles", *Inflamm. Res.*, 44(12):510-517; (1995).

Luthman et al., "Peptides and Peptidomimetics", Book: *A Textbook of Drug Design and Development*, 2nd Ed., Harwood Academic Publishers, 14:386-406; (1996).

Lynch et al., "A Fluroescence Polarization Based SrC-SH2 Binding Assay", *Anal. Biochem.*, 247:77-82; (1997).

Maake et al., "The Growth Hormone Dependent Serine Protease Inhibitor, Spi 2.1 Inhibits the Des (1-3) Insulin-Like Growth Factor-I Generating Protease", *Endocrinology*, 138(12):5630-5636; (1997).

Madison E.L., "Substrate Specificity of Tissue Type Plasminogen Activator", *Adv. Exp. Med. Biol.*, 425:109-121; (1997).

Madison et al., "Substrate Specificity of Tissue Type Plasminogen Activator. Characterization Of The Fibrin Independent Specificity Of t-PA For Plasminogen", *J. Biol. Chem.*, 270(13):7558-7562; (1995).

Madison E.L., "Studies of Serpins Unfold at a Feverish Pace", *J. Clin. Invest.*, 94(6):2174-2175; (1994).

Madison et al., "Converting Tissue Plasminogen Activator to a Zymogen: A Regulatory Triad of ASP-His-Ser", *Science*, 262(5132):409-421; (1993).

Madison, E.L., "Probing Structure/Function Relationships of Tissue-type Plasminogen Activator by Site Specific Mutagenesis", *Fibrinolysis*, 81(Suppl. 1):221-236; (1994).

Madison et al., "Probing Structure-Function Relationships of Tissue-Type Plasminogen Activator by Oligonucleotide-Mediated Site-Specific Mutagenesis", *Methods Enzymol.*, 223:249-271; (1993).

Madison et al., "A vector, pSHT, for the expression and secretion of protein domains in mammalian cells", *Gene*, 121(1):179-180; (1992).

Madison et al., "Restoration of Serine Protease-Inhibitor Interaction by Protein Engineering", *J. Biol. Chem.*, 265(35):21423-21426; (1990).

Madison et al., "Amino acid residues that affect interaction of tissue-type plasminogen activator with plasminogen activator inhibitor 1", *Proc. Natl. Acad. Sci. U.S.A.*, 87(9):3530-3533; (1990).

Madison et al., "Serpin-resistant mutants of human tissue type plasminogen activator", *Nature*, 339(6227):721-724; (1989).

Marlor et al., "Identification and Cloning of Human Placentral Bikunin, a Novel Serine Protease Inhibitor Containing Two Kunitz Domains", *J. Biol. Chem.*, 272(18):12202-12208; (1997).

Mastrangeli et al., "Diversity of Airway Epithelial Cell Targets for In Vivo Recombinant Adenovirus-mediated Gene Transfer", *J. Clin. Invest.* 91:225-234; (1993).

Matrisian et al., "Stromelysin/transin and tumor progression", *Cancer Biol.*, 1:107-115; (1990).

Matsushima et al., "Structural Characterization of Porcine Enteropeptidase", *J. Biol. Chem.*, 269(31):19976-19982; (1994).

McDonald, "Thrombopoietin. Its Biology, clinical Aspects, and Possibilities", *Am. J. of Pediatric Hematology/Oncology*, 14 (1):8-21; (1992).

Mc Donell et al., "Stromelysin in tumor progression and metastasis", *Cancer and Metastasis Reviews*, 9:305-319; (1990).

McPhalen et al., "Preliminary Crystallographic Data for the Serine Protease Inhibitor CI-2 from Barley Seeds", *J. Mol. Biol.*, 168:445-447; (1983).

Mellgren et al., "The Influence of a Serine Protease Inhibitor, Nafamostat Mesilate, on Plasma Coagulation, and Platelet Activation during Experimental Extracorporeal Life Support (ECLS)", *Thromb. Haemost.*, 79:342-347; (1998).

Miller et al., "Use of Retroviral Vectors for Gene Transfer and Expression", *Meth. Enzymol.* 217:581-599; (1993).

Min et al., "Urokinase Receptor Antagonists Inhibit Angiogenesis and Primary Tumor Growth in Syngeneic Mice", *Canc. Res.*, 56:2428-2433; (1996).

Mitani et al., "Delivery therapeutic genes—matching approach and application", *TIBTECH*, 11(5):162-166; (1993).

Modha et al., "An association between schistosomes and contrapsin, a mouse serine protease inhibitor (serpin)", *Parasitology*, 96:99-109; (1988).

Monfardini et al., "A Branched Monomethoxypoly(ethylene glycol) for Protein Modification", *Bioconjugate Chem.*, 6(1):62-69; (1995).

Morgan et al., "Human Gene Therapy", *Annu. Rev. Biochem.*, 62:191-217; (1993).

Morgan et al., "Approaches to the Discovery of Non-Peptide Ligands for Peptide receptors and Peptidases", Book: *Annu. Rep. Med. Chem.*, Chapter 26, Section VI, 24:243-252.

Morrison et al., "Chimeric human antibody molecules: Mouse antigen-binding domains with human constant region domains", *Proc. Natl. Acad. Sci. USA*, 81:6851-6855; (1984).

Moser et al., "Bdellastasin, a serine protease inhibitor of the antistasin family from the medical leech (*Hirudo medicinalis*)", *Eur. J. Biochem.*, 253:212-220: (1998).

Mulligan, "The Basic Science of Gene Therapy", *Science*, 260:926-932; (1993).

Nabel et al., "Direct gene transfer for immuotherapy and immunization", *TIBTECH*, 11(5):211-215; (1993).

Nakabo et al., "Lysis of leukemic cells by human macrophages: inhibition by 4-(2-aminoethyl)-benzenesulfonyl fluoride (AEBSF), a serine protease inhibitor", *J. Leukoc. Biol.*, 60:328-336; (1996).

Neuberger et al., "Recombinant antibodies possessing novel effector functions", *Nature*, 312:604-608; (1984).

Newton et al., "Angiogenin Single-Chain Immunofusions: Influence of Peptide Linkers and Spacers between Fusion Protein Domains", *Biochemistry*, 35:545-553; (1996).

Niimi et al., "A *Drosophila* gene encoding multiple splice variants of Kazal-type serine protease inhibitor-like proteins with potential destinations of mitochondria, cytosol and the secretory pathway", *Eur. J. Biochem.*, 266:282-292; (1999).

Nogrady, "Pro-Drugs and Soft Drugs", Book: *Medicinal Chemistry A Biochemical Approach*, Oxford University Press, NY, pp. 388-392; (1985).

Ohkoshi et al., "Effects of Serine Protease Inhibitor FOY-305 and Heparin on the Growth of Squamous Cell Carcinoma", *Anticancer Res.*, 13:963-966; (1993).

O'Reilly, "The preclinical evaluation of angiogenesis inhibitors", *Investigational New Drugs*, 15:5-13; (1997).

Orth et al., "Complexes of tissue-type plasminogen activator and its serpin inhibitor plaminogen-activator inhibitor type 1 are internalized by means of the low density lipoprotein receptor-related protein/$\alpha_2$-macroglobulin receptor", *Proc. Natl. Acad. Sci. U.S.A.*, 89(16):7422-7426; (1992).

Ossowski, "In Vivo Invasion of Modified Chorioallantoic Membrane by Tumor Cells: the Role of Cell Surface-bound Urokinase", *J. Cell Biol.*, 107(6, Pt. 1):2437-2445; (1988).

Osterwalder et al., "Neuroserpin, an axonally secreted serine protease inhibitor", *EMBO J.*, 15(12):2944-2953; (1996).

Palencia et al., "Determination of Activable Proacrosin/Acrosin in Bovine Sperm Using an Irreversible Isocoumarin Serine Protease Inhibitor", *Biol. Reprod.*, 55:536-542; (1996).

Paoloni-Giacobino, "Cloning the TMPRSS2 Gene, Which Encodes a Novel Serine Protease with Transmembrane, LDLRA, and SRCR Domains and Maps to 21q22.3", et al., *Genomics*, 44:309-320; (1997).

Parodi et al., "Gabexate Mesilate, A New Synthetic Serine Protease Inhibitor: A Pilot Clinical Trial in Valvular Heart Surgery", *J. Cardiothorac. Vasc. Anesth.*, 10(2):235-237; (1996).

Paul et al., "Characterization of three transcriptional repressor sites within the 3' untranslated region of the rat serine protease inhibitor 2.3 gene", *Eur. J. Biochem.*, 254(3):538-546; (1998).

Porteous et al., "How relevant are mouse models for human diseases to somatic gene therapy", *TIBTECH*, 11(5):173-181; (1993).

Rabbani et al., "Prevention of Prostate-cancer Metastasis In Vivo by a Novel Synthetic Inhibitor of Urokinase-type Plasminogen Activator (uPA)", *Int. J. Cancer*, 63:840-845; (1995).

Rao et al., "Extracellular Matrix-Associated Serine Protease Inhibitors (M, 33,000, and 27,000) Are Single-Gene Products with Differential Glycosylation: cDNA Cloning of the 33-kDa Inhibitor Reveals Its Identity to Tissue Factor Pathway Inhibitor-2", *Arch. Biochem. Biophys.*, 335(1):82-92; (1996).

Rao et al., "HT-1080 Fibrosarcoma Cell Matrix Degradation and Invasion are Inhibited by the Matrix-Associated Serine Protease Inhibitor TFPI-2/33 kDa MSPI", *Int. J. Cancer*, 76:749-756; (1998).

Ravichandran et al., "Cryocrystallography of a Kunitz-type serine protease inhibitor: the 90 K structure of winged bean chymotrysin inhibitor (WCI) at 2.13 Å resolution", *Acta Cryst.*, D55:1814-1821; (1999).

Rizo et al., "Constrained Peptides: Models of Bioactive Peptides and Protein substructures", *An. Rev. Biochem.*, 61:387-418; (1992).

Robinson, "Gene therapy—proceeding form laboratory to clinic", *TIBTECH*, 11(5):155-159; (1993).

Roch et al., "Characterization of a 14 kDa Plant-related Serine Protease Inhibitor and Regulation of Cytotoxic Activity in Earthworm Coelomic Fluid", *Dev. Comp. Immunol.*, 22(1):1-12; (1998).

Rosenfeld et al., "In Vivo Transfer of the Human Cystic Fibrosis Transmembrane Conductance Regulator Gene to the Airway Epithelium", *Cell*, 68:143-155; (1992).

Rosenfeld et al., "Adenovirus-mediated Transfer of a Recombinant α1-Antirypsin Gene to the Lung Epithelium in Vivo", *Science*, 252:431-434; (1991).

Rusbridge et al., "3,4-Dichloroisocoumarin, a serine protease inhibitor, inactivates glycogen phosphorylase b", *FEBS Lett.*, 268(1):133-136; (1990).

Ryo et al., "Treatment of Post-Transfusion Graft-versus-Host Disease with Nafmostat Mesilate, a Serine Protease Inhibitor", *Vox Sang.*, 76:241-246; (1999).

Salmons et al., "Targeting of Retroviral Vectors for Gene Therapy", *Human Gene Therapy*, 4:129-141; (1993).

Sarver et al., "Ribozymes as Potential Anti-HIV-1 Therapeutic Agents", *Science*, 247:1222-1225; (1990).

Sawada et al., "Prevention of Neointimal Formation by a Serine Protease Inhibitor, FUT-175, After Carotid Balloon Injury in Rats", *Stroke*, 30(3):644-650; (1999).

Scalia et al., "Beneficial Effects of LEX032, A Novel Recombinant Serine Protease Inhibitor, in Murine Traumatic Shock", *Shock*, 4(4):251-256; (1995).

Scuderi, "Suppression of Human Leukocyte Tumor Necrosis Factor Secretion by the Serine Protease Inhibitor $_p$-Tolunenesulfonyl-L-Arginine Methyl Ester (Tame)", *J. Immunol.*, 143(1):168-173; (1989).

Sekar et al., "Specificity of the Serine Protease Inhibitor, Phenylmethylsulfonyl Fluoride", *Biochem. Biophys. Res. Commun.*, 89(2):474-478; (1979).

Senda et al., "Treatment of Ulcerative Colitis with Camostat Mesilate, A Serine Protease Inhibitor", *Intern. Med.*, 32(4):350-354; (1993).

Senter et al., "Novel Photocleavable Protein Crosslinking Reagents and Their Use in the Preparation of Antibody-Toxin Conjugates", *Photochem. Photobiol.*, 42(3):231-237; (1985).

Seto et al., "Central Effect of Aprotinin, a Serine Protease Inhibitor, on Blood Pressure in Spontaneously Hypertensive and Wistar-Kyoto Rats", *Adv. Exp. Med. Biol.*, 247B:49-54; (1989).

Seto et al., "The Effect of Aprotinin (A Serine Protease Inhibitor) on Renal Function and Renin Release", *Hypertension*, 5(6):893-899; (1983).

Shimomura et al., "Hepatocyte Growth Factor Activator Inhibitor, a Novel Kunitz-type Serine Protease Inhibitor", *J. Biol. Chem.*, 272(10):6370-6376; (1997).

Shiozaki et al., "Effect of FUT-187, Oral Serine Protease Inhibitor, on Inflammation in the Gastric Remnant", *Jpn. J. Cancer Chemother*, 23(14):1971-1979; (1996).

Shohet et al., "Inhibitor-Resistant Tissue-Type Plasminogen Activator: An Improved Thrombolytic Agent In Vitro", *Thromb Haemost.*, 71(1):124-128; (1994).

Sikora, "Gene therapy for cancer", *TIBTECH*, 11(5):197-201; (1993).

Silverman et al., "New assay technologies for high-throughput screening" *Curr. Opin. Chem. Biol.*, 2(3):397-403; (1998).

Simar-Blanchet et al., "Regulation of expression of the rat serine protease inhibitor 2.3 gene by glucocorticoids and interleukin-6. A complex and unusual interplay between positive and negative cis-acting elements", *Eur. J. Biochem.*, 236(2):638-648; (1996).

Sittampalam et al., "High-throughput screening: advances in assay technologies", *Curr. Opin. Chem. Biol.*, 1:384-394; (1997).

Smith et al., "Protein Loop Grafting to Construct a Variant of Tissue-type Plaminogen Activator That Binds Platelet Integrin αIIbβ3", *J. Biol. Chem.*, 270(51):30486-30490; (1995).

Sonatore et al., "The Utility of FK506-Binding Protein as a Fusion Partner in Scintillation Proximity Assays: Application of SH2 Domains", *Anal. Biochem.*, 240:289-297; (1996).

Stankiewicz et al., "3' Noncoding sequences of the *CTA 1* gene enhance expression of the recombinant serine protease inhibitor, CPTI II, in *Saccharomyces cerevisiae*", *Acta Biochim. Pol.*, 43(3):525-529; (1996).

Steele et al., "Pigment epithelium-derived factor: Neutrophic activity and identification as a member of the serine protease inhibitor gene family", *Proc. Natl. Acad. Sci. U.S.A.*., 90(4):1526-1530; (1993).

Stemple et al., "Isolation of a Stem Cell for Neurons and Glia from the Mammalian Neural Crest", *Cell*, 71:973-985; (1992).

Strandberg et al., "Variants of Tissue-type Plasminogen Activator with Substantially Enhanced Response and Selectivity toward Fibrin Co-factors", *J. Biol. Chem.*, 270(40):23444-23449; (1995).

Sullivan et al., "Development of a Scintillation Proximity Assay for Calcineurin Phosphatase Activity", *J. Biomol. Screening*, 2:19-23; (1997).

Tachias et al., "Variants of Tissue-type Plasminogen Activator That Display Extraordinary Resistance to Inhibition by the Serpin Plasminogen Activator Inhibitor Type 1", *J. Biol. Chem.*, 272(23):14580-14585; (1997).

Tachias et al., "Covering Tissue-type Plasminogen Activator into a Zymogen. Important Role Of Lys156", *J. Biol. Chem.*, 272(1):28-31; (1997).

Tachias et al., "Covering Tissue-type Plasminogen Activator into a Zymogen", *J. Biol. Chem.*, 271(46):28749-28752; (1996).

Tachias et al., "Variants of Tissue-type Plasminogen Activator Which Display Sunstantially Enhanced Stimulation by Fibrin", *J. Biol. Chem.*, 270(31):18319-18322; (1995).

Takeda et al., "Construction of Chimeric processed immunoglobulin genes containing mouse variable and human constant region sequences", *Nature*, 314:452-454; (1985).

Takeuchi et al., "Reverse biochemistry: Use of macromolecular protease inhibitors to dissect complex biological process and identify a membrane-type serine protease in epithelial cancer and normal tissue", *Proc. Natl. Acad. Sci. USA*, 96:11054-11061; (1999).

Takeuchi et al., "Cellular Localization of Membrane-type Serine Protease 1 and Identification of Protease-activated Receptor-2 and Single-chain Urokinase-type Plasminogen Activator as Substrates", *J. Biol. Chem*, 275(34):26333-26342; (2000).

Tanimoto et al., "Hepsin, a Cell Surface Serine Protease Indentified in Hepatoma Cells, Is Overexpressed in Ovarian Cancer", *Cancer Res.*, 57:2884-2887; (1997).

Tolstoshev, "Gene Therapy, Concepts, Current Trials and Future Directions", *Annu Rev. Pharmacol. Toxicol.*, 32:573-596; (1993).

Tomita et al., "A Novel Low-Density Lipoprotein Receptor-Related Protein with Type II Membrane Protein-Like Structure Is Abundant in Heart", *J. Biochem.*, 124:784-789; (1998).

Treadwell et al., "Cartilage Synthesizes the Serine Protease Inhibitor PAI-1: Support for the Involvement of Serine Proteases in Cartilage Remodeling", *J. Orthop. Res.*, 9(3):309-316; (1991).

Tsutsui et al., "Cross-linking of Proteins to DNA in Newly Synthesized Chromatin By Diisopropylfluorophopshate, A Serine Protease Inhibitor", *Biochem. Biophys. Re. Commun.*, 123(1):271-277; (1984).

van der Krol et al., "Modulation of Eukaryotic Gene Expression by Complementary RNA or DNA Sequences", *BioTech.*, 6(10):958-976; (1988).

Veber et al., "The design of metabolically-stable peptide analogs", *TINS*, pp. 392-396; (1985).

Vu et al., "Identification and cloning of the Membrane-associated Serine Protease, Hepsin, from Mouse Preimplantation Embryos", *J. Biol. Chem.*, 272(50):31315-31320; (1997).

Wagner et al., "Nucleotide sequence of the thymidine kinase gene of herpes simplex virus type 1", *Proc. Natl. Acad. Sci. U.S.A.*, 78(3):1441-1445; (1981).

Wallrapp et al., "A Novel Transmembrane Serine Protease (TMPRSSE) Overexpressed in Pancreatic Cancer", *Cancer*, 60:2602-2606; (2000).

Walsh et al., "Gene Therapy for Human Hemoglobinopathies", *Proc. Soc. Exp. Biol. Med.*, 204:289-300; (1993).

Warren et al., "Spi-1: an hepatic serine protease inhibitor regulated by GH and other hormones", *Mol. Cell Endocrinol.*, 98(1):27-32; (1993).

Watson et al., "The Fine Structure of Bacterial and Phage Genes", Book: *Molecular Biology of the Gene*, 4th Ed., The Bejacmin/Cummings Pub. Co., 1:224; (1987).

Webber et al., "Prostate-specific Antigen, a Serine Protease, Facilitates Human Prostate Cancer Cell Invasion", *Clin. Cancer Res.*, 1:1089-1094; (1995).

Wellhöner et al., "Uptake and Concentration of Bioactive Macromoleucles by K562 Cells via the Transform Cycle Utilizing an Acid-labile Transferrin", *J. Biol. Chem.*, 266(7):4309-4314; (1991).

Werner et al., "Identification of a Protein-binding Surface by Differential Admide Hydrogen-exchange Measurements", *J. Mol. Biol.*, 225:873-889; (1992).

Whitlow et al., "An improved linker for single-chain Fv with reduced aggregation and enhanced proteolytic stability", *Protein Engineering*, 6(8):989-995; (1993).

Williamson, "From genome mapping to gene therapy", *TIBTECH*, 11(5):159-161; (1993).

Wivel, "Regulatory considerations for gene-therapy strategies and products", *TIBTECH*, 11(5):189-191 ; (1993).

Woodard et al., "Chymase-Directed Serine Protease Inhibitor That Reacts with a Single 30-kDa Granzyme and Blocks NK-Mediated Cytotoxicity", *J. Immunol.*, 153:5016-5025; (1994).

Wu et al., "Delivery systems for gene therapy", *Biotherapy*, 3:87-95; (1991).

Wu et al., "Receptor-mediated in Vitro Gene Transformation by a Soluble DNA Carrier System", *J. Biol. Chem.*, 262(1):4429-4432; (1987).

Xing et al., "Prevention of Breast Cancer Growth, Invasion, and Metastasis by Antiestrogen Tamoxifen Alone or in Combination with Urokinase Inhibitor B-428", *Canc. Res.*, 57:3585-3593; (1997).

Xu et al., "The Crystal Structure of Bikunin from the Inter-α-Inhibitor Complex: A Serine Protease Inhibitor with Two Kunitz Domains", *J. Mol. Biol.*, 276(5):955-966 (1998).

Xue et al., "Comparison of the Effects of Apo(a) Kringle IV-10 and Plasminogen Kringle on the Interactions of Lipoprotein(a) with Regulatory Molecules", *Thromb Haemost.*, 81(3):428-435; (1999).

Yahagi et al., "Complementary DNA Cloning and Sequencing of Rat Enteropeptidase and Tissue Distribution of Its mRNA", *Biochem. Biophys. Res. Commun.*, 219:806-812.

Yamamoto et al., "Identification of a Functional Promoter in the Long Terminal Repeat of Rous Sarcoma Virus", *Cell*, 22:787-797; (1980).

Yamaoka et al., "Cloning and Characterization of the cDNA for Human Airway Trypsin-like Protease", *J. Biol. Chem.*, 273(19):11894-11901; (1998).

Yamauchi et al., "Anti-Carcinogen Effects of a Serine Protease Inhibitor (FOY-305) through the Supression of Neutral Serine Protease Activity During chemical Hepatocarcinogenesis in Rats", *Hiroshima J. Med. Sci.*, 36(1):81-87 No abstract available (1987).

Yan et al., "Corin, a Mosaic Transmembrane Serine Protease Encoded by a Novel cDNA from Human Heart", *J. Biol. Chem.*, 274(21):14926-14935; (1999).

Yan et al., "Corin, a transmembrane cardiac serine protease, acts as a pro-atrial natriuretic peptide-converting enzyme", *PNAS*, 97(15):8525-8529; (2000).

Yanamoto et al., "Preventive Effect of Synthetic Serine Protease Inhibitor, FUT-175, on Cerebral Vasospasm in Rabbits", *Neurosurgery*, 30(3):351-357; (1992).

Yanamoto et al., "Therapeutic Trial of Cerebral Vasospasm with the Serine Protease Inhibitor, FUT-175, Administered in the Acute Stage after Subarachnoid Hemorrhage", *Neurosurgery*, 30(3):358-363; (1992).

Yang et al., "Ecotin: A Serine Protease Inhibitor with Two Distinct and Interacting Binding Sites", *J. Mol. Biol.*, 279:945-957; (1998).

Yen et al., "Synthesis of water-soluble copolymers containing photocleavable bonds", *Makromol. Chem.*, 190:69-82; (1989).

Yi et al., "Bikunin, a serine Protease Inhibitor, is Present on the Cell Boundary of Epidermis", *J. Invest. Dermatol.*, 113(2):182-188; (1999).

Yu et al., "Message of nexin 1, a serine protease inhibitor, is accumulated in the follicular papilla during anagen of the hair cycle", *J. Cell Sci.*, 108/:3867-3874; (1995).

Yuan et al., "Structure of murine enterokinase (enteropeptidase) and expression in small intestine during development", *Am. J. Physiol.*, 274:G342-G349; (1998).

Zallipsky, "Functionalized Poly(ethylene glycol) for Preparation of Biologically Relevant Conjugates", *Bioconjugate Chem.*, 6:150-165; (1995).

Zhang et al., "Distinct Contributions of Residue 192 to the Specificity of Coagulation and Fibrinolytic Serine Proteases", *J. Biol. Chem.*, 274(11);7153-7156; (1999).

Zhou et al., "Vaccinia Virus K2L Gene Encodes a Serine Protease Inhibitor Which Inhibits Cell-Cell Fusion", *Virology*, 189:678-686; (1992).

Zijlstra et al., "Germ-line transmission of a disrupted $\beta_3$-microglobulin gene produced by homologous recombination in embryonic stem cells", *Nature*, 342:435-438; (1989).

Zon, "Oligonucelotide Analogous as Potential Chemotherapeutic Agents", *Pharm. Res.*, 5(9):539-549; (1988).

U.S. Appl. No. 60/214,047, filed Jun. 26, 2000, Plowman et al.

Atwell et al. "Selection for improved subtilligases by phage display." Proc Natl Acad Sci U S A. 96(17):9497-502 (1999).

Bachovchin et al. "Catalytic mechanism of serine proteases: reexamination of the pH dependence of the histidyl 1J13C2-H coupling constant in the catalytic triad of alpha-lytic protease." Proc Natl Acad Sci U S A. 78(12):7323-6 (1981).

Carter et al. "Dissecting the catalytic triad of a serine protease." Nature. 332(6164):564-8 (1988).

Cheah et al. "Site-directed mutagenesis suggests close functional relationship between a human rhinovirus 3C cysteine protease and cellular trypsin-like serine protease." J Biol Chem. 265(13):7180-7. (1990).

Craik et al. :The catalytic role of the active site aspartic acid in serine proteases. Science. 237(4817):909-13 (1987).

Crameri et al. "DNA shuffling of a family of genes from diverse species accelerates directed evolution." Nature. 391(6664):288-91 (1998).

Delagrave et al. Searching sequence space to engineer proteins: exponential ensemble mutagenesis. Biotechnology (N Y). 11(13):1548-52 (1993).
Lewin, B., Ed., "Nuclear Splicing," Chapter 30 of *Genes VI*, New York: Oxford University Press, pp. 885-920 (1997).
Lopez et al. "Alternative splicing of pre-mRNA: developmental consequences and mechanisms of regulation." Annu Rev Genet. 32:279-305 (1998).
Mironov et al. "Frequent alternative splicing of human genes." Genome Res.9(12):1288-93 (1999).
Sprang et al. "The three-dimensional structure of Asn102 mutant of trypsin: role of Asp102 in serine protease catalysis." Science. 237(4817):905-9 (1987).
Wells et al. Designing substrate specificity by protein engineering of electrostatic interactions. Proc Natl Acad Sci U S A. 84(5):1219-23 (1987).
Abraham et al., "Immunochemical Identification of the Serine Protease Inhibitor $\alpha_1$-Antichymotrypsin in the Brain Amyloid Deposits of Alzheimer's Disease", *Cell*, 52:487-501 (1988).
Adams et al., "The c-myc oncogene driven by immunoglobulin enhancers induces lymphoid malignancy in transgenic mice", *Nature*, 318:533-538 (1985).
Alexander et al., "Expression of the *c-myc* Oncogene under Control of an Immunoglobulin Enhancer in $E\mu$-*myc* Transgenic Mice", *Mol. Cell Biol.*, 7(4):1436-1444 (1987).
Auerbach et al., "Angiogenesis Inhibition: A Review", *Pharmacol. Ther.*, 63(3):265-311 (1994).
Baker et al., "A Scintillation Proximity Assay for UDP-GalNAc:Polypeptide, *N*-Acetylgalactosaminyltransferase", *Anal. Biochem.*, 239:20-24 (1996).
Bannwarth et al., "Global Phosphorylation Of Peptides Containing Oxidation-Sensitive Amino-Acids", *Bioorganic & Medicinal Chem. Lett.*, 6(17):2141-2146 (1996).
Bartel et al., "Isolation of New Ribozymes from a Large Pool of Random Sequences", *Science*, 261:1411-1418 (1993).
Baumbach et al., "Protein Purification Using Affinity Ligands Deduced from Peptide Libraries", *BioPharm.*, May ed., 24-35 (1992).
Benton et al., "Screening λgt Recombinant Clones by Hybridization to Single Plaques in situ", *Science*, 196:180-182 (1977).
Berg et al., "Long-Chain Polystyrene-Grafted Polyethylene Film Matrix: A New Support for Solid-Phase Peptide Synthesis", *J. Am. Chem. Soc.*, 111:8024-8026 (1989).
Berg et al., Book: "Peptide Synthesis on Polystyrene-Grafted Polyethylene Sheets", *Pept. Proc. 20th Eur. Pept. Symp.*, Jung, G. et al., Eds., pp. 196-198 (1988).
Berg et al., Book: "Polystyrene-Grafted Polyethylene: Design of Film and Felt Matrices for Solid-Phase Peptide Synthesis", *Innovation Perspect. Solid Phase Synth. Collect. Pap.*, Int. Sympl, 1st Epton, Roger, Ed., pp. 453-459 (1990).
Blaney et al., "Computational approaches for combinatorial library design and molecular diversity analysis", *Curr. Opin. Chem. Biol.*, 1:54-59 (1997).
Bock et al., "Selection of single-stranded DNA molecules that bind and inhibit human thrombin", *Nature*, 355:564-566 (1992).
Boehm et al., "The rhombotin family of cysteine-rich LIM-domain oncogenes: Distinct members are involved in T-cell translocations to human chromosomes 11p15 and 11p13", *Proc. Natl. Acad. Sci. U.S.A.*, 88:4367-4371 (1991).
Boesen et al., "Circumvention of chemotherapy-induced myelosuppression by transfer of the *mdr1* gene", *Biotherapy*, 6:291-302 (1994).
Borman, S., "Scientist Refine Understanding Of Protein Folding And Design", *Chem. Eng. News*, 2(12):29-35 (1996).
Boublik et al., "Eukaryotic Virus Display: Engineering the Major Surface Glycoprotein of the *Autographa californica* Nuclear Polyhedrosis Virus (AcNPV) for the Presentation of Foreign Proteins on the Virus Surface", *Bio/Technol.*, 13:1079-1084 (1995).
Brenner et al., "Encoded combinatorial chemistry", *Proc. Natl. Acad. Sci. U.S.A.*, 89:5381-5383 (1992).
Bunin et al., "A General and Expedient Method for the Solid-Phase Synthesis of 1,4-Benzodiazepine Derivatives", *J. Am. Chem. Soc.*, 114:10997-10998 (1992).

Bunin et al., "The combinatorial synthesis and chemical and biological evaluation of a 1,4-benzodiazepine library", *Proc. Natl. Acad. Sci. U.S.A.*, 91:4708-4712 (1994).
*Burger's Medicinal Chemistry and Drug Discovery*, Book: vol. 1: "Principles and Practice", Wolff, M.E., Ed., John Wiley & Sons, Inc. (1995).
Butz et al., "Immunization and Affinity Purification of Antibodies Using Resin-Immobilized Lysine-Branched Synthetic Peptides", *Peptide Res.*, 7(1):20-23 (1994).
Caflisch et al., "Computational combinatorial chemistry for de novo ligand design: Review and assessment", *Perspectives in Drug Discovery and Design*, 3:51-84 (1995).
Chen et al., ""Analogous" Organic Synthesis of Small-Compound Libraries: Validation of Combinatorial Chemistry in Small-Molecule Synthesis", *J. Am. Chem. Soc.*, 116:2661-2662 (1994).
Cheng et al., "Sequence-Selective Peptide Binding with a Peptido-A,B-*trans*-steroidal Receptor Selected from an Encoded Combinatorial Receptor Library", *J. Am. Chem. Soc.*, 118:1813-1814 (1996).
Chu et al., "Using Affinity Capillary Electrophoresis To Identify the Peptide in a Peptide Library that Binds Most Tightly to Vancomycin", *J. Org. Chem.*, 58:648-652 (1993).
Clackson et al., "Making antibody fragments using phage display libraries", *Nature*, 352:624-628 (1991).
*Combinatorial Libraries*, Book: "Synthesis, Screening and Application Potential", Cortese, R., Ed., Water de Gruyter, New York (1996).
Combs et al., "Protein Structure-Based Combinatorial Chemistry: Discovery of Non-Peptide Binding Elements to Src SH3 Domain", *J. Am. Chem. Soc.*, 118:287-288 (1996).
*Current Protocol in Molecular Biology*, Book: vol. 1, Supplement 47, John Wiley & Sons, Inc. (1990).
De Boer et al., "The *tac* promoter: A functional hybrid derived from the *trp* and *lac* promoters", *Proc. Natl. Acad. Sci. USA*, 80:21-25 (1983).
Database EMBL Accession No. AF064819, Oct. 28, 1999, J.C. Lang and D.E. Schuller: "*Homo sapiens* serine protease DESC1 MRNA", XP002166624, abstract.
DATABASE EMBL Accession No. R78581, Jun. 10, 1995, L. Hillier et al.: "yi73c10.r1 Soares placenta Nb2HP *Homo sapiens* cDNA clone", XP002166677, abstract.
DATABASE EMBL Accession No. Y99414, Aug. 8, 2000, "Human PR01461", XP002166625, abstract.
DATABASE EMBL Accession No. AI469095, Mar. 17, 1999, NCI-CGAP: "National Cancer Institute, Cancer Genome Anatomy Project (CGAP), Tumor Gene Index", XP002175686, abstract.
Derwent #002169836 WPI; 1997-357902/33 (citing Japanese Application No., JP09149790-A, published Jun. 10, 1997).
Derwent #002175683 WPI; 1999-551348/46 (citing PCT Application No., WO9946281-A2, published Sep. 16, 1999).
Derwent #002175684 WPI; 1999-551358/46 (citing PCT Application No., WO9946281-A2, published Sep. 16, 1999).
Derwent #002175685 WPI; 1999-551358/46 (citing PCT Application No., WO9946281-A2, published Sep. 16, 1999).
Derwent #002175687 WPI; 1999-551358/46 (citing Application No., WO9946281-A2, published Sep. 16, 1999).
Desai et al., "Tumor Angiogenesis and Endothelial Cell Modulatory Factors", *J. Immunol.*, 22(3):186-211 (1999).
Devlin et al., Random Peptide Libraries: A Source of Specific Protein "Binding Molecules", *Science*, 249:404-406 (1990).
DeWitt et al., "Diversomers:: An approach to nonpeptide, nonoligomeric chemical diversity", *Proc. Natl. Acad. Sci. U.S.A.*, 90:6909-6913 (1993).
Dexter et al., "Conditions Controlling the proliferation of Haemopoietic Stem Cells In Vitro", *J. Cell. Physiol.*, 91:335-344 (1976).
*DNA cloning*, Book: "A practical approach", vol. I, Glover, D.M., Ed., MRL Press Ltd., Oxford, Washington DC (1985).
*Immobilized Biochemical And Affinity Chromatography*, Book: Dunlap, R.B., Ed., Plenum Press, New York (1974).
Ecker et al., "Combinatorial Drug Discovery: Which Methods Will Produce the Greatest Value?", *Bio/Technol.*, 13:351-360 (1995).

Eichler et al., "Identification of Substrate-Analog Trypsin Inhibitors through the Screening of Synthetic Peptide Combinatorial Libraries", *Biochem.*, 32:11035-11041 (1993).

Ellington et al., "In vitro selection of RNA molecules that bind specific ligands", *Nature*, 346:818-822 (1990).

Erickson et al., Book: *The Proteins*, "Solid-Phase Peptide Synthesis", vol. II, Neurath H., Hill. R.L. Eds., Academic Press, New York, pp. 255-257 (1976).

Felici, F., "Selection of Antibody Ligands from a Large Library of Oligopeptides Expressed on a Multivalent Exposition Vector", *J. Mol. Biol.*, 222:301-310 (1991).

Fodor et al., "Light-Directed, Spatially Addressable Parallel Chemical Synthesis", *Science*, 251:767-773 (1991).

Francisco et al., "Transport and anchoring of β-lactamase to the external surface of *Escherichia coli*", *Proc. Natl. Acad. Sci. U.S.A.*, 89:2713-2717 (1992).

Gallop et al., "Applications of Combinatorial Technologies to Drug Discovery. 1. Background and Peptide Combinatorial Libraries", *J. Med. Chem.*, 37(9):1233-1251 (1994).

Gardner et al., "The complete nucleotide sequence of an infectious clone of cauliflower mosaic virus by M13mp7 shotgun sequencing", *Nucleic Acids. Res.*, 9(12):2871-2889 (1981).

Georgiou et al., "Practical applications of engineering Gram-negative bacterial cell surfaces", *TIBTECH*, 11:6-10 (1993).

Geysen et al., "Use of peptide synthesis to probe viral antigens for epitopes to a resolution of a single amino acid", *Proc. Natl. Acad. Sci. USA*, 81:3998-4002 (1984).

Gilbert et al., "Useful Proteins from Recombinant Bacteria", *Sci. Am.*, 242:74-94 (1980).

Glaser et al., "Antibody Engineering by Codon-Based Mutagenesis in a Filamentous Phage Vector System", *J. Immunol.*, 149(12):3903-3913 (1992).

Gonzalez et al., "Voltage Sensing by Fluorescence Resonance Energy Transfer in Single Cells", *Biophys. J.*, 69:1272-1280 (1995).

Gram et al., "In vitro selection and affinity maturation of antibodies from a naive combinatorial immunoglobulin library", *Proc. Natl. Acad. Sci. U.S.A.*, 89:3576-3580 (1992).

Grunstein et al., "Colony hybridization: A method for the isolation of cloned DNAs that contain a specific gene", *Proc. Natl. Acad. Sci. U.S.A.*, 72(10):3961-3965 (1975).

Grosschedl et al., "Introduction of a μ Immunoglobulin Gene into the Mouse Germ Line: Specific Expression in Lymphoid Cells and Synthesis of Functional Antibody", *Cell*, 38:647-658 (1984).

Hamdaoui et al., "Purification of a Novel, Heat-Stable Serine Protease Inhibitor Protein from Ovaries of the Desert Locust, *Schistocerce gregaria*", *Biochem. Biophys. Res. Commun.*, 238(2):357-360 (1997).

Hammer et al., "Diversity of Alpha-Fetoprotein Gene Expression in Mice Is Generated by a Combination of Seperate Enhancer Elements", *Sciene*, 235:53-58 (1987).

Han et al., "Liquid-Phase Combinatorial Synthesis", *Proc. Natl. Acad. Sci. U.S.A.*, 92:6419-6423 (1995).

Hanahan, D., "Heritable formation of pancreatic β-cell tumours in transgenic mice expressing recombinant insulin/simian virus 40 oncogenes", *Nature*, 315:115-122 (1985).

Herrera-Estrella et al., "Expression of chimeric genes transferred into plant cells using a Ti-plasmid-derived vector", *Nature*, 303:209-213 (1984).

Herrera-Estrella et al., "Light-inducible and chloroplast-associates expression of a chimaeric gene introduced into *Nicotiana tabacum* using a Ti plasmid vector", *Nature*, 310:115-120 (1984).

Hoogenboom, et al., "Multi-Subunit Proteins on the Surface of Filamentous Phage: Methologies for Displaying Antibody (Fab) Heavy and Light Chains", *Nucleic Acids Res.*, 19(15):4133-4137 (1991).

Houghten et al., "Generation and use of synthetic peptide combinatorial libraries for basic research and drug discovery", *Nature*, 354:84-86 (1991).

Houghten, et al., "General method for the rapid solid-phase synthesis of large numbers of peptides: specificity of antigen-antibody interaction at the level of individual amino acids", *Proc. Natl. Acad. Sci. U.S.A.*, 82:5131-5135 (1985).

Houghten et al., "The Use of Synthetic Peptide Combinatorial Libraries for the Identification of Bioactive Peptides", *BioTechniques*, 313:412-421 (1992).

Houghten, et al., "The Use of Synthetic Peptide Combinatorial Libraries For The Determination Of Peptide Ligands In Radio-Receptor Assays-Opiod-Peptides", *Bioorg. Med. Chem. Lett.*, 3(3):405-412 (1993).

Hruby et al., "Emerging approaches in the molecular design of receptor-selective peptide ligands: conformational, topographical and dynamic considerations", *Biochem J.*, 268:249-262 (1990).

Huang, et al., "Discovery of new ligand binding pathways in myoglobin by random mutagenesis", *Nature Struct. Biol.*, 1(4):226-229 (1994).

Hunkapiller et al., "A microchemical facility for the analysis and synthesis of genes and proteins", *Nature*, 310:105-111 (1984).

*Immobilized Enzymes, Antigens, Antibodies, and Peptides*, Preparation and Characterization, Weetall, H.H., Ed., Marcel Dekker, Inc., New York, (1975).

IUPAC-IUB, "Commission on Biochemical Nomenclature Abbreviated Nomenclature of Synthetic Polypeptides (Polymerized Amino Acids)", *Biochem.*, 11(5):942-944 (1972).

Jackson et al., "The codependence of angiogenesis and chronic inflammation", *FASEB*, 11:457-465 (1997).

Janda, K.D., "New Strategies for the Design of Catalytic Antibodies", *Biotechnol. Prog.*, 6:178-181 (1990).

Jung et al., "Multiple Peptide Synthesis Methods and Their Applications", *Angew. Chem. Int. Ed. Engl.*, 31(4):367-486 (1992).

Kang et al., "Antibody redesign by chain shuffling from random combinatorial immunoglobulin libraries", *Proc. Natl. Acad. Sci. U.S.A.*, 88:11120-11123 (1991).

Kay et al., An M13 phage library displaying random 38-amino-acid-peptides as a source of novel sequences with affinity to selected targets genes, *Gene*, 128:59-65 (1993).

Kelsey et al., "Species- and tissue-specific expression of human $\alpha_1$-antitrypsin in transgenic mice", *Genes and Devel.*, 1:161-171 (1987).

Kennedy et al., "Immobilized Enzymes", Book: vol. 66, Chapter 7, *Solid Phase Biochemistry. Analytical and Synthetic Aspects*, John Wiley & Sons, Inc., New York, pp. 253-391 (1993).

Kitamoto et al., "Enterokinase, the initiator of intestinal digestion, is a mosaic protease composed of a distinctive assortment of domains", *Proc. Natl. Acad. Sci. U.S.A.*, 91:7588-7592 (1994).

Kleine et al., "Lipopeptide-Polyoxyethylene Conjugated as Mitogens and Adjuvants", *Immunobiol.*, 190:53-66 (1994).

Kodo et al., "Antibody Synthesis by Bone Marrow Cells In Vitro following Primary and Booster Tetanus Toxoid Immunization in Humans", *J. Clin. Invest.*, 73:1377-1384 (1984).

Kollias et al., "Regulated Expression of Human $^A\gamma$-, β-, and Hybrid γβ-Globin Genes in Transgenic Mice: Manipulation of the Development Expression Patterns", *Cell*, 46:89-94 (1986).

Kozarsky et al., "Gene therapy: adenovirus vectors", *Current Opinion in Genetics and Development*, 3:499-503 (1993).

Krumlauf et al., "Development Regulation of α-Fetoprotein Genes in Transgenic Mice", *Mol. Cell. Biol.*, 5(7):1639-1648 (1985).

Lam, K.S., "Application of combinatorial library methods in cancer research and drug discovery", *Anti-Cancer Drug Des.*, 12:145-167 (1997).

Lam et al., A new type of synthetic peptide library for identifying ligand-binding activity, *Nature*, 354:82-84 (1991); (published errata in *Nature*, 358:434 (1992) and *Nature*, 360:768 (1992).

La Vallie et al., "Cloning and Functional Expression of a cDNA Encoding the Catalytic Subunit of Bovine Enterokinase", *J. Biol. Chem.*, 268(31):23311-23327, (1993).

Lebl et al., "One Bead One Structure Combinatorial Libraries", *Biopolymers (Pept. Sci. )*, 37:177-198 (1995).

Leder et al., "Consequences of Widespread Deregulation of the c-*myc* Gene in Transgenic Mice: Multiple Neoplasms and Normal Development", *Cell*, 45:485-495 (1986).

Lee et al., "Activation of Hepatocyte Growth Factor and Urokinase/Plasminogen Activator by Matriptase, an Epithelial Membrane Serine Protease", *J. Biol. Chem.*, 275(47):36720-36725 (2000).

Lerner et al., "Antibodies without Immunization", *Science*, 258:1313-1314 (1992).

Li et al., "Minimization of a Polypeptide Hormone", *Science*, 270:1657-1660 (1995).
Light et al., "Phophabs: Antibody-Phage-Alkaline Phosphatase Conjugates For One Step Elisa''s Without Immunization", *Bioorg. Med. Chem. Lett.*, 2(9):1073-1078 (1992).
Lin et al., "Molecular Cloning of cDNA for Matriptase, a Matrix-degrading Serine Protease with Trypsin-like Activity", *J. Biol. Chem.*, 274(26):18231-18236 (1999).
Little et al., "Bacterial surface presentation of proteins and peptides: an alternative to phage technology?", *Trends Biotechnol.*, 11:3-5 (1993).
Lu et al., "Bovine Proenteropeptidase Is Activated by Trypsin, and the Specificity of Enteropeptidase Depends on the Heavy Chain", *J. Biol. Chem.*, 272(50):31293-31300, (1997).
MacDonald, R.J., "Expression of the Pancreatic Elastase I Gene in Transgenic Mice", *Hepatol.*, Suppl. 7(1):42S-51S (1987).
Madison, E.L., "Substrate Specificity Of Tissue Type Plasminogen Activator", *Chem. Biol. of Serpins*, Plenum Press, New York, pp. 109-1210 (1997).
Magram et al., "Developmental regulation of a cloned adult β-globin gene in transgenic mice", *Nature*, 315:338-340 (1985).
Marks et al., "By-Passing Immunization. Human Antibodies from V-Gene Libraries Displayed on Phage", *J. Mol. Biol.*, 222:581-597 (1991).
Mason et al., "The Hypogonadal Mouse, Reproductive Functions Restored by Gene Therapy", *Science* 234:1372-1378 (1986).
Matthews et al., "Substrate Phage: Selection of Protease Substrates by Monovalent Phage Display", *Sciene*, 260:1113-1117 (1993).
McCafferty et al., "Phage Enzymes: Expression and Affinity Chromatography of Fucntional Alkaline Phosphatase on the Surface of Bacteriophage", *Protein Eng.*, 4(8):955-961 (1991).
Menger et al., "Phosphatase Catalysis Developed Via Combinatorial Organic Chemistry", *J. Org. Chem.*, 60:6666-6667 (1995).
Merrifield, R.B., "Solid Phase Peptide Synthesis. I. The Synthesis of a Tetrapeptide", *J. Am. Chem. Soc.*, 85:2149-2154 (1963).
Merrifield, R.B., "Solid Phase Peptide Synthesis. III. An Improved Synthesis of Bradykinin", *Biochemistry*, 3(9):1385-1390 (1964).
Mignatti et al., "Plasminogen Activators and matrix Metal-loproteinases in Angiogenesis", *Enzyme Protein*, 49(1-3):117-137 (1996).
Mitchell et al., "Preparation of Aminomethyl-Polystyrene Resin By Direct Amidomethylation", *Tetrahedron Lett.*, 42:3795-3798 (1976).
Mitchell et al., "A New Synthetic Route to *tert*-Butyloxycarbonylaminoacyl-4-(oxymethyl)phenylacetamidomethyl-resin, an Improved Support for solid-Phase Peptide Synthesis", *J. Org. Chem.*, 43(14):2845-2852 (1978).
Mosbach, K., "AMP and NAD as "General Ligands"", *Methods in Enzymol.*, 34:229-243 (1974).
Nicolaou et al., "Radiofrequency Encoded Combinatorial Chemistry", *Angew. Chem. Int. Ed. Engl.*, 34(20):2289-2291 (1995).
Nogrady, T., Book: *Medicinal Chemistry A Biochemical Approach*, Oxford University Press, New York, pp. 388-392 (1985).
Norrby, K., "Angiogenesis: new aspects relating to its initiation and control", *APMIS*, 105:417-437 (1997).
Oldenburg et al., "Peptide Ligands for a Sugar-Binding Protein Isolated from a Random Peptide Library", *Proc. Natl. Acad. Sci. U.S.A.*, 89:5393-5397 (1992).
Ornitz et al., "Elastase I Promoter Directs Expression of Human Growth Hormone and SV40 T Antigen Genes to Pancreatic Acinar Cells in Transgenic Mice", *Cold Spring Harbor Symp. Quant. Biol.* 50:399-409 (1986).
Ossowski, L., "In Vivo Invasion of Modified Chorioallantoic Membrane by Tumor Cells: the Role of Cell Surface-bound Urokinase", *J. Cell Biol.* 107(6.1):2437-2445 (1988).
Padwa et al., "Photoelimination of a β-Keto Sulfide with a Low-Lying π—π Triplet State", *J. Org. Chem.*, 36(23):3550-2552 (1971).
Parmley et al., "Antibody-Selectable Filamentous fd Phage Vectors: Affinity Purification of Target Genes", *Genes*, 73:305-318 (1988).
*PCR Protocols*, Book: Chapter 37-38, "Amplification Of Ribosomal RNA Genes For Molecular Evolution Studies" and "Amplification And Direct Sequencing Of Fungal Ribosomal RNA Genes For Phylogenetics", Innis et al., Eds., Academic Press, Inc., San Diego, CA, pp. 307-322 (1990).
*PIERCE Catalog*, ImmunoTechnology Catalog & Handbook, 1992-1993.
Pinilla et al., "Review of the Utility of Soluble Combinatorial Libraries", *Biopolymers*, 37:221-240 (1995).
Pinilla et al., "Synthetic peptide combinatorial libraries (SPCLs)—identification of the antigenic determinant of beta-endorphin recognized by monoclonal antibody-3E7", *Gene*, 128:71-76 (1993).
Pinkert et al., "An albumin enhancer located 10 kb upstream functions along with its promoter to direct efficient, liver-specific expression in transgenic mice", *Genes & Development*, 1:268-276 (1987).
Pistor et al., "Expression of Viral Hemagglutinin On the Surface of *E. coli*.", *Klin. Wochenschr.*, 66:110-116 (1988).
Pittelkow et al., "New Technologies for the In Vitro Culture of Human Skin Keratinocytes and Perspectives on Their Use for Grafting of Patients With Extensive Burns", *Mayo Clinic Proc.*, 61:771-777 (1986).
Pollack et al., "Selective Chemical Catalysis by an Antibody", *Science*, 234:1570-1572 (1986).
Polverini, P.J., "The Pathophysiology Of Angiogenesis", *Crit. Rev. Oral. Biol. Med.*, 6(3):230-247 (1995).
Powers et al., "Proteins Purification by Affinity Binding to Unilamellar Vesicles", *Biotechnol. Bioengineering*, 33:173-182 (1989).
Rao et al., "Partial Characterization of Matrix-Associated Serine Protease Inhibitors from Human Skin Cells", *J. Invest. Dermatol.*, 104(3):379-3831, (1995).
Readhead et al., "Expression of a Myelin Basic Protein Gene in Transgenic Shiverer Mice: Correction of the Dysmyelinating Phenotype", *Cell* 48:703-712 (1987).
*Remington's Pharmaceutical Sciences*, 17th Edition, Gennaro, A.R., Ed., Mack Publishing Company, Easton, Pa. (1985).
Rheinwald, "Serial Cultivation of Normal Human Epidermal Keratinocytes", Chapter 15, *Meth. Cell Biol.*, vol. 21, 21A:229-254 (1980).
Rigler et al., "Fluorescence Correlations, Single Molecule Detection and Large Number Screening: Applications in Biotechnology", *J. Biotehcnol.*, 41:177-186 (1995).
Roberts et al., "Unusual Amino/Acids in Peptides Synthesis", *The Peptides. Analysis, Synthesis, Biology*, Chapter 6, 5:341-449 (1983).
Sambrook et al., "Molecular Cloning", *A Laboratory Manual*, 2d Ed., Cold Spring Harbor Laboratory Press, Cold Spring Harbor, New York (1989).
Sarin et al., "Inhibition of acquired immunodeficiency syndrome virus by oligodeoxynucleoside methylphosphonates", *Proc. Natl. Acad. Sci. U.S.A.* 85:7448-7451 (1988).
Sarvetnick et al., "Increasing the Chemical Potential of the Germ-Line Antibody Repertoire", *Proc. Natl. Acad. Sci. U.S.A.*, 90:4008-4011 (1993).
Sastry et al., "Cloning of the immunological repertiore in *Escherichia coli* for generation of monoclonal catalytic antibodies: Construction of a heavy chain variable region-specific cDNA library", *Proc. Natl. Acad. Sci. U.S.A.*, 86:5728-5732 (1989).
Sato et al., "A matrix metalloproteinase expressed on the surface of invasive tumour cells", *Nature*, 370:61-65 (1994).
Schultz, et al., "The Combinatorial Library: A Multifunctional Resource", *Biotechnol. Prog.*, 12(6):729-743 (1996).
Scott et al., "Searching for Peptide Ligands with an Epitope Library", *Science*, 249:386-390 (1990).
Scott et al., "Random peptide libraries", *Curr. Opin. Biotechnol.*, 5:40-48 (1994).
Sears et al., "Engineering Enzymes for Bioorganic Synthesis: Peptide Bond Formation", *Biotechnol. Prog.*, 12:423-433 (1996).
Senda et al., "Treatment of Ulcerative Colitis with Camostat Mesilate, A Serine Protease Inhibitor", *Intern. Med.*, 32(4):350-354 (1993).
Senter et al., "Novel Photocleavable Protein Crosslinking Reagents And Their Use In The Preparation Of Antibody-Toxin Conjuagtes", *Photochem. Photobiol*, 42(3):231-237 (1985).

Shani, M., "Tissue-specific expression of rat myosin light-chain 2 gene in transgenic", *Nature*, 314:283-286 (1985).
Simon et al., "Peptides: A modular approach to drug discovery", *Proc. Natl. Acad. Sci. U.S.A.*, 89:9367-9371 (1992).
Smith et al., "Single-step purification of polypeptides expressed in *Escherichia coli* as fusions with glutathione S-transferase", *Gene* 67:31-40 (1988).
Stein et al., "Physicochemical properties of phosphorothioate oligodeoxynucleotides", *Nucl. Acids Res.* 16(8):3209-3221 (1988).
Stemple et al., "Isolation of a Stem Cell for Neurons and Glia from the Mammalian Neural Crest", *Cell* 71:973-985 (1992).
Still, W.C, "Discovery of Sequence-Selective Peptide Binding by Synthetic Receptors Using Encoded Combinatorial Libraries", *Acc. Chem. Res.*, 29:155-163 (1996).
Sucholeiki, I., "Solid-Phase Photochemical C-S Bond Cleavage Of Thioethers-A New Approach To The Solid-Phase Production Of Non-Peptide Molecules", *Tetrahedron Lttrs.*, 35:7307-7310 (1994).
Swift et al., "Tissue-Specific Expression of the Rat Pancreatic Elastase I Gene in Transgenic Mice", *Cell* 38:639-646 (1984).
Takeuchi et al., "Reverse biochemistry: Use of macromolecular protease inhibitors to dissect complex biological processes and identify a membrane-type serine protease in epithelial cancer and normal tissue", *Proc. Natl. Acad. Sci. U.S.A.*, 96:11054-11061 (1999).
Takeuchi et al., "Cellular Localization of Membrane-type Serine Protease 1 and Identification of Protease-activated Receptor-2 and Single-chain Urokinase-type Plasminogen Activator as Substrates", *J. Biol. Chem.*, 275(34):26333-26342 (2000).
Thompson et al., "Synthesis and Applications of Small Molecule Libraries", *Chem. Rev.*, 96:555-600 (1996).
Tietze et al., "Domino reactions for library synthesis of small molecules in combinatorial chemistry", *Curr. Opin. Chem. Biol.*, 2(3):363-371 (1998).
Tyle, P., "Iontophoretic Devices for Drug Delivery", *Pharmaceutical Res.*, 3(6):318-326 (1986).
Vassalli et al., "Membrane proteases in focus", *Nature*, 370:14-15 (1994).
Vedejs et al., "A Method for Mild Photochemical Oxidation; Conversion of Phenacyl Sulfides into Carbonyl Compounds", *J. Org. Chem.*, 49:573-575 (1984).
Villa-Komaroff et al., "A bacterial clone synthesizing proinsulin", *Proc. Natl. Acad. Sci. U.S.A.*, 75(8):3727-3731 (1978).
Vu et al., "Identification and Cloning of the Membrane-associated Serine Protease, Hepsin, from Mouse Preimplantation Embryos", *J. Biol. Chem.*, 272(50):31315-31320 (1997).
Wang, S., "Solid Phase Synthesis of Protected Peptides via Photolytic Cleavage of the α-Methylphenacyl Ester Anchoring Linkage", *J. Org. Chem.*, 41(20):3258-3261 (1976).
Weaner et al., "Tritium Labeling Of *N*-Protected Amino Acids and Peptides Containing *O*-Alkyl-Tyrosyl Residues", Paper 22, *Synthesis and Applications of Isotopically Labelled Compounds*, Allen J., Ed., pp. 137-140 (1994).
Whitlock et al., "Long-term culture of B lymphocytes and their precursors from murine bone marrow", *Proc. Natl. Acad. Sci. U.S.A.*, 79:3608-3612 (1982).
Wong, S.S., Book: *Chemistry of Protein Conjugation and Cross Linking*, CRC Press, Inc. (1993).
Wong, S.S., Book: Chapter 12, "Conjugation of Proteins to Solid Matrices", *Chemistry of Protein Conjugation and Cross Linking*, CRC Press, Inc., pp. 295-317 (1993).
Wrighton et al., "Small Peptides a Potent Mimetics of the Protein Hormone Erythropoietin", *Science*, 273:458-464 (1996).
Xu et al., "The Crystal Structure of Bikunin from the Inter-α-Inhibitor Complex: A Serine Protease Inhibitor with Two Kunitz Domains", *J. Mol. Biol.*, 276:955-966 (1998).
Yan et al., "Corin, a Mosaic Transmembrane Serine Protease Encoded by a Novel cDNA from Human Heart", *J. Biol. Chem.*, 274(21):14926-14935 (1999).
Yamaoka et al., "Cloning and Characterization of the cDNA for Human Airway Trypsin-like Protease", *J. Biol. Chem.*, 273(19):11895-11901 (1998).

York et al., "Combinatorial Mutagenesis of the Reactive Site Region in Plasminogen Activator Inhibitor 1", *J. Biol. Chem.*, 266(13):8595-8600 (1991).
Zebedee et al., "Human Combinatorial Antibody Libraries to Hepatitis B Surface Antigen", *Proc. Natl. Acad. Sci. U.S.A.*, 89:3175-3179 (1992).
Ziegler, J., "Angiogensis Research Enjoys Growth Spurt in the 1990s", *J. Nat'l Cancer Institute*, 88(12);786-788 (1996).
Zuckermann et al., "Efficient Method for the Preparation of Peptoids [Oligo(N-substituted glycines)] by Submonomer Solid-Phase Synthesis", *J. Am. Chem. Soc.*, 114:10646-10647 (1992).
Zuckermann et al., "Identification of Highest-Affinity Ligands by Affinity Selection from Equimolar Peptide Mixtures Generated by Robotic Synthesis", *Proc. Natl. Acad. Sci. U.S.A.*, 89:4505-4509 (1992).
Pearson et al. (1997) *Cabios Invited Review* 13(4): 325-32.
*Proteins LabFax*, N.C. Price, editor, Academic Press (1996), Chapter 22 Computer Analysis of Protein Structure 241-252.
Database EMBL, Accession No. W22987, "Human Serine Protease 67", XP002169836 abstract, Oct. 8, 1997; abstract of Japan, 1997(10), Oct. 31, 1997; abstract of Japan 09 149790, Jul. 10, 1997.
Database EMBL, Accession No. AAY41710, "Human PR0618 protein sequence", *Genentech Inc.*, XP002175683 abstract, Dec. 7, 1999; PCT 99 46281 A, *Genentech Inc.*, Sep. 16, 1999.
Database EMBL, Accession No. AAZ34033, "Human PR0618 nucleotide sequence", *Genentech Inc.*, XP002175684 abstract, Dec. 7, 1999; PCT 99 46281 A, *Genentech Inc.*, Sep. 16, 1999.
Database EMBL, Accession No. AAZ33949, "Human PR0382 nucleotide sequence", *Genentech Inc.*, XP002175685 abstract, Dec. 7, 1999; PCT 99 46281 A, *Genentech Inc.*, Sep. 16, 1999.
Database EMBL, Accession No. AAY41694, "Human PR0382 protein sequence", *Genentech Inc.*, XP002175687 abstract, Dec. 7, 1999; PCT 99 46281 A, *Genentech Inc.*, Sep. 16, 1999.
GenBank accession number for nucleotide: AI924527, Strausberg "Airway Trypsin-like Protease" entry created Jul. 1999.
GenBank accession number for nucleotide: AI924182, Strausberg "Airway Trypsin-like Protease" entry created Jul. 1999.
GenBank accession number for nucleotide: AI391417, Marra et al. "Plasma Kallikrein Precursor" entry created Feb 1999.
GenBank accession number for nucleotide: AA208793, Marra et al. "Plasma Kallikrein Precursor" entry created Jan. 1997.
GenBank accession number for nucleotide: AA883068, Strausberg, no title, entry created Mar. 1998.
GenBank accession number for nucleotide: AW591433, Strausberg, no title, entry created Mar. 2000.
GenBank accession number for nucleotide: AI978874, Strausberg, "Transmembrane Protease Serine 2" entry created Aug. 1999.
GenBank accession number for nucleotide: AI469095, Strausberg, "Serine Protease" entry created Mar. 1999.
GenBank accession number for nucleotide: AI935487, Strausberg, no title, entry created Aug. 1999.
GenBank accession number for nucleotide: AI534591, Stapleton, "Drosphila Melanogaster Ribosomal Protein S2", entry created Mar. 1999.
GenBank accession number for nucleotide: AI758271, Strausberg, no title, entry created Jun. 1999.
GenBank accession number for nucleotide: AF133845, Yan et al., "*Homo sapiens* Corin, mRNA", submitted Mar. 1999.
GenBank accession number for nucleotide: AB013874 Tomita et al., "Low Density Lipoprotein Receptor Related Protein 4", submitted May 1998.
GenBank accession number for nucleotide: U09860, Kitamoto et al., "Human Enterokinase mRNA", submitted May 1994.
GenBank accession number for nucleotide: AB002134, Yamaoko, "*Homo sapiens* mRNA for Airway Trypsin-like Protease", submitted Mar. 1997.
GenBank accession number for nucleotide: AF118224, Lin et al., "*Homo sapiens* Matripase mRNA", submitted Jan. 1999.
GenBank accession number for nucleotide: AF133086, Takeuchi et al., "*Homo sapiens* Membrane-type Serine 1 Protease mRNA", submitted Mar. 1999.
GenBank accession number for nucleotide: AF042822, Kim et al., "*Mus musculus* Epithin mRNA", submitted Jan. 1998.

GenBank accession number for nucleotide: AF030065, Vu et al., "*Mus musculus* Serine Protease Hepsin mRNA", submitted Oct. 1997.

GenBank accession number for nucleotide: M18930, Leytus et al., "Human Hepsin mRNA", 1988.

GenBank accession number for nucleotide: X70900, Farley, "*R. norvegicus* mRNA for Hepsin", submitted Jan. 1993.

GenBank accession number for nucleotide: U75329, Paoloni-Giacobino et al., "Human Serine Protease mRNA", submitted 1996.

GenBank accession number for nucleotide: AF113596, Jacquinet et al., "*Mus musculus* Mosiac Serine Protease Epitheliasin mRNA", submitted Dec. 1998.

GenBank accession number for nucleotide: NM_016425, Wallrapp et al., "*Homo sapiens* Transmembrane Protease, Serine 4", 2000.

GenBank accession number for nucleotide: AI909842, Simpson, no title, entry created Dec. 1999.

GenBank accession number for protein: P05981, Tsuji et al., "Serine Protease Hepsin", 1991.

Lee et al., "Activation of hepatocyte growth factor and urokinase/plasminogen activator by matriptase, an epithelial membrane serine protease", *J. Biol. Chem.*, 275(47):36720-36725 (2000).

Thompson, C.B., "Distinct Roles for the Costimulatory Ligands B7-1 and B7-2 in T Helper Cell Differentiation", *Cell*, 81:979-982 (1995).

Database EMBL, Accession No. W22987, "Human Serine Protease 67", XP002169836 abstract, Oct. 8, 1997; abstract of Japan, 1997(10), Oct. 31, 1997; abstract of Japan 09 149790, Jul. 10, 1997.

Database EMBL, Accession No. AAY41710, "Human PR0618 protein sequence", *Genentech Inc.*, XP002175683 abstract, Dec. 7, 1999; PCT 99 46281 A, *Genentech Inc.*, Sep. 16, 1999.

Database EMBL, Accession No. AAZ34033, "Human PR0618 nucleotide sequence", *Genentech Inc.*, XP002175684 abstract, Dec. 7, 1999; PCT 99 46281 A, *Genentech Inc.*, Sep. 16, 1999.

Database EMBL, Accession No. AAZ33949, "Human PR0382 nucleotide sequence", *Genentech Inc.*, XP002175685 abstract, Dec. 7, 1999; PCT 99 46281 A, *Genentech Inc.*, Sep. 16, 1999.

Database EMBL, Accession No. AAY41694, "Human PR0382 protein sequence", *Genentech Inc.*, XP002175687 abstract, Dec. 7, 1999; PCT 99 46281 A, *Genentech Inc.*, Sep. 16, 1999.

Sheau-Ling et al., "Activation of hepatocyte growth factor and urokinase/plasminogen activator by matriptase, an epithelial membrane serine protease", *J. Biol. Chem.*, 275(47):36720-36725 (2000).

Thompson, C.B., "Distinct Roles for the Costimulatory Ligands B7-1 and B7-2 in T Helper Cell Differentiation", *Cell*, 81:979-982 (1995).

\* cited by examiner

Domain organization of MTSP5

MTSP5-L

MTSP5-S

SEQUENCE LISTING

<160> NUMBER OF SEQ ID NOS: 27

<210> SEQ ID NO 1
<211> LENGTH: 702
<212> TYPE: DNA
<213> ORGANISM: Homo sapiens
<220> FEATURE:
<221> NAME/KEY: CDS
<222> LOCATION: (1)..(699)
<220> FEATURE:
<223> OTHER INFORMATION: cDNA encoding protease domain of endotheliase 1

<400> SEQUENCE: 1

```
agg atc gtt ggt ggg aca gaa gta gaa gag ggt gaa tgg ccc tgg cag        48
Arg Ile Val Gly Gly Thr Glu Val Glu Glu Gly Glu Trp Pro Trp Gln
  1               5                  10                  15 gct agc ctg cag tgg gat ggg agt cat cgc tgt gga gca acc tta att        96
Ala Ser Leu Gln Trp Asp Gly Ser His Arg Cys Gly Ala Thr Leu Ile
             20                  25                  30 aat gcc aca tgg ctt gtg agt gct gct cac tgt ttt aca aca tat aag       144
Asn Ala Thr Trp Leu Val Ser Ala Ala His Cys Phe Thr Thr Tyr Lys
         35                  40                  45 aac cct gcc aga tgg act gct tcc ttt gga gta aca ata aaa cct tcg       192
Asn Pro Ala Arg Trp Thr Ala Ser Phe Gly Val Thr Ile Lys Pro Ser
     50                  55                  60
```

```
aaa atg aaa cgg ggt ctc cgg aga ata att gtc cat gaa aaa tac aaa      240
Lys Met Lys Arg Gly Leu Arg Arg Ile Ile Val His Glu Lys Tyr Lys
 65                  70                  75                  80 cac cca tca cat gac tat gat att tct ctt gca gag ctt tct agc cct      288
His Pro Ser His Asp Tyr Asp Ile Ser Leu Ala Glu Leu Ser Ser Pro
                 85                  90                  95 gtt ccc tac aca aat gca gta cat aga gtt tgt ctc cct gat gca tcc      336
Val Pro Tyr Thr Asn Ala Val His Arg Val Cys Leu Pro Asp Ala Ser
            100                 105                 110 tat gag ttt caa cca ggt gat gtg atg ttt gtg aca gga ttt gga gca      384
Tyr Glu Phe Gln Pro Gly Asp Val Met Phe Val Thr Gly Phe Gly Ala
        115                 120                 125 ctg aaa aat gat ggt tac agt caa aat cat ctt cga caa gca cag gtg      432
Leu Lys Asn Asp Gly Tyr Ser Gln Asn His Leu Arg Gln Ala Gln Val
    130                 135                 140 act ctc ata gac gct aca act tgc aat gaa cct caa gct tac aat gac      480
Thr Leu Ile Asp Ala Thr Thr Cys Asn Glu Pro Gln Ala Tyr Asn Asp
145                 150                 155                 160 gcc ata act cct aga atg tta tgt gct ggc tcc tta gaa gga aaa aca      528
Ala Ile Thr Pro Arg Met Leu Cys Ala Gly Ser Leu Glu Gly Lys Thr
                165                 170                 175 gat gca tgc cag ggt gac tct gga gga cca ctg gtt agt tca gat gct      576
Asp Ala Cys Gln Gly Asp Ser Gly Gly Pro Leu Val Ser Ser Asp Ala
            180                 185                 190 aga gat atc tgg tac ctt gct gga ata gtg agc tgg gga gat gaa tgt      624
Arg Asp Ile Trp Tyr Leu Ala Gly Ile Val Ser Trp Gly Asp Glu Cys
        195                 200                 205 gcg aaa ccc aac aag cct ggt gtt tat act aga gtt acg gcc ttg cgg      672
Ala Lys Pro Asn Lys Pro Gly Val Tyr Thr Arg Val Thr Ala Leu Arg
    210                 215                 220 gac tgg att act tca aaa act ggt atc taa                              702
Asp Trp Ile Thr Ser Lys Thr Gly Ile
225                 230

<210> SEQ ID NO 2
<211> LENGTH: 233
<212> TYPE: PRT
<213> ORGANISM: Homo sapiens
<220> FEATURE:
<223> OTHER INFORMATION: protease domain of endotheliase 1

<400> SEQUENCE: 2

Arg Ile Val Gly Gly Thr Glu Val Glu Glu Gly Glu Trp Pro Trp Gln
  1               5                  10                  15

Ala Ser Leu Gln Trp Asp Gly Ser His Arg Cys Gly Ala Thr Leu Ile
                 20                  25                  30

Asn Ala Thr Trp Leu Val Ser Ala Ala His Cys Phe Thr Thr Tyr Lys
             35                  40                  45

Asn Pro Ala Arg Trp Thr Ala Ser Phe Gly Val Thr Ile Lys Pro Ser
         50                  55                  60

Lys Met Lys Arg Gly Leu Arg Arg Ile Ile Val His Glu Lys Tyr Lys
 65                  70                  75                  80

His Pro Ser His Asp Tyr Asp Ile Ser Leu Ala Glu Leu Ser Ser Pro
                 85                  90                  95

Val Pro Tyr Thr Asn Ala Val His Arg Val Cys Leu Pro Asp Ala Ser
            100                 105                 110

Tyr Glu Phe Gln Pro Gly Asp Val Met Phe Val Thr Gly Phe Gly Ala
        115                 120                 125

Leu Lys Asn Asp Gly Tyr Ser Gln Asn His Leu Arg Gln Ala Gln Val
```

```
                130                 135                 140
Thr Leu Ile Asp Ala Thr Thr Cys Asn Glu Pro Gln Ala Tyr Asn Asp
145                 150                 155                 160

Ala Ile Thr Pro Arg Met Leu Cys Ala Gly Ser Leu Glu Gly Lys Thr
                165                 170                 175

Asp Ala Cys Gln Gly Asp Ser Gly Gly Pro Leu Val Ser Ser Asp Ala
            180                 185                 190

Arg Asp Ile Trp Tyr Leu Ala Gly Ile Val Ser Trp Gly Asp Glu Cys
        195                 200                 205

Ala Lys Pro Asn Lys Pro Gly Val Tyr Thr Arg Val Thr Ala Leu Arg
    210                 215                 220

Asp Trp Ile Thr Ser Lys Thr Gly Ile
225                 230

<210> SEQ ID NO 3
<211> LENGTH: 1689
<212> TYPE: DNA
<213> ORGANISM: Homo sapiens
<220> FEATURE:
<221> NAME/KEY: CDS
<222> LOCATION: (1)...(1689)
<223> OTHER INFORMATION: DNA encoding a transmembrane serine protease
      (Endotheliase 2-S) protein

<400> SEQUENCE: 3 atg gag agg gac agc cac ggg aat gca tct cca gca aga aca cct tca      48
Met Glu Arg Asp Ser His Gly Asn Ala Ser Pro Ala Arg Thr Pro Ser
1               5                   10                  15 gct gga gca tct cca gcc cag gca tct cca gct ggg aca cct cca ggc      96
Ala Gly Ala Ser Pro Ala Gln Ala Ser Pro Ala Gly Thr Pro Pro Gly
            20                  25                  30 cgg gca tct cca gcc cag gca tct cca gcc cag gca tct cca gct ggg     144
Arg Ala Ser Pro Ala Gln Ala Ser Pro Ala Gln Ala Ser Pro Ala Gly
        35                  40                  45 aca cct ccg ggc cgg gca tct cca gcc cag gca tct cca gct ggt aca     192
Thr Pro Pro Gly Arg Ala Ser Pro Ala Gln Ala Ser Pro Ala Gly Thr
    50                  55                  60 cct cca ggc cgg gca tct cca ggc cgg gca tct cca gcc cag gca tct     240
Pro Pro Gly Arg Ala Ser Pro Gly Arg Ala Ser Pro Ala Gln Ala Ser
65                  70                  75                  80 cca gcc cgg gca tct ccg gct ctg gca tca ctt tcc agg tcc tca tcc     288
Pro Ala Arg Ala Ser Pro Ala Leu Ala Ser Leu Ser Arg Ser Ser Ser
                85                  90                  95 ggc agg tca tca tcc gcc agg tca gcc tcg gtg aca acc tcc cca acc     336
Gly Arg Ser Ser Ser Ala Arg Ser Ala Ser Val Thr Thr Ser Pro Thr
            100                 105                 110 aga gtg tac ctt gtt aga gca aca cca gtg ggg gct gta ccc atc cga     384
Arg Val Tyr Leu Val Arg Ala Thr Pro Val Gly Ala Val Pro Ile Arg
        115                 120                 125 tca tct cct gcc agg tca gca cca gca acc agg gcc acc agg gag agc     432
Ser Ser Pro Ala Arg Ser Ala Pro Ala Thr Arg Ala Thr Arg Glu Ser
    130                 135                 140 cca ggt acg agc ctg ccc aag ttc acc tgg cgg gag ggc cag aag cag     480
Pro Gly Thr Ser Leu Pro Lys Phe Thr Trp Arg Glu Gly Gln Lys Gln
145                 150                 155                 160 cta ccg ctc atc ggg tgc gtg ctc ctc ctc att gcc ctg gtg gtt tcg     528
Leu Pro Leu Ile Gly Cys Val Leu Leu Leu Ile Ala Leu Val Val Ser
                165                 170                 175 ctc atc atc ctc ttc cag ttc tgg cag ggc cac aca ggg atc agg tac     576
Leu Ile Ile Leu Phe Gln Phe Trp Gln Gly His Thr Gly Ile Arg Tyr
```

-continued

|  |  |  |  |  |  |  |  |  |  |  |  |  |  |  |  |
|---|---|---|---|---|---|---|---|---|---|---|---|---|---|---|---|
|  |  |  | 180 |  |  |  |  | 185 |  |  |  |  | 190 |  |  |

```
aag gag cag agg gag agc tgt ccc aag cac gct gtt cgc tgt gac ggg    624
Lys Glu Gln Arg Glu Ser Cys Pro Lys His Ala Val Arg Cys Asp Gly
            195                 200                 205 gtg gtg gac tgc aag ctg aag agt gac gag ctg ggc tgc gtg agg ttt    672
Val Val Asp Cys Lys Leu Lys Ser Asp Glu Leu Gly Cys Val Arg Phe
    210                 215                 220 gac tgg gac aag tct ctg ctt aaa atc tac tct ggg tcc tcc cat cag    720
Asp Trp Asp Lys Ser Leu Leu Lys Ile Tyr Ser Gly Ser Ser His Gln
225                 230                 235                 240 tgg ctt ccc atc tgt agc agc aac tgg aat gac tcc tac tca gag aag    768
Trp Leu Pro Ile Cys Ser Ser Asn Trp Asn Asp Ser Tyr Ser Glu Lys
                245                 250                 255 acc tgc cag cag ctg ggt ttc gag agt gct cac cgg aca acc gag gtt    816
Thr Cys Gln Gln Leu Gly Phe Glu Ser Ala His Arg Thr Thr Glu Val
            260                 265                 270 gcc cac agg gat ttt gcc aac agc ttc tca atc ttg aga tac aac tcc    864
Ala His Arg Asp Phe Ala Asn Ser Phe Ser Ile Leu Arg Tyr Asn Ser
        275                 280                 285 acc atc cag gaa agc ctc cac agg tct gaa tgc cct tcc cag cgg tat    912
Thr Ile Gln Glu Ser Leu His Arg Ser Glu Cys Pro Ser Gln Arg Tyr
    290                 295                 300 atc tcc ctc cag tgt tcc cac tgc gga ctg agg gcc atg acc ggg cgg    960
Ile Ser Leu Gln Cys Ser His Cys Gly Leu Arg Ala Met Thr Gly Arg
305                 310                 315                 320 atc gtg gga ggg gcg ctg gcc tcg gat agc aag tgg cct tgg caa gtg    1008
Ile Val Gly Gly Ala Leu Ala Ser Asp Ser Lys Trp Pro Trp Gln Val
                325                 330                 335 agt ctg cac ttc ggc acc acc cac atc tgt gga ggc acg ctc att gac    1056
Ser Leu His Phe Gly Thr Thr His Ile Cys Gly Gly Thr Leu Ile Asp
            340                 345                 350 gcc cag tgg gtg ctc act gcc gcc cac tgc ttc ttc gtg acc cgg gag    1104
Ala Gln Trp Val Leu Thr Ala Ala His Cys Phe Phe Val Thr Arg Glu
        355                 360                 365 aag gtc ctg gag ggc tgg aag gtg tac gcg ggc acc agc aac ctg cac    1152
Lys Val Leu Glu Gly Trp Lys Val Tyr Ala Gly Thr Ser Asn Leu His
    370                 375                 380 cag ttg cct gag gca gcc tcc att gcc gag atc atc atc aac agc aat    1200
Gln Leu Pro Glu Ala Ala Ser Ile Ala Glu Ile Ile Ile Asn Ser Asn
385                 390                 395                 400 tac acc gat gag gag gac gac tat gac atc gcc ctc atg cgg ctg tcc    1248
Tyr Thr Asp Glu Glu Asp Asp Tyr Asp Ile Ala Leu Met Arg Leu Ser
                405                 410                 415 aag ccc ctg acc ctg tcc gct cac atc cac cct gct tgc ctc ccc atg    1296
Lys Pro Leu Thr Leu Ser Ala His Ile His Pro Ala Cys Leu Pro Met
            420                 425                 430 cat gga cag acc ttt agc ctc aat gag acc tgc tgg atc aca ggc ttt    1344
His Gly Gln Thr Phe Ser Leu Asn Glu Thr Cys Trp Ile Thr Gly Phe
        435                 440                 445 ggc aag acc agg gag aca gat gac aag aca tcc ccc ttc ctc cgg gag    1392
Gly Lys Thr Arg Glu Thr Asp Asp Lys Thr Ser Pro Phe Leu Arg Glu
    450                 455                 460 gtg cag gtc aat ctc atc gac ttc aag aaa tgc aat gac tac ttg gtc    1440
Val Gln Val Asn Leu Ile Asp Phe Lys Lys Cys Asn Asp Tyr Leu Val
465                 470                 475                 480 tat gac agt tac ctt acc cca agg atg atg tgt gct ggg gac ctt cgt    1488
Tyr Asp Ser Tyr Leu Thr Pro Arg Met Met Cys Ala Gly Asp Leu Arg
                485                 490                 495 ggg ggc aga gac tcc tgc cag gga gac agc ggg ggg cct ctt gtc tgt    1536
```

```
Gly Gly Arg Asp Ser Cys Gln Gly Asp Ser Gly Gly Pro Leu Val Cys
            500                 505                 510 gag cag aac aac cgc tgg tac ctg gca ggt gtc acc agc tgg ggc aca      1584
Glu Gln Asn Asn Arg Trp Tyr Leu Ala Gly Val Thr Ser Trp Gly Thr
            515                 520                 525 ggc tgt ggc cag aga aac aaa cct ggt gtg tac acc aaa gtg aca gaa      1632
Gly Cys Gly Gln Arg Asn Lys Pro Gly Val Tyr Thr Lys Val Thr Glu
        530                 535                 540 gtt ctt ccc tgg att tac agc aag atg gag agc gag gtg cga ttc ata      1680
Val Leu Pro Trp Ile Tyr Ser Lys Met Glu Ser Glu Val Arg Phe Ile
545                 550                 555                 560 aaa tcc taa                                                          1689
Lys Ser <210> SEQ ID NO 4
<211> LENGTH: 562
<212> TYPE: PRT
<213> ORGANISM: Homo sapiens
<220> FEATURE:
<221> NAME/KEY: protease domain
<222> LOCATION: (321)..(562)

<400> SEQUENCE: 4

Met Glu Arg Asp Ser His Gly Asn Ala Ser Pro Ala Arg Thr Pro Ser
 1               5                  10                  15

Ala Gly Ala Ser Pro Ala Gln Ala Ser Pro Ala Gly Thr Pro Pro Gly
            20                  25                  30

Arg Ala Ser Pro Ala Gln Ala Ser Pro Ala Gln Ala Ser Pro Ala Gly
        35                  40                  45

Thr Pro Pro Gly Arg Ala Ser Pro Ala Gln Ala Ser Pro Ala Gly Thr
 50                  55                  60

Pro Pro Gly Arg Ala Ser Pro Gly Arg Ala Ser Pro Ala Gln Ala Ser
 65                  70                  75                  80

Pro Ala Arg Ala Ser Pro Ala Leu Ala Ser Leu Ser Arg Ser Ser Ser
                85                  90                  95

Gly Arg Ser Ser Ala Arg Ser Ala Ser Val Thr Thr Ser Pro Thr
                100                 105                 110

Arg Val Tyr Leu Val Arg Ala Thr Pro Val Gly Ala Val Pro Ile Arg
            115                 120                 125

Ser Ser Pro Ala Arg Ser Ala Pro Ala Thr Arg Ala Thr Arg Glu Ser
        130                 135                 140

Pro Gly Thr Ser Leu Pro Lys Phe Thr Trp Arg Glu Gly Gln Lys Gln
145                 150                 155                 160

Leu Pro Leu Ile Gly Cys Val Leu Leu Ile Ala Leu Val Val Ser
                165                 170                 175

Leu Ile Ile Leu Phe Gln Phe Trp Gln Gly His Thr Gly Ile Arg Tyr
            180                 185                 190

Lys Glu Gln Arg Glu Ser Cys Pro Lys His Ala Val Arg Cys Asp Gly
        195                 200                 205

Val Val Asp Cys Lys Leu Lys Ser Asp Glu Leu Gly Cys Val Arg Phe
    210                 215                 220

Asp Trp Asp Lys Ser Leu Leu Lys Ile Tyr Ser Gly Ser Ser His Gln
225                 230                 235                 240

Trp Leu Pro Ile Cys Ser Ser Asn Trp Asn Asp Ser Tyr Ser Glu Lys
                245                 250                 255

Thr Cys Gln Gln Leu Gly Phe Glu Ser Ala His Arg Thr Thr Glu Val
            260                 265                 270
```

-continued

```
Ala His Arg Asp Phe Ala Asn Ser Phe Ser Ile Leu Arg Tyr Asn Ser
            275                 280                 285

Thr Ile Gln Glu Ser Leu His Arg Ser Glu Cys Pro Ser Gln Arg Tyr
        290                 295                 300

Ile Ser Leu Gln Cys Ser His Cys Gly Leu Arg Ala Met Thr Gly Arg
305                 310                 315                 320

Ile Val Gly Gly Ala Leu Ala Ser Asp Ser Lys Trp Pro Trp Gln Val
                325                 330                 335

Ser Leu His Phe Gly Thr Thr His Ile Cys Gly Gly Thr Leu Ile Asp
            340                 345                 350

Ala Gln Trp Val Leu Thr Ala Ala His Cys Phe Phe Val Thr Arg Glu
        355                 360                 365

Lys Val Leu Glu Gly Trp Lys Val Tyr Ala Gly Thr Ser Asn Leu His
    370                 375                 380

Gln Leu Pro Glu Ala Ala Ser Ile Ala Glu Ile Ile Asn Ser Asn
385                 390                 395                 400

Tyr Thr Asp Glu Glu Asp Asp Tyr Asp Ile Ala Leu Met Arg Leu Ser
                405                 410                 415

Lys Pro Leu Thr Leu Ser Ala His Ile His Pro Ala Cys Leu Pro Met
            420                 425                 430

His Gly Gln Thr Phe Ser Leu Asn Glu Thr Cys Trp Ile Thr Gly Phe
        435                 440                 445

Gly Lys Thr Arg Glu Thr Asp Asp Lys Thr Ser Pro Phe Leu Arg Glu
    450                 455                 460

Val Gln Val Asn Leu Ile Asp Phe Lys Lys Cys Asn Asp Tyr Leu Val
465                 470                 475                 480

Tyr Asp Ser Tyr Leu Thr Pro Arg Met Met Cys Ala Gly Asp Leu Arg
                485                 490                 495

Gly Gly Arg Asp Ser Cys Gln Gly Asp Ser Gly Gly Pro Leu Val Cys
            500                 505                 510

Glu Gln Asn Asn Arg Trp Tyr Leu Ala Gly Val Thr Ser Trp Gly Thr
        515                 520                 525

Gly Cys Gly Gln Arg Asn Lys Pro Gly Val Tyr Thr Lys Val Thr Glu
    530                 535                 540

Val Leu Pro Trp Ile Tyr Ser Lys Met Glu Ser Glu Val Arg Phe Ile
545                 550                 555                 560

Lys Ser

<210> SEQ ID NO 5
<211> LENGTH: 2067
<212> TYPE: DNA
<213> ORGANISM: Homo sapiens
<220> FEATURE:
<221> NAME/KEY: CDS
<222> LOCATION: (1)...(2067)
<223> OTHER INFORMATION: DNA sequence encoding a transmembrane serine
      protease (endotheliase-L) protein

<400> SEQUENCE: 5 atg gag agg gac agc cac ggg aat gca tct cca gca aga aca cct tca    48
Met Glu Arg Asp Ser His Gly Asn Ala Ser Pro Ala Arg Thr Pro Ser
1               5                   10                  15 gct gga gca tct cca gcc cag gca tct cca gct ggg aca cct cca ggc    96
Ala Gly Ala Ser Pro Ala Gln Ala Ser Pro Ala Gly Thr Pro Pro Gly
            20                  25                  30 cgg gca tct cca gcc cag gca tct cca gcc cag gca tct cca gct ggg   144
```

```
                                                     -continued

Arg Ala Ser Pro Ala Gln Ala Ser Pro Ala Gln Ala Ser Pro Ala Gly
         35                   40                  45 aca cct ccg ggc cgg gca tct cca gcc cag gca tct cca gct ggt aca     192
Thr Pro Pro Gly Arg Ala Ser Pro Ala Gln Ala Ser Pro Ala Gly Thr
 50                   55                  60 cct cca ggc cgg gca tct cca ggc cgg gca tct cca gcc cag gca tct     240
Pro Pro Gly Arg Ala Ser Pro Gly Arg Ala Ser Pro Ala Gln Ala Ser
 65                   70                  75                  80 cca gcc cgg gca tct ccg gct ctg gca tca ctt tcc agg tcc tca tcc     288
Pro Ala Arg Ala Ser Pro Ala Leu Ala Ser Leu Ser Arg Ser Ser Ser
                      85                  90                  95 ggc agg tca tca tcc gcc agg tca gcc tcg gtg aca acc tcc cca acc     336
Gly Arg Ser Ser Ser Ala Arg Ser Ala Ser Val Thr Thr Ser Pro Thr
                 100                 105                 110 aga gtg tac ctt gtt aga gca aca cca gtg ggg gct gta ccc atc cga     384
Arg Val Tyr Leu Val Arg Ala Thr Pro Val Gly Ala Val Pro Ile Arg
             115                 120                 125 tca tct cct gcc agg tca gca cca gca acc agg gcc acc agg gag agc     432
Ser Ser Pro Ala Arg Ser Ala Pro Ala Thr Arg Ala Thr Arg Glu Ser
         130                 135                 140 cca ggt acg agc ctg ccc aag ttc acc tgg cgg gag ggc cag aag cag     480
Pro Gly Thr Ser Leu Pro Lys Phe Thr Trp Arg Glu Gly Gln Lys Gln
145                 150                 155                 160 cta ccg ctc atc ggg tgc gtg ctc ctc ctc att gcc ctg gtg gtt tcg     528
Leu Pro Leu Ile Gly Cys Val Leu Leu Leu Ile Ala Leu Val Val Ser
                 165                 170                 175 ctc atc atc ctc ttc cag ttc tgg cag ggc cac aca ggg atc agg tac     576
Leu Ile Ile Leu Phe Gln Phe Trp Gln Gly His Thr Gly Ile Arg Tyr
             180                 185                 190 aag gag cag agg gag agc tgt ccc aag cac gct gtt cgc tgt gac ggg     624
Lys Glu Gln Arg Glu Ser Cys Pro Lys His Ala Val Arg Cys Asp Gly
         195                 200                 205 gtg gtg gac tgc aag ctg aag agt gac gag ctg ggc tgc gtg agg ttt     672
Val Val Asp Cys Lys Leu Lys Ser Asp Glu Leu Gly Cys Val Arg Phe
210                 215                 220 gac tgg gac aag tct ctg ctt aaa atc tac tct ggg tcc tcc cat cag     720
Asp Trp Asp Lys Ser Leu Leu Lys Ile Tyr Ser Gly Ser Ser His Gln
225                 230                 235                 240 tgg ctt ccc atc tgt agc agc aac tgg aat gac tcc tac tca gag aag     768
Trp Leu Pro Ile Cys Ser Ser Asn Trp Asn Asp Ser Tyr Ser Glu Lys
                 245                 250                 255 acc tgc cag cag ctg ggt ttc gag agt gct cac cgg aca acc gag gtt     816
Thr Cys Gln Gln Leu Gly Phe Glu Ser Ala His Arg Thr Thr Glu Val
             260                 265                 270 gcc cac agg gat ttt gcc aac agc ttc tca atc ttg aga tac aac tcc     864
Ala His Arg Asp Phe Ala Asn Ser Phe Ser Ile Leu Arg Tyr Asn Ser
         275                 280                 285 acc atc cag gaa agc ctc cac agg tct gaa tgc cct tcc cag cgg tat     912
Thr Ile Gln Glu Ser Leu His Arg Ser Glu Cys Pro Ser Gln Arg Tyr
     290                 295                 300 atc tcc ctc cag tgt tcc cac tgc gga ctg agg gcc atg acc ggg cgg     960
Ile Ser Leu Gln Cys Ser His Cys Gly Leu Arg Ala Met Thr Gly Arg
305                 310                 315                 320 atc gtg gga ggg gcg ctg gcc tcg gat agc aag tgg cct tgg caa gtg    1008
Ile Val Gly Gly Ala Leu Ala Ser Asp Ser Lys Trp Pro Trp Gln Val
                 325                 330                 335 agt ctg cac ttc ggc acc acc cac atc tgt gga ggc acg ctc att gac    1056
Ser Leu His Phe Gly Thr Thr His Ile Cys Gly Gly Thr Leu Ile Asp
             340                 345                 350
```

```
gcc cag tgg gtg ctc act gcc gcc cac tgc ttc ttc gtg acc cgg gag      1104
Ala Gln Trp Val Leu Thr Ala Ala His Cys Phe Phe Val Thr Arg Glu
        355                 360                 365 aag gtc ctg gag ggc tgg aag gtg tac gcg ggc acc agc aac ctg cac      1152
Lys Val Leu Glu Gly Trp Lys Val Tyr Ala Gly Thr Ser Asn Leu His
    370                 375                 380 cag ttg cct gag gca gcc tcc att gcc gag atc atc atc aac agc aat      1200
Gln Leu Pro Glu Ala Ala Ser Ile Ala Glu Ile Ile Ile Asn Ser Asn
385                 390                 395                 400 tac acc gat gag gag gac gac tat gac atc gcc ctc atg cgg ctg tcc      1248
Tyr Thr Asp Glu Glu Asp Asp Tyr Asp Ile Ala Leu Met Arg Leu Ser
                405                 410                 415 aag ccc ctg acc ctg tcc gct cac atc cac cct gct tgc ctc ccc atg      1296
Lys Pro Leu Thr Leu Ser Ala His Ile His Pro Ala Cys Leu Pro Met
        420                 425                 430 cat gga cag acc ttt agc ctc aat gag acc tgc tgg atc aca ggc ttt      1344
His Gly Gln Thr Phe Ser Leu Asn Glu Thr Cys Trp Ile Thr Gly Phe
    435                 440                 445 ggc aag acc agg gag aca gat gac aag aca tcc ccc ttc ctc cgg gag      1392
Gly Lys Thr Arg Glu Thr Asp Asp Lys Thr Ser Pro Phe Leu Arg Glu
450                 455                 460 gtg cag gtc aat ctc atc gac ttc aag aaa tgc aat gac tac ttg gtc      1440
Val Gln Val Asn Leu Ile Asp Phe Lys Lys Cys Asn Asp Tyr Leu Val
465                 470                 475                 480 tat gac agt tac ctt acc cca agg atg atg tgt gct ggg gac ctt cgt      1488
Tyr Asp Ser Tyr Leu Thr Pro Arg Met Met Cys Ala Gly Asp Leu Arg
                485                 490                 495 ggg ggc aga gac tcc tgc cag gga gac agc ggg ggg cct ctt gtc tgt      1536
Gly Gly Arg Asp Ser Cys Gln Gly Asp Ser Gly Gly Pro Leu Val Cys
                500                 505                 510 gag cag aac aac cgc tgg tac ctg gca ggt gtc acc agc tgg ggc aca      1584
Glu Gln Asn Asn Arg Trp Tyr Leu Ala Gly Val Thr Ser Trp Gly Thr
        515                 520                 525 ggc tgt ggc cag aga aac aaa cct ggt gtg tac acc aaa gtg aca gaa      1632
Gly Cys Gly Gln Arg Asn Lys Pro Gly Val Tyr Thr Lys Val Thr Glu
    530                 535                 540 gtt ctt ccc tgg att tac agc aag atg gag aac aga gct cag cgg gtt      1680
Val Leu Pro Trp Ile Tyr Ser Lys Met Glu Asn Arg Ala Gln Arg Val
545                 550                 555                 560 gaa aaa gcg tgg acc tac agg cca ggc agg cag ttg ctg ggc aga tgt      1728
Glu Lys Ala Trp Thr Tyr Arg Pro Gly Arg Gln Leu Leu Gly Arg Cys
                565                 570                 575 tct ccc aga agt att ttt ttg tgt aag gtt gca atg gac ttt gaa aac      1776
Ser Pro Arg Ser Ile Phe Leu Cys Lys Val Ala Met Asp Phe Glu Asn
                580                 585                 590 gtt tca gtt tct gca gag gat ttt gtg ata gtt ttt gtt atc aag cat      1824
Val Ser Val Ser Ala Glu Asp Phe Val Ile Val Phe Val Ile Lys His
            595                 600                 605 tta tgc atg gga atc cgc tct tca tgg cct ttc cca gct ctg ttt gtt      1872
Leu Cys Met Gly Ile Arg Ser Ser Trp Pro Phe Pro Ala Leu Phe Val
        610                 615                 620 tta gtc ttt ttg att ttc ttt ttg ttg ttg tct ttt tta aaa              1920
Leu Val Phe Leu Ile Phe Phe Leu Leu Leu Ser Phe Leu Lys
625                 630                 635                 640 aac aca agt gac tcc att ttg act ctg aca act ttc aca gct gtc acc      1968
Asn Thr Ser Asp Ser Ile Leu Thr Leu Thr Thr Phe Thr Ala Val Thr
                645                 650                 655 aga atg ctc cct gag aac tac cat tct ttc cct ttc cca ctt aaa ata      2016
Arg Met Leu Pro Glu Asn Tyr His Ser Phe Pro Phe Pro Leu Lys Ile
        660                 665                 670
```

```
                                                            -continued ttt cat cag aac ctc act act atc ata aaa gag tat aaa gta ata aaa      2064
Phe His Gln Asn Leu Thr Thr Ile Ile Lys Glu Tyr Lys Val Ile Lys
        675                 680                 685 taa                                                                  2067

<210> SEQ ID NO 6
<211> LENGTH: 688
<212> TYPE: PRT
<213> ORGANISM: Homo sapiens
<220> FEATURE:
<221> NAME/KEY: protease domain
<222> LOCATION: (321)..(688)

<400> SEQUENCE: 6

Met Glu Arg Asp Ser His Gly Asn Ala Ser Pro Ala Arg Thr Pro Ser
 1               5                  10                  15

Ala Gly Ala Ser Pro Ala Gln Ala Ser Pro Ala Gly Thr Pro Pro Gly
             20                  25                  30

Arg Ala Ser Pro Ala Gln Ala Ser Pro Ala Gln Ala Ser Pro Ala Gly
         35                  40                  45

Thr Pro Pro Gly Arg Ala Ser Pro Ala Gln Ala Ser Pro Ala Gly Thr
     50                  55                  60

Pro Pro Gly Arg Ala Ser Pro Gly Arg Ala Ser Pro Ala Gln Ala Ser
 65                  70                  75                  80

Pro Ala Arg Ala Ser Pro Ala Leu Ala Ser Leu Ser Arg Ser Ser Ser
                 85                  90                  95

Gly Arg Ser Ser Ala Arg Ser Ala Ser Val Thr Thr Ser Pro Thr
                100                 105                 110

Arg Val Tyr Leu Val Arg Ala Thr Pro Val Gly Ala Val Pro Ile Arg
            115                 120                 125

Ser Ser Pro Ala Arg Ser Ala Pro Ala Thr Arg Ala Thr Arg Glu Ser
        130                 135                 140

Pro Gly Thr Ser Leu Pro Lys Phe Thr Trp Arg Glu Gly Gln Lys Gln
145                 150                 155                 160

Leu Pro Leu Ile Gly Cys Val Leu Leu Leu Ile Ala Leu Val Val Ser
                165                 170                 175

Leu Ile Ile Leu Phe Gln Phe Trp Gln Gly His Thr Gly Ile Arg Tyr
            180                 185                 190

Lys Glu Gln Arg Glu Ser Cys Pro Lys His Ala Val Arg Cys Asp Gly
        195                 200                 205

Val Val Asp Cys Lys Leu Lys Ser Asp Glu Leu Gly Cys Val Arg Phe
    210                 215                 220

Asp Trp Asp Lys Ser Leu Leu Lys Ile Tyr Ser Gly Ser Ser His Gln
225                 230                 235                 240

Trp Leu Pro Ile Cys Ser Ser Asn Trp Asn Asp Ser Tyr Ser Glu Lys
                245                 250                 255

Thr Cys Gln Gln Leu Gly Phe Glu Ser Ala His Arg Thr Thr Glu Val
            260                 265                 270

Ala His Arg Asp Phe Ala Asn Ser Phe Ser Ile Leu Arg Tyr Asn Ser
        275                 280                 285

Thr Ile Gln Glu Ser Leu His Arg Ser Glu Cys Pro Ser Gln Arg Tyr
    290                 295                 300

Ile Ser Leu Gln Cys Ser His Cys Gly Leu Arg Ala Met Thr Gly Arg
305                 310                 315                 320

Ile Val Gly Gly Ala Leu Ala Ser Asp Ser Lys Trp Pro Trp Gln Val
```

-continued

```
                325                 330                 335
Ser Leu His Phe Gly Thr Thr His Ile Cys Gly Gly Thr Leu Ile Asp
            340                 345                 350
Ala Gln Trp Val Leu Thr Ala Ala His Cys Phe Phe Val Thr Arg Glu
            355                 360                 365
Lys Val Leu Glu Gly Trp Lys Val Tyr Ala Gly Thr Ser Asn Leu His
            370                 375                 380
Gln Leu Pro Glu Ala Ala Ser Ile Ala Glu Ile Ile Asn Ser Asn
385                 390                 395                 400
Tyr Thr Asp Glu Glu Asp Asp Tyr Asp Ile Ala Leu Met Arg Leu Ser
                405                 410                 415
Lys Pro Leu Thr Leu Ser Ala His Ile His Pro Ala Cys Leu Pro Met
            420                 425                 430
His Gly Gln Thr Phe Ser Leu Asn Glu Thr Cys Trp Ile Thr Gly Phe
            435                 440                 445
Gly Lys Thr Arg Glu Thr Asp Asp Lys Thr Ser Pro Phe Leu Arg Glu
            450                 455                 460
Val Gln Val Asn Leu Ile Asp Phe Lys Lys Cys Asn Asp Tyr Leu Val
465                 470                 475                 480
Tyr Asp Ser Tyr Leu Thr Pro Arg Met Met Cys Ala Gly Asp Leu Arg
                485                 490                 495
Gly Gly Arg Asp Ser Cys Gln Gly Asp Ser Gly Gly Pro Leu Val Cys
            500                 505                 510
Glu Gln Asn Asn Arg Trp Tyr Leu Ala Gly Val Thr Ser Trp Gly Thr
            515                 520                 525
Gly Cys Gly Gln Arg Asn Lys Pro Gly Val Tyr Thr Lys Val Thr Glu
            530                 535                 540
Val Leu Pro Trp Ile Tyr Ser Lys Met Glu Asn Arg Ala Gln Arg Val
545                 550                 555                 560
Glu Lys Ala Trp Thr Tyr Arg Pro Gly Arg Gln Leu Leu Gly Arg Cys
                565                 570                 575
Ser Pro Arg Ser Ile Phe Leu Cys Lys Val Ala Met Asp Phe Glu Asn
            580                 585                 590
Val Ser Val Ser Ala Glu Asp Phe Val Ile Val Phe Val Ile Lys His
            595                 600                 605
Leu Cys Met Gly Ile Arg Ser Ser Trp Pro Phe Pro Ala Leu Phe Val
            610                 615                 620
Leu Val Phe Leu Ile Phe Phe Leu Leu Leu Leu Ser Phe Leu Lys
625                 630                 635                 640
Asn Thr Ser Asp Ser Ile Leu Thr Leu Thr Thr Phe Thr Ala Val Thr
                645                 650                 655
Arg Met Leu Pro Glu Asn Tyr His Ser Phe Pro Phe Pro Leu Lys Ile
            660                 665                 670
Phe His Gln Asn Leu Thr Thr Ile Ile Lys Glu Tyr Lys Val Ile Lys
            675                 680                 685
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
       Oligonucleotide primer

<400> SEQUENCE: 7
cctgccagat ggactgcttc ctttg                                              25

<210> SEQ ID NO 8
<211> LENGTH: 27
<212> TYPE: DNA
<213> ORGANISM: Artificial Sequence
<220> FEATURE:
<223> OTHER INFORMATION: Anti-sense primer

<400> SEQUENCE: 8
ggcatgcatc tgtttttcct tctaagg                                            27

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide primer
<220> FEATURE:
<223> OTHER INFORMATION: R= A,G; V= G,A,C; W=A,T; S=G,C; Y= C,T;
      H= A,T,C; N= Inosine

<400> SEQUENCE: 9
tggrtnvtnw sngcnrcnca ytg                                                23

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer
<220> FEATURE:
<223> OTHER INFORMATION: R= A,G; V= G,A,C; W=A,T; S=G,C; Y= C,T;
      H= A,T,C; N= Inosine

<400> SEQUENCE: 10
ggnccnccns wrtcnccytn rcanghrtc                                          29

<210> SEQ ID NO 11
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 11
ggaggcaagc agggtggatg tgagcggac                                          29

<210> SEQ ID NO 12
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 12
cggatcgtgg gaggggcgct ggcctc                                             26

<210> SEQ ID NO 13
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 13
caagtgagtc tgcacttcgg caccacc 27

<210> SEQ ID NO 14
<211> LENGTH: 13
<212> TYPE: PRT
<213> ORGANISM: Homo sapiens

<400> SEQUENCE: 14

Ala Ser Pro Ala Gly Thr Pro Pro Gly Arg Ala Ser Pro
 1               5                  10

<210> SEQ ID NO 15
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 15
cggatcgtgg gagggcgct ggcctcg 27

<210> SEQ ID NO 16
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 16
cagcaggcca gctggttagg attttatgaa tcgcac 36

<210> SEQ ID NO 17
<211> LENGTH: 9
<212> TYPE: PRT
<213> ORGANISM: Homo sapiens
<220> FEATURE:
<223> OTHER INFORMATION: Start of the endotheliase 2 protease domain

<400> SEQUENCE: 17

Arg Ile Val Gly Gly Ala Leu Ala Ser
 1               5

<210> SEQ ID NO 18
<211> LENGTH: 22
<212> TYPE: DNA
<213> ORGANISM: Artificial Sequence
<220> FEATURE:
<223> OTHER INFORMATION: Anti-sense primer

<400> SEQUENCE: 18
tccaggaaag cctccacagg tc 22

<210> SEQ ID NO 19
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 19
ggaggcaagc agggtggatg tgagcggac 29

<210> SEQ ID NO 20
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 20
ttcctccggg aggtgcaggt caatc       25

<210> SEQ ID NO 21
<211> LENGTH: 9276
<212> TYPE: DNA
<213> ORGANISM: Pichia pastoris
<220> FEATURE:
<223> OTHER INFORMATION: pPic9K vector

<400> SEQUENCE: 21

| | | | | | |
|---|---|---|---|---|---|
| agatctaaca | tccaaagacg | aaaggttgaa | tgaaaccttt | ttgccatccg acatccacag | 60 |
| gtccattctc | acacataagt | gccaaacgca | acaggagggg | atacactagc agcagaccgt | 120 |
| tgcaaacgca | ggacctccac | tcctcttctc | ctcaacaccc | acttttgcca tcgaaaaacc | 180 |
| agcccagtta | ttgggcttga | ttggagctcg | ctcattccaa | ttccttctat taggctacta | 240 |
| acaccatgac | tttattagcc | tgtctatcct | ggcccccctg | gcgaggttca tgtttgttta | 300 |
| tttccgaatg | caacaagctc | cgcattacac | ccgaacatca | ctccagatga gggctttctg | 360 |
| agtgtggggt | caaatagttt | catgttcccc | aaatggccca | aaactgacag tttaaacgct | 420 |
| gtcttggaac | ctaatatgac | aaaagcgtga | tctcatccaa | gatgaactaa gtttggttcg | 480 |
| ttgaaatgct | aacggccagt | tggtcaaaaa | gaaacttcca | aaagtcgcca taccgtttgt | 540 |
| cttgtttggt | attgattgac | gaatgctcaa | aaataatctc | attaatgctt agcgcagtct | 600 |
| ctctatcgct | tctgaacccc | ggtgcacctg | tgccgaaacg | caaatgggga acacccgct | 660 |
| ttttggatga | ttatgcattg | tctccacatt | gtatgcttcc | aagattctgg tgggaatact | 720 |
| gctgatagcc | taacgttcat | gatcaaaatt | taactgttct | aacccctact tgacagcaat | 780 |
| atataaacag | aaggaagctg | ccctgtctta | aacctttttt | tttatcatca ttattagctt | 840 |
| actttcataa | ttgcgactgg | ttccaattga | caagcttttg | attttaacga cttttaacga | 900 |
| caacttgaga | agatcaaaaa | acaactaatt | attcgaagga | tccaaacgat gagatttcct | 960 |
| tcaatttta | ctgcagtttt | attcgcagca | tcctccgcat | tagctgctcc agtcaacact | 1020 |
| acaacagaag | atgaaacggc | acaaattccg | gctgaagctg | tcatcggtta ctcagattta | 1080 |
| gaagggatt | tcgatgttgc | tgttttgcca | ttttccaaca | gcacaaataa cgggttattg | 1140 |
| tttataaata | ctactattgc | cagcattgct | gctaaagaag | aagggggtatc tctcgagaaa | 1200 |
| agagaggctg | aagcttacgt | agaattccct | agggcggccg | cgaattaatt cgccttagac | 1260 |
| atgactgttc | ctcagttcaa | gttgggcact | tacgagaaga | ccggtcttgc tagattctaa | 1320 |
| tcaagaggat | gtcagaatgc | catttgcctg | agagatgcag | gcttcatttt tgatactttt | 1380 |
| ttatttgtaa | cctatatagt | ataggatttt | ttttgtcatt | ttgtttcttc tcgtacgagc | 1440 |
| ttgctcctga | tcagcctatc | tcgcagctga | tgaatatctt | gtggtagggg tttgggaaaa | 1500 |
| tcattcgagt | ttgatgtttt | tcttggtatt | tcccactcct | cttcagagta cagaagatta | 1560 |
| agtgagaagt | tcgtttgtgc | aagcttatcg | ataagcttta | atgcggtagt ttatcacagt | 1620 |
| taaattgcta | acgcagtcag | gcaccgtgta | tgaaatctaa | caatgcgctc atcgtcatcc | 1680 |
| tcggcaccgt | caccctggat | gctgtaggca | taggcttggt | tatgccggta ctgccgggcc | 1740 |
| tcttgcggga | tatcgtccat | tccgacagca | tcgccagtca | ctatgcgtg ctgctagcgc | 1800 |
| tatatgcgtt | gatgcaattt | ctatgcgcac | ccgttctcgg | agcactgtcc gaccgctttg | 1860 |

```
gccgccgccc agtcctgctc gcttcgctac ttggagccac tatcgactac gcgatcatgg    1920
cgaccacacc cgtcctgtgg atctatcgaa tctaaatgta agttaaaatc tctaaataat    1980
taaataagtc ccagtttctc catacgaacc ttaacagcat tgcggtgagc atctagacct    2040
tcaacagcag ccagatccat cactgcttgg ccaatatgtt tcagtccctc aggagttacg    2100
tcttgtgaag tgatgaactt ctggaaggtt gcagtgttaa ctccgctgta ttgacgggca    2160
tatccgtacg ttggcaaagt gtggttggta ccggaggagt aatctccaca actctctgga    2220
gagtaggcac caacaaacac agatccagcg tgttgtactt gatcaacata agaagaagca    2280
ttctcgattt gcaggatcaa gtgttcagga gcgtactgat tggacatttc caaagcctgc    2340
tcgtaggttg caaccgatag ggttgtagag tgtgcaatac acttgcgtac aatttcaacc    2400
cttgcaaact gcacagcttg gttgtgaaca gcatcttcaa ttctggcaag ctccttgtct    2460
gtcatatcga cagccaacag aatcacctgg gaatcaatac catgttcagc ttgagacaga    2520
aggtctgagg caacgaaatc tggatcagcg tatttatcag caataactag aacttcagaa    2580
ggcccagcag gcatgtcaat actacacagg gctgatgtgt cattttgaac catcatcttg    2640
gcagcagtaa cgaactggtt tcctggacca aatattttgt cacacttagg aacagtttct    2700
gttccgtaag ccatagcagc tactgcctgg gcgcctcctg ctagcacgat acacttagca    2760
ccaaccttgt gggcaacgta gatgacttct ggggtaaggg taccatcctt cttaggtgga    2820
gatgcaaaaa caatttcttt gcaaccagca actttggcag gaacacccag catcagggaa    2880
gtggaaggca gaattgcggt tccaccagga atatagaggc caactttctc aataggtctt    2940
gcaaaacgag agcagactac accagggcaa gtctcaactt gcaacgtctc cgttagttga    3000
gcttcatgga atttcctgac gttatctata gagagatcaa tggctctctt aacgttatct    3060
ggcaattgca taagttcctc tgggaaagga gcttctaaca caggtgtctt caaagcgact    3120
ccatcaaact tggcagttag ttctaaaagg gctttgtcac cattttgacg aacattgtcg    3180
acaattggtt tgactaattc cataatctgt tccgttttct ggataggacg acgaagggca    3240
tcttcaattt cttgtgagga ggccttagaa acgtcaattt tgcacaattc aatacgacct    3300
tcagaaggga cttctttagg tttggattct tctttaggtt gttccttggt gtatcctggc    3360
ttggcatctc ctttccttct agtgaccttt agggacttca tatccaggtt tctctccacc    3420
tcgtccaacg tcacaccgta cttggcacat ctaactaatg caaaataaaa taagtcagca    3480
cattcccagg ctatatcttc cttggattta gcttctgcaa gttcatcagc ttcctcccta    3540
attttagcgt tcaacaaaac ttcgtcgtca ataaccgtt tggtataaga accttctgga    3600
gcattgctct tacgatccca caaggtggct tccatggctc taagacccctt tgattggcca    3660 aaacaggaag tgcgttccaa gtgacagaaa ccaacacctg tttgttcaac cacaaatttc    3720
aagcagtctc catcacaatc caattcgata cccagcaact tttgagttgc tccagatgta    3780
gcacctttat accacaaacc gtgacgacga gattggtaga ctccagtttg tgtccttata    3840
gcctccggaa tagacttttt ggacgagtac accaggccca acgagtaatt agaagagtca    3900
gccaccaaag tagtgaatag accatcgggg cggtcagtag tcaaagacgc caacaaaatt    3960
tcactgacag ggaactttttt gacatcttca gaaagttcgt attcagtagt caattgccga    4020
gcatcaataa tggggattat accagaagca acagtggaag tcacatctac caactttgcg    4080
gtctcagaaa aagcataaac agttctacta ccgccattag tgaaactttt caaatcgccc    4140
agtggagaag aaaaaggcac agcgatacta gcattagcgg gcaaggatgc aactttatca    4200
accagggtcc tatagataac cctagcgcct gggatcatcc tttggacaac tctttctgcc    4260
```

-continued

```
aaatctaggt ccaaaatcac ttcattgata ccattattgt acaacttgag caagttgtcg    4320
atcagctcct caaattggtc ctctgtaacg gatgactcaa cttgcacatt aacttgaagc    4380
tcagtcgatt gagtgaactt gatcaggttg tgcagctggt cagcagcata gggaaacacg    4440
gcttttccta ccaaactcaa ggaattatca aactctgcaa cacttgcgta tgcaggtagc    4500
aagggaaatg tcatacttga agtcggacag tgagtgtagt cttgagaaat tctgaagccg    4560
tatttttatt atcagtgagt cagtcatcag gagatcctct acgccggacg catcgtggcc    4620
gacctgcagg ggggggggg gcgctgaggt ctgcctcgtg aagaaggtgt tgctgactca    4680
taccaggcct gaatcgcccc atcatccagc cagaaagtga gggagccacg gttgatgaga    4740
gctttgttgt aggtggacca gttggtgatt ttgaactttt gctttgccac ggaacggtct    4800
gcgttgtcgg aagatgcgt gatctgatcc ttcaactcag caaaagttcg atttattcaa    4860
caaagccgcc gtcccgtcaa gtcagcgtaa tgctctgcca gtgttacaac caattaacca    4920
attctgatta gaaaaactca tcgagcatca aatgaaactg caatttattc atatcaggat    4980
tatcaatacc atattttttga aaaagccgtt tctgtaatga aggagaaaac tcaccgaggc    5040
agttccatag gatggcaaga tcctggtatc ggtctgcgat tccgactcgt ccaacatcaa    5100
tacaacctat taatttcccc tcgtcaaaaa taaggttatc aagtgagaaa tcaccatgag    5160
tgacgactga atccggtgag aatggcaaaa gcttatgcat ttctttccag acttgttcaa    5220
caggccagcc attacgctcg tcatcaaaat cactcgcatc aaccaaaccg ttattcattc    5280
gtgattgcgc ctgagcgaga cgaaatacgc gatcgctgtt aaaaggacaa ttacaaacag    5340
gaatcgaatg caaccggcgc aggaacactg ccagcgcatc aacaatattt tcacctgaat    5400
caggatattc ttctaatacc tggaatgctg ttttcccggg gatcgcagtg gtgagtaacc    5460
atgcatcatc aggagtacgg ataaaatgct tgatggtcgg aagaggcata aattccgtca    5520
gccagtttag tctgaccatc tcatctgtaa catcattggc aacgctacct ttgccatgtt    5580
tcagaaacaa ctctggcgca tcgggcttcc catacaatcg atagattgtc gcacctgatt    5640
gcccgacatt atcgcgagcc catttatacc catataaatc agcatccatg ttggaattta    5700
atcgcggcct cgagcaagac gtttcccgtt gaatatggct cataacaccc cttgtattac    5760
tgtttatgta agcagacagt tttattgttc atgatgatat ttttttatct tgtgcaatgt    5820
aacatcagag attttgagac acaacgtggc tttcccccccc ccccctgcag gtcggcatca    5880
ccggcgccac aggtgcggtt gctggcgcct atatcgccga catcaccgat ggggaagatc    5940
gggctcgcca cttcgggctc atgagcgctt gtttcggcgt gggtatggtg caggccccg    6000 tggccggggg actgttgggc gccatctcct tgcatgcacc attccttgcg gcggcggtgc    6060
tcaacggcct caacctacta ctgggctgct tcctaatgca ggagtcgcat aagggagagc    6120
gtcgagtatc tatgattgga agtatgggaa tggtgatacc cgcattcttc agtgtcttga    6180
ggtctcctat cagattatgc ccaactaaag caaccggagg aggagatttc atggtaaatt    6240
tctctgactt tggtcatca gtagactcga actgtgagac tatctcggtt atgacagcag    6300
aaatgtcctt cttggagaca gtaaatgaag tcccaccaat aaagaaatcc ttgttatcag    6360
gaacaaactt cttgtttcga acttttttcgg tgccttgaac tataaaatgt agagtggata    6420
tgtcgggtag gaatggagcg ggcaaatgct taccttctgg accttcaaga ggtatgtagg    6480
gtttgtagat actgatgcca acttcagtga caacgttgct atttcgttca aaccattccg    6540
aatccagaga aatcaaagtt gtttgtctac tattgatcca agccagtgcg gtcttgaaac    6600
```

```
tgacaatagt gtgctcgtgt tttgaggtca tctttgtatg aataaatcta gtctttgatc    6660
taaataatct tgacgagcca aggcgataaa tacccaaatc taaaactctt ttaaaacgtt    6720
aaaaggacaa gtatgtctgc ctgtattaaa ccccaaatca gctcgtagtc tgatcctcat    6780
caacttgagg ggcactatct tgttttagag aaatttgcgg agatgcgata tcgagaaaaa    6840
ggtacgctga ttttaaacgt gaaatttatc tcaagatctc tgcctcgcgc gtttcggtga    6900
tgacggtgaa aacctctgac acatgcagct cccggagacg gtcacagctt gtctgtaagc    6960
ggatgccggg agcagacaag cccgtcaggg cgcgtcagcg ggtgttggcg ggtgtcgggg    7020
cgcagccatg acccagtcac gtagcgatag cggagtgtat actggcttaa ctatgcggca    7080
tcagagcaga ttgtactgag agtgcaccat atgcggtgtg aaataccgca cagatgcgta    7140
aggagaaaat accgcatcag cgctcttcc gcttcctcgc tcactgactc gctgcgctcg    7200
gtcgttcggc tgcggcgagc ggtatcagct cactcaaagg cggtaatacg gttatccaca    7260
gaatcagggg ataacgcagg aaagaacatg tgagcaaaag gccagcaaaa ggccaggaac    7320
cgtaaaaagg ccgcgttgct ggcgtttttc cataggctcc gcccccctga cgagcatcac    7380
aaaaatcgac gctcaagtca gaggtggcga acccgacag gactataaag ataccaggcg    7440
tttccccctg gaagctccct cgtgcgctct cctgttccga ccctgccgct taccggatac    7500
ctgtccgcct ttctcccttc gggaagcgtg gcgctttctc aatgctcacg ctgtaggtat    7560
ctcagttcgg tgtaggtcgt tcgctccaag ctgggctgtg tgcacgaacc ccccgttcag    7620
cccgaccgct gcgccttatc cggtaactat cgtcttgagt ccaacccggt aagacacgac    7680
ttatcgccac tggcagcagc cactggtaac aggattagca gagcgaggta tgtaggcggt    7740
gctacagagt tcttgaagtg gtggcctaac tacggctaca ctagaaggac agtatttggt    7800
atctgcgctc tgctgaagcc agttaccttc ggaaaaagag ttggtagctc ttgatccggc    7860
aaacaaacca ccgctggtag cggtggtttt tttgtttgca agcagcagat tacgcgcaga    7920
aaaaaaggat ctcaagaaga tcctttgatc ttttctacgg ggtctgacgc tcagtggaac    7980
gaaaactcac gttaagggat tttggtcatg agattatcaa aaaggatctt cacctagatc    8040
cttttaaatt aaaaatgaag ttttaaatca atctaaagta tatatgagta aacttggtct    8100
gacagttacc aatgcttaat cagtgaggca cctatctcag cgatctgtct atttcgttca    8160
tccatagttg cctgactccc cgtcgtgtag ataactacga tacgggaggg cttaccatct    8220
ggccccagtg ctgcaatgat accgcgagac ccacgctcac cggctccaga tttatcagca    8280
ataaaccagc cagccggaag ggccgagcgc agaagtggtc ctgcaacttt atccgcctcc    8340
atccagtcta ttaattgttg ccgggaagct agagtaagta gttcgccagt taatagtttg    8400
cgcaacgttg ttgccattgc tgcaggcatc gtggtgtcac gctcgtcgtt tggtatggct    8460
tcattcagct ccggttccca acgatcaagg cgagttacat gatccccat gttgtgcaaa    8520 aaagcggtta gctccttcgg tcctccgatc gttgtcagaa gtaagttggc cgcagtgtta    8580
tcactcatgg ttatggcagc actgcataat tctcttactg tcatgccatc cgtaagatgc    8640
ttttctgtga ctggtgagta ctcaaccaag tcattctgag aatagtgtat gcggcgaccg    8700
agttgctctt gcccggcgtc aacacgggat aataccgcgc cacatagcag aactttaaaa    8760
gtgctcatca ttggaaaacg ttcttcgggg cgaaaactct caaggatctt accgctgttg    8820
agatccagtt cgatgtaacc cactcgtgca cccaactgat cttcagcatc ttttactttc    8880
accagcgttt ctgggtgagc aaaaacagga aggcaaaatg ccgcaaaaaa gggaataagg    8940
gcgacacgga aatgttgaat actcatactc ttccttttc aatattattg aagcatttat    9000
```

-continued

```
cagggttatt gtctcatgag cggatacata tttgaatgta tttagaaaaa taaacaaata    9060
ggggttccgc gcacatttcc ccgaaaagtg ccacctgacg tctaagaaac cattattatc    9120
atgacattaa cctataaaaa taggcgtatc acgaggccct ttcgtcttca agaattaatt    9180
ctcatgtttg acagcttatc atcgataagc tgactcatgt tggtattgtg aaatagacgc    9240
agatcgggaa cactgaaaaa taacagttat tattcg                              9276
```

```
<210> SEQ ID NO 22
<211> LENGTH: 1471
<212> TYPE: DNA
<213> ORGANISM: Homo sapiens
<220> FEATURE:
<223> OTHER INFORMATION: DESC1 gene
<220> FEATURE:
<221> NAME/KEY: protease domain
<222> LOCATION: (626)..(1324)
<220> FEATURE:
<221> NAME/KEY: CDS
<222> LOCATION: (56)...(1324)
<220> FEATURE:
<221> NAME/KEY: modified_base
<222> LOCATION: 127
<223> OTHER INFORMATION: s = C or G
<220> FEATURE:
<221> NAME/KEY: modified_base
<222> LOCATION: 164
<223> OTHER INFORMATION: s = C or G
<220> FEATURE:
<221> NAME/KEY: modified_base
<222> LOCATION: 1233
<223> OTHER INFORMATION: s = C or G

<400> SEQUENCE: 22
```

```
tgacttggat gtagacctcg accttcacag gactcttcat tgctggttgg caatg atg      58
                                                             Met
                                                              1 tat cgg cca gat gtg gtg agg gct agg aaa aga gtt tgt tgg gaa ccc     106
Tyr Arg Pro Asp Val Val Arg Ala Arg Lys Arg Val Cys Trp Glu Pro
        5                  10                  15 tgg gtt atc ggc ctc gtc ats ttc ata tcc ctg att gtc ctg gca gtg     154
Trp Val Ile Gly Leu Val Xaa Phe Ile Ser Leu Ile Val Leu Ala Val
 20                  25                  30 tgc att gga stc act gtt cat tat gtg aga tat aat caa aag aag acc     202
Cys Ile Gly Xaa Thr Val His Tyr Val Arg Tyr Asn Gln Lys Lys Thr
 35                  40                  45 tac aat tac tat agc aca ttg tca ttt aca act gac aaa cta tat gct     250
Tyr Asn Tyr Tyr Ser Thr Leu Ser Phe Thr Thr Asp Lys Leu Tyr Ala
 50                  55                  60                  65 gag ttt ggc aga gag gct tct aac aat ttt aca gaa atg agc cag aga     298
Glu Phe Gly Arg Glu Ala Ser Asn Asn Phe Thr Glu Met Ser Gln Arg
                 70                  75                  80 ctt gaa tca atg gtg aaa aat gca ttt tat aaa tct cca tta agg gaa     346
Leu Glu Ser Met Val Lys Asn Ala Phe Tyr Lys Ser Pro Leu Arg Glu
             85                  90                  95 gaa ttt gtc aag tct cag gtt atc aag ttc agt caa cag aag cat gga     394
Glu Phe Val Lys Ser Gln Val Ile Lys Phe Ser Gln Gln Lys His Gly
            100                 105                 110 gtg ttg gct cat atg ctg ttg att tgt aga ttt cac tct act gag gat     442
Val Leu Ala His Met Leu Leu Ile Cys Arg Phe His Ser Thr Glu Asp
        115                 120                 125 cct gaa act gta gat aaa att gtt caa ctt gtt tta cat gaa aag ctg     490
Pro Glu Thr Val Asp Lys Ile Val Gln Leu Val Leu His Glu Lys Leu
130                 135                 140                 145
```

-continued

```
caa gat gct gta gga ccc cct aaa gta gat cct cac tca gtt aaa att        538
Gln Asp Ala Val Gly Pro Pro Lys Val Asp Pro His Ser Val Lys Ile
            150                 155                 160 aaa aaa atc aac aag aca gaa aca gac agc tat cta aac cat tgc tgc        586
Lys Lys Ile Asn Lys Thr Glu Thr Asp Ser Tyr Leu Asn His Cys Cys
        165                 170                 175 gga aca cga aga agt aaa act cta ggt cag agt ctc agg atc gtt ggt        634
Gly Thr Arg Arg Ser Lys Thr Leu Gly Gln Ser Leu Arg Ile Val Gly
    180                 185                 190 ggg aca gaa gta gaa gag ggt gaa tgg ccc tgg cag gct agc ctg cag        682
Gly Thr Glu Val Glu Glu Gly Glu Trp Pro Trp Gln Ala Ser Leu Gln
195                 200                 205 tgg gat ggg agt cat cgc tgt gga gca acc tta att aat gcc aca tgg        730
Trp Asp Gly Ser His Arg Cys Gly Ala Thr Leu Ile Asn Ala Thr Trp
210                 215                 220                 225 ctt gtg agt gct gct cac tgt ttt aca aca tat aag aac cct gcc aga        778
Leu Val Ser Ala Ala His Cys Phe Thr Thr Tyr Lys Asn Pro Ala Arg
                230                 235                 240 tgg act gct tcc ttt gga gta aca ata aaa cct tcg aaa atg aaa cgg        826
Trp Thr Ala Ser Phe Gly Val Thr Ile Lys Pro Ser Lys Met Lys Arg
            245                 250                 255 ggt ctc cgg aga ata att gtc cat gaa aaa tac aaa cac cca tca cat        874
Gly Leu Arg Arg Ile Ile Val His Glu Lys Tyr Lys His Pro Ser His
        260                 265                 270 gac tat gat att tct ctt gca gag ctt tct agc cct gtt ccc tac aca        922
Asp Tyr Asp Ile Ser Leu Ala Glu Leu Ser Ser Pro Val Pro Tyr Thr
    275                 280                 285 aat gca gta cat aga gtt tgt ctc cct gat gca tcc tat gag ttt caa        970
Asn Ala Val His Arg Val Cys Leu Pro Asp Ala Ser Tyr Glu Phe Gln
290                 295                 300                 305 cca ggt gat gtg atg ttt gtg aca gga ttt gga gca ctg aaa aat gat       1018
Pro Gly Asp Val Met Phe Val Thr Gly Phe Gly Ala Leu Lys Asn Asp
                310                 315                 320 ggt tac agt caa aat cat ctt cga caa gca cag gtg act ctc ata gac       1066
Gly Tyr Ser Gln Asn His Leu Arg Gln Ala Gln Val Thr Leu Ile Asp
            325                 330                 335 gct aca act tgc aat gaa cct caa gct tac aat gac gcc ata act cct       1114
Ala Thr Thr Cys Asn Glu Pro Gln Ala Tyr Asn Asp Ala Ile Thr Pro
        340                 345                 350 aga atg tta tgt gct ggc tcc tta gaa gga aaa aca gat gca tgc cag       1162
Arg Met Leu Cys Ala Gly Ser Leu Glu Gly Lys Thr Asp Ala Cys Gln
    355                 360                 365 ggt gac tct gga gga cca ctg gtt agt tca gat gct aga gat atc tgg       1210
Gly Asp Ser Gly Gly Pro Leu Val Ser Ser Asp Ala Arg Asp Ile Trp
370                 375                 380                 385 tac ctt gct gga ata gtg agc tsg gga gat gaa tgt gcg aaa ccc aac       1258
Tyr Leu Ala Gly Ile Val Ser Xaa Gly Asp Glu Cys Ala Lys Pro Asn
                390                 395                 400 aag cct ggt gtt tat act aga gtt acg gcc ttg cgg gac tgg att act       1306
Lys Pro Gly Val Tyr Thr Arg Val Thr Ala Leu Arg Asp Trp Ile Thr
            405                 410                 415 tca aaa act ggt atc taa gagagaaaag cctcatggaa cagataacat              1354
Ser Lys Thr Gly Ile
                420 tttttttgt ttttgggtg tggaggccat ttttagagat acagaattgg agaagacttg       1414
caaaacagct agatttgact gatctcaata aactgtttgc ttgatgcaaa aaaaaaa        1471
```

<210> SEQ ID NO 23
<211> LENGTH: 42

```
<212> TYPE: DNA
<213> ORGANISM: Artificial Sequence
<220> FEATURE:
<223> OTHER INFORMATION: Endotheliase 1 forward primer

<400> SEQUENCE: 23
tctctcgaga aaagaatcgt tggtgggaca gaagtagaag ag                    42

<210> SEQ ID NO 24
<211> LENGTH: 39
<212> TYPE: DNA
<213> ORGANISM: Artificial Sequence
<220> FEATURE:
<223> OTHER INFORMATION: Endotheliase 1 reverse primer

<400> SEQUENCE: 24
attcgcggcc gcttagatac cagttttga agtaatcca                        39

<210> SEQ ID NO 25
<211> LENGTH: 39
<212> TYPE: DNA
<213> ORGANISM: Artificial Sequence
<220> FEATURE:
<223> OTHER INFORMATION: Endotheliase 2 forward primer

<400> SEQUENCE: 25
tctctcgaga aaagaatcgt gggaggggcg ctggcctcg                       39

<210> SEQ ID NO 26
<211> LENGTH: 40
<212> TYPE: DNA
<213> ORGANISM: Artificial Sequence
<220> FEATURE:
<223> OTHER INFORMATION: Endotheliase 2 reverse primer

<400> SEQUENCE: 26
atagcggccg ctggttagga ttttatgaat cgcacctcgc                      40

<210> SEQ ID NO 27
<211> LENGTH: 422
<212> TYPE: PRT
<213> ORGANISM: Homo sapiens
<220> FEATURE:
<221> NAME/KEY: VARIANT
<222> LOCATION: 24
<223> OTHER INFORMATION: Xaa = Ile or Met
<220> FEATURE:
<221> NAME/KEY: VARIANT
<222> LOCATION: 37
<223> OTHER INFORMATION: Xaa = Leu or Val
<220> FEATURE:
<221> NAME/KEY: VARIANT
<222> LOCATION: 393
<223> OTHER INFORMATION: Xaa = Ser or Trp

<400> SEQUENCE: 27

Met Tyr Arg Pro Asp Val Val Arg Ala Arg Lys Arg Val Cys Trp Glu
 1               5                  10                  15

Pro Trp Val Ile Gly Leu Val Xaa Phe Ile Ser Leu Ile Val Leu Ala
            20                  25                  30

Val Cys Ile Gly Xaa Thr Val His Tyr Val Arg Tyr Asn Gln Lys Lys
        35                  40                  45

Thr Tyr Asn Tyr Tyr Ser Thr Leu Ser Phe Thr Thr Asp Lys Leu Tyr
    50                  55                  60

Ala Glu Phe Gly Arg Glu Ala Ser Asn Asn Phe Thr Glu Met Ser Gln
65                  70                  75                  80
```

-continued

```
Arg Leu Glu Ser Met Val Lys Asn Ala Phe Tyr Lys Ser Pro Leu Arg
             85                  90                  95

Glu Glu Phe Val Lys Ser Gln Val Ile Lys Phe Ser Gln Gln Lys His
            100                 105                 110

Gly Val Leu Ala His Met Leu Leu Ile Cys Arg Phe His Ser Thr Glu
            115                 120                 125

Asp Pro Glu Thr Val Asp Lys Ile Val Gln Leu Val Leu His Glu Lys
        130                 135                 140

Leu Gln Asp Ala Val Gly Pro Pro Lys Val Asp Pro His Ser Val Lys
145                 150                 155                 160

Ile Lys Lys Ile Asn Lys Thr Glu Thr Asp Ser Tyr Leu Asn His Cys
                165                 170                 175

Cys Gly Thr Arg Arg Ser Lys Thr Leu Gly Gln Ser Leu Arg Ile Val
            180                 185                 190

Gly Gly Thr Glu Val Glu Glu Gly Trp Pro Trp Gln Ala Ser Leu
            195                 200                 205

Gln Trp Asp Gly Ser His Arg Cys Gly Ala Thr Leu Ile Asn Ala Thr
    210                 215                 220

Trp Leu Val Ser Ala Ala His Cys Phe Thr Thr Tyr Lys Asn Pro Ala
225                 230                 235                 240

Arg Trp Thr Ala Ser Phe Gly Val Thr Ile Lys Pro Ser Lys Met Lys
                245                 250                 255

Arg Gly Leu Arg Arg Ile Ile Val His Glu Lys Tyr Lys His Pro Ser
            260                 265                 270

His Asp Tyr Asp Ile Ser Leu Ala Glu Leu Ser Ser Pro Val Pro Tyr
        275                 280                 285

Thr Asn Ala Val His Arg Val Cys Leu Pro Asp Ala Ser Tyr Glu Phe
    290                 295                 300

Gln Pro Gly Asp Val Met Phe Val Thr Gly Phe Gly Ala Leu Lys Asn
305                 310                 315                 320

Asp Gly Tyr Ser Gln Asn His Leu Arg Gln Ala Gln Val Thr Leu Ile
                325                 330                 335

Asp Ala Thr Thr Cys Asn Glu Pro Gln Ala Tyr Asn Asp Ala Ile Thr
            340                 345                 350

Pro Arg Met Leu Cys Ala Gly Ser Leu Glu Gly Lys Thr Asp Ala Cys
        355                 360                 365

Gln Gly Asp Ser Gly Gly Pro Leu Val Ser Ser Asp Ala Arg Asp Ile
    370                 375                 380

Trp Tyr Leu Ala Gly Ile Val Ser Xaa Gly Asp Glu Cys Ala Lys Pro
385                 390                 395                 400

Asn Lys Pro Gly Val Tyr Thr Arg Val Thr Ala Leu Arg Asp Trp Ile
                405                 410                 415

Thr Ser Lys Thr Gly Ile
                420
```

NUCLEIC ACIDS ENCODING ENDOTHELIASES, ENDOTHELIASES AND USES THEREOF

RELATED APPLICATIONS

This application is a continuation of International PCT application No. PCT/US00/31803 to Edwin L. Madison, Edgar O. Ong and Jiunn-Chem Yeh, filed Nov. 17, 2000, entitled "NUCLEIC ACIDS ENCODING ENDOTHELIASES, ENDOTHELIASES AND USES THEREOF". Benefit of priority thereto is claimed under 35 U.S.C. § 120.

Benefit of priority under 35 U.S.C. § 119(e) U.S. provisional application Ser. No. 60/166,391 to Edwin L. Madison and Edgar O. Ong, filed Nov. 18, 1999 entitled "NUCLEOTIDE AND PROTEIN SEQUENCES OF PROTEASE DOMAINS OF ENDOTHELIASE AND METHODS BASED THEREON"; and U.S. provisional application Ser. No. 60/234,840 to Edwin L. Madison, Edgar O. Ong and Jiunn-Chem Yeh, filed Sep. 22, 2000, entitled "NUCLEIC ACID MOLECULES ENCODING TRANSMEMBRANE SERINE PROTEASES, THE ENCODED PROTEINS AND METHODS BASED THEREON" is claimed herein.

This application is also related to U.S. provisional application Ser. No. 60/179,982, to Edwin L. Madison and Edgar O. Ong, filed Feb. 3, 2000, entitled "NUCLEOTIDE AND PROTEIN SEQUENCES OF A TRANSMEMBRANE SERINE PROTEASE AND METHODS BASED THEREOF"; U.S. provisional application Ser. No. 60/183,542, to Edwin L. Madison and Edgar O. Ong, filed Feb. 18, 2000, entitled "NUCLEOTIDE AND PROTEIN SEQUENCES OF A TRANSMEMBRANE SERINE PROTEASE AND METHODS BASED THEREOF"; U.S. provisional application Ser. No. 60/213,124, to Edwin L. Madison and Edgar O. Ong, filed Jun. 22, 2000, entitled "NUCLEOTIDE AND PROTEIN SEQUENCES OF A TRANSMEMBRANE SERINE PROTEASE AND METHODS BASED THEREOF"; U.S. provisional application Ser. No. 60/220,970, to Edwin L. Madison and Edgar O. Ong, filed Jul. 26, 2000, entitled "NUCLEOTIDE AND PROTEIN SEQUENCES OF A TRANSMEMBRANE SERINE PROTEASE AND METHODS BASED THEREOF."

The above-noted provisional applications and International PCT application are incorporated by reference in their entirety.

FIELD OF INVENTION

Nucleic acid molecules encoding the endotheliases are provided as are vectors containing the nucleic acids and cells containing the vectors. Preferred endotheliases are those that include the sequence of amino acids set forth in SEQ ID No. 2, 4, 6 or 22, and particularly the protease domain-encoding portions (SEQ ID No. 2, amino acids 321-562 of SEQ ID No. 4, and amino acids 321-688 of SEQ ID No. 6; amino acid 320 of each SEQ ID is optionally included as part of the protease domain). Also provided are nucleic acid molecules that hybridize, preferably along their full length, to a nuceic acid molecule having the nucleotide sequence of nucleotides set forth in SEQ ID NO. 1, 3, 5 or 22 or portions thereof, preferably, the protease domain-encoding portions or a sufficient portion thereof such that the encoded protein exhibits protease activity.

BACKGROUND OF THE INVENTION

Angiogenesis is the generation of new blood vessels from parent microvessels. Controlled and uncontrolled angiogenesis proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Angiogenesis, Modulators and Associated Diseases

Angiogenesis is highly regulated by a system of angiogenic stimulators and inhibitors. Known examples of angiogenesis stimulators include certain growth factors, cytokines, proteins, peptides, carbohydrates and lipids (Norrby, *APMIS*, 105:417-437 (1997); Polverini, *Crit. Rev. Oral. Biol. Med.*, 6:230-247 (1995)). A variety of endogenous and exogenous angiogenesis inhibitors are known in the art (Jackson et al., *FASEB*, 11:457-465 (1997); Norrby, *APMIS*, 105:417-437 (1997); and O'Reilly, *Investigational New Drugs*, 15:5-13 (1997)).

In adult organisms, capillary endothelial cells divide relatively infrequently. When triggered by appropriate signals, e.g., in response to hormonal signals during menses or following the release of pro-angiogenic mediators sequestered in the extracellular matrix, endothelial cells lining venules will systematically degrade their basement membrane and proximal extracellular matrix, migrate directionally, divide, and organize into new functioning capillaries, within a matter of days (Polverini, *Crit. Rev. Oral. Biol. Med.*, 6:230-247 (1995)). This dramatic amplification of the microvasculature is nevertheless temporary, for as rapidly as the new capillaries are formed, they virtually disappear within a matter of days or weeks, returning the tissue microvasculature to its status quo. It is this feature of transient growth and regression of capillaries that primarily distinguishes physiological angiogenesis from a pathological one (Polverini, *Crit. Rev. Oral. Biol. Med.*, 6:230-247 (1995)). In contrast, pathological angiogenesis is caused by a shift in the net balance between stimulators and inhibitors of angiogenesis, e.g., due to the overproduction of normal or aberrant forms of angiogenic mediators, or due to a relative deficiency in inhibitors of this process (Polverini, *Crit. Rev. Oral. Biol. Med.*, 6:230-247 (1995)).

Angiogenesis is essential for normal placental, embryonic, fetal and post-natal development and growth, but almost never occurs physiologically in adulthood except in very specific restricted situations. For example, angiogenesis is normally observed in wound healing, fetal and embryonal development and formation of the corpus luteum, endometrium and placenta. Angiogenesis in the adult is often associated with disease states.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases.

The control of angiogenesis is altered in certain disease states and, in many cases, the pathological damage associated with the disease is related to uncontrolled angiogenesis (see generally Norrby, *APMIS*, 105:417-437 (1997); and O'Reilly, *Investigational New Drugs*, 15:5-13 (1997)). Thus, angiogenesis is involved in the manifestation or progress of various diseases, for example, various inflammatory diseases, such as rheumatoid arthritis, psoriasis, diabetic retinopathies, certain ocular disorders, including recurrence of pterygii, scarring excimer laser surgery and glaucoma filtering surgery, various disorders of the anterior eye, cardiovascular disorders, chronic inflammatory diseases, wound repair, circulatory disorders, crest syndromes, dermatological disorders (see, e.g., U.S. Pat. Nos. 5,593,990, 5,629,327 and 5,712,291) and notably cancer, including solid neoplasms and vascular tumors. Several lines of direct evidence indicate that angiogenesis is essential for the growth and persistence of solid tumors and their metastases.

Thus, it is clear that angiogenesis plays a major role in the metastasis of cancer and in the pathology of a variety of other disorders. Repressing, eliminating or modulating this activity, should impact the etiology of these diseases and serve as a point of therapeutic intervention. In the disease state, prevention of angiogenesis could avert the damage caused by the invasion of the new microvascular system. Therapies directed at control of the angiogenic processes could lead to the abrogation or mitigation of these diseases.

Hence there is a need to develop therapeutics that target angiogenesis and modulate, particularly, inhibit aberrant or uncontrolled angiogenesis. Therefore it is an object herein to provide assays for identification of such agents. It is also an object herein to provide nucleic acids encoding the proteins and polypeptides and also to provide the proteins and polypeptides that are involved in the regulation of angiogenesis.

SUMMARY OF THE INVENTION

Provided herein are a class of membrane proteases that are expressed on cells, particularly endothelial cells, and that participate in angiogenesis. Also provided herein are methods of modulating the activity of the proteases and screening for compounds that modulate the activity thereof. Such modulation includes inhibiting, antagonizing agonizing and otherwise altering the activity of the protease. Of particular interest is the extracellular domain of these proteases that includes the proteolytic portion of the protein.

In particular, proteases, especially protease domains thereof, of proteins designated herein as endotheliase proteins are provided. Also provided herein are nucleic acids encoding the protease domains of the endotheliases and also the full-length endotheliases. In exemplary embodiments endotheliases, designated 1 and 2, particularly the protease domains thereof are provided. Full-length endotheliase 2 and variants thereof are also provided. Genes encoding endotheliases, particularly endotheliase 2, under control of the endogenous promoter and optionally other regulatory signals are provided.

Nucleic acid molecules encoding the endotheliases are provided as are vectors containing the nucleic acids and cells containing the vectors. Preferred endotheliases are those that include the sequence of amino acids set forth in SEQ ID No. 2, 4, 6 or 22, and particularly the protease domain-encoding portions (SEQ ID No. 2, amino acids 321-562 of SEQ ID No. 4, and amino acids 321-688 of SEQ ID No. 6; amino acid 320 of each SEQ ID is optionally included as part of the protease domain). Also provided are nucleic acid molecules that hybridize, preferably along their full length, to a nucleic acid molecule having the nucleotide sequence of nucleotides set forth in SEQ. ID NO. 1, 3, 5 or 22 or portions thereof, preferably, the protease domain-encoding portions or a sufficient portion thereof such that the encoded protein exhibits protease activity.

In preferred embodiments, the isolated nucleic acid molecule hybridizes to the nucleic acid having the nucleotide sequence set forth in the SEQ. ID No. 1, 3 or 5 under high stringency conditions. In another preferred embodiment, the isolated nucleic acid molecule contains sequence of nucleotides set forth in SEQ. ID No. 1, 3 or 5.

In one embodiment, the isolated nucleic acid molecule contains only the sequence of nucleotides set forth in SEQ. ID No 1, 3, or 5 or portions thereof, including molecules containing 14, 16, 30, 100 or up to the full length sequence thereof. In another embodiment, an isolated nucleic acid molecule has a nucleotide sequence complementary to the nucleotide sequence encoding the protease domain of the endotheliase is provided.

Vectors and plasmids containing the above-noted nucleic acid molecules are provided. Cells containing the plasmids or vectors are provided herein. More preferably, the cell is a bacterial cell, a yeast cell, a fungal cell, a plant cell, an insect cell or an animal cell.

Cells that contain the nucleic acids, and preferably express the encoded endotheliases or portion thereof, preferably the protease domain thereof, are also provided. The cells and vector can be engineered to express the endotheliase on the surface; such cells preferably contain the full-length coding portion of an endotheliase. In other embodiments, the cells and vectors are designed to secrete the encoding endotheliase or protease domain thereof, such as by including a sequence of nucleotides that directs secretion.

Methods for producing a protease domain of an endotheliase or an endotheliase by growing the above-described cells under conditions whereby the encoded protease domain of the endotheliase is expressed by the cell, and recovering the expressed protease domain protein, are provided herein.

Also provided herein are antibodies that specifically bind, particularly immunospecifically, to the endotheliases, preferably to the protease domains of the endotheliases.

Compositions, including pharmaceutical containing the endotheliase or protease domains of the endotheliase are provided. Combinations, kits containing the combinations and articles of manufacture containing the compositions or proteins are also provided. In one embodiment, combinations are provided herein that include an inhibitor of an endotheliase or an inhibitor of the protease activity thereof and an anti-angiogenic treatment or agent or non-anti-angiogenic tumor agent. The endotheliase inhibitor and the anti-angiogenic agent can be formulated in a single pharmaceutical composition or each can be formulated in a separate pharmaceutical composition. Kits containing the combinations are provided.

Transgenic non-human animals bearing inactivated genes encoding the endotheliases and bearing the genes encoding an endotheliase, preferably under control of a non-native promotor control are provided.

Conjugates of the endotheliases or protease domain portion thereof, such as conjugates of an endotheliase with a targeting agent to direct the endotheliase to a particular cell or tissue and conjugates with a linker or detection moiety for linkage to a solid support and detection, respectively, are provided. Methods using the conjugates are also provided. For example, the endotheliases or protease domain thereof may be linked to a cell specific targeting agent, particularly an agent, such as a growth factor or monoclonal antibody that binds to a cell surface protein that results in internalization of the conjugate or endotheliase portion thereof. These conjugates are administered with, before or following administration of a prodrug, such as a daunomycin or other cytotoxic agent. The prodrug is designed to be activated by the endotheliase. Upon binding to the targeted cells and internalization, the endotheliase activates the prodrug, thereby providing a means for target specific activation of a drug and selective killing or inhibition of targeted cells. Also provided herein are modulators of the activity of the endotheliase or protease domain.

Further provided herein are prognostic, diagnostic and therapeutic screening methods using the protease domains of the endotheliase and the nucleic acids encoding such domains. In particular, the prognostic, diagnostic and therapeutic screening methods are used for preventing or treating, or for finding agents useful in preventing or treating, diseases or disorders associated with aberrant level of angiogenesis.

Methods for screening for compounds that modulate the activity of the endotheliase are provided. Compounds identified by the screening methods are also provided. In vitro assays in which the compounds are identified by contacting them with the endotheliase or protease domain thereof and a substrate for the endotheliase are provided. A change in the amount of substrate cleaved in the presence of the compounds compared to the absence of the compound indicates that the compound modulates the activity of the endotheliase. Such compounds are selected for further analyses or for use to inhibit the activity of the endotheliase, such as inhibitors or agonists. The in vitro assays can be performed in liquid phase or on solid phase substrates by linking the endotheliase or protease domain thereof directly or via a linker to a solid support. Cell-based screening assays are also provided. The compounds can also be identified by contacting the substrates with a cell that expresses the endotheliase or the extracellular domain or proteolytically active portion thereof.

In one embodiment, a method for identifying a modulator of an endotheliase includes: a) contacting an endotheliase with a substrate of the endotheliase, and detecting the proteolysis of the substrate, whereby the activity of the endotheliase is assessed; b) contacting the endotheliase with a substrate of the endotheliase in the presence of a test substance, and detecting the proteolysis of the substrate, whereby the activity of the endotheliase is assessed; and c) comparing the activity of the endotheliase assessed in steps a) and b), whereby a difference in activity measured in step a) from the activity measured in step b) indicates that the test substance modulates the activity of the endotheliase. A plurality of the test substances can be screened simultaneously in any of the screening methods.

In another embodiment, the endotheliase to be screened is isolated from a target cell and the test substance is a therapeutic compound. A difference of the endotheliase activity measured in the presence and in the absence of the test substance indicates that the target cell responds to the therapeutic compound. For example, detection of protease domains in the blood or other body fluid can be indicative of cancer, particularly metastatic cancer.

Method for diagnosing diseases or disorders by detecting levels of endotheliases or protease domains thereof or encoding nucleic acids in body tissues and body fluids are provided. The methods require testing a body fluid or tissue for the presence or level of an endotheliase or protease domain thereof and assessing whether the level is higher or lower than in non-disease state.

For example, methods of diagnosing a disease or disorder by detecting an aberrant level of an endotheliase in a subject. The methods include the steps of measuring the level of the DNA, RNA, protein or functional activity of an endothelial endotheliase, in a sample derived from a subject, where an increase or decrease in the level of the DNA, RNA, protein or functional activity of the endotheliase, relative to the level of the DNA, RNA, protein or functional activity found in an analogous sample not having the disease or disorder indicates the presence of the disease or disorder in the subject.

In another embodiment, a method of diagnosing or screening for the presence of or a predisposition for developing a disease or disorder associated with undesired and/or uncontrolled angiogenesis in a subject is provided. In this method, the level of DNA, RNA, protein, or functional activity of an endotheliase in a sample derived from the subject, where an increase in the level of the DNA, RNA, protein, or functional activity in the sample, relative to the level of the DNA, RNA, protein, or functional activity found in an analogous sample not having the undesired and/or uncontrolled angiogenesis, indicates the presence of the undesired and/or uncontrolled angiogenesis.

Methods of diagnosing or screening for the presence of or a predisposition for developing a disease or disorder associated with deficient angiogenesis in a subject are provided herein. These methods include, for example, a method practiced by measuring the level of DNA, RNA, protein, or functional activity of an endotheliase in a sample derived from the subject, where a decrease in the level of the DNA, RNA; protein, or functional activity in the sample, relative to the level of, the DNA, RNA, protein, or functional activity found in an analogous sample not having the deficient angiogenesis, indicates the presence of the deficient angiogenesis.

Methods of treatment of endotheliase-mediated disorders, such as disorders involving excessive or deficient angiogenesis or related processes as evidenced by increased or decreased neovascularization, are provided. These treatments are effected by administering to a mammal, such as a human, an agent that modulates the activity of the endotheliase, thereby treating the disorder. Such treatments include, but are not limited to, an antibody or fragment thereof or antisense oligonucleotide provided herein and compounds obtained using the screening methods provided herein.

Hence, provided are methods for treatment or prophylaxis of a disease or disorder associated with undesired and/or uncontrolled angiogenesis in a mammal by administering to a mammal an effective amount of an inhibitor of an endotheliase, whereby the disease or disorder is treated or prevented are provided. The endotheliase inhibitor used in the treatment or prevention is preferably administered with a pharmaceutically acceptable carrier or excipient and the mammal treated is a human. Preferred inhibitors herein are antibodies that specifically bind to the endotheliase or to the protease domain thereof, and inhibitors of translation of the encoding mRNA and inhibitors of transcription of the mRNA, including antisense nucleic acid molecules.

In another embodiment, the treatment or prevention method also includes administering an anti-angiogenic treatment(s) or agent(s) or non-anti-angiogenic anti-tumor agents in combination therewith. The further anti-angiogenic agent or treatment may be administered simultaneously, subsequently or prior to administration of the endotheliase inhibitor, which can be, for example, an antibody or a fragment or derivative thereof containing the binding region thereof against the endotheliase, an antisense nucleic acid encoding the endotheliase, or a nucleic acid containing at least a portion of a gene encoding the endotheliase into which a heterologous nucleotide sequence has been inserted such that the heterologous sequence inactivates the biological activity of at least a portion of the gene encoding the endotheliase, in which the portion of the gene encoding the endotheliase flanks the heterologous sequence so as to promote homologous recombination with a genomic gene encoding the endotheliase.

The undesired angiogenesis to be treated or prevented is associated with disorders and diseases that include, but are not limited to, solid neoplasms, vascular malformations, and cardiovascular disorders, chronic inflammatory diseases, aberrant wound repairs, such as observed following glaucoma filtering surgeries and excimer laser eye surgery, circulatory disorders, crest syndromes, dermatological disorders and ocular disorders. The vascular malformations and cardiovascular disorders to be treated or prevented include angiofibroma, angiolipoma, atherosclerosis, restenosis/reperfusion injury, arteriovenous malformations, hemangiomatosis and vascular adhesions, dyschondroplasia with vascular hamartomas (Fafucci's syndrome), hereditary hemorrhagic telangiectasia (Rendu-Osler-Weber syndrome), or Von Hipple Lindau syndrome; the chronic inflammatory diseases to be treated or prevented are diabetes mellitus, hemophiliac joints, inflammatory bowel disease, nonhealing fractures, periodontitis (rapidly progressing and juvenile), psoriasis, rheumatoid arthritis, venous stasis ulcers, granulations-burns, hypertrophic scars, liver cirrhosis, osteoradionecrosis, postoperative adhesions, pyogenic granuloma, or systemic sclerosis; the circulatory disorder to be treated or prevented is Raynaud's phenomenon; the crest syndromes to be treated or prevented are calcinosis, esophageal dysmotility, sclerodactyly and telangiectasis; the dermatological disorders to be treated or prevented are systemic vasculitis, scleroderma, pyoderma gangrenosum, vasculopathy, venous, arterial ulcers, Sturge-Weber syndrome, Port-wine stains, blue rubber bleb nevus syndrome, Klippel-Trenaunay-Weber syndrome or Osler-Weber-Rendu syndrome; and the ocular disorders to be treated or prevented are blindness caused by ocular neovascular disease, corneal graft neovascularization, macular degeneration in the eye, neovascular glaucoma, trachoma, diabetic retinopathy, myopic degeneration, retinopathy of prematurity, retrolental fibroplasia, or corneal neovascularization.

In another embodiment, a method for treating or preventing a disease or disorder associated with deficient angiogenesis in a mammal is provided herein. The method includes administering to a mammal an effective amount of an endotheliase protein, a nucleic acid encoding the protein, and a nucleic acid encoding a derivative or analog of the protein that is active in promoting angiogenesis, whereby the disease or disorder is treated or prevented. In a preferred embodiment, the endotheliase protein, a derivative or analog of the protein, a nucleic acid encoding the protein, and a nucleic acid encoding a derivative or analog of the protein is administered with a pharmaceutically acceptable carrier or excipient. The mammal to be treated, preferably, is a human. In another embodiment, the treatment or prevention method further includes administering a pro-angiogenic treatment or agent.

Also provided are methods for treating or preventing a disease or disorder associated with deficient or defective angiogenesis in a mammal, such as a human, by administering to a mammal an effective amount of an endotheliase or a catalytically or functionally active portion, such as a protease domain, thereof or an agonist of the activity of an endotheliase, whereby the disease or disorder is treated or prevented or the symptoms are ameliorated. The method can further include, administering an pro-angiogenic treatment or agent that promotes angiogenesis simultaneously, prior to or after administration of the endotheliase or portion thereof.

Among the endotheliases provided herein are those whose activity is upregulated during angiogenesis. Such endotheliases can serve targets for activation of prodrugs that are designed to be selectively activated by these endotheliases. Hence therapeutic methods for treating disorders that involve endothelial cells that express such upregulated endotheliases are provided.

Also provided herein are transgenic non-human animals. In these animals, an endogenous gene of an endotheliase is deleted or inactivated by homologous recombination or insertional mutagenesis of the animal or an ancestor thereof. In particular, recombinant non-human animals in which an endogenous gene encoding an endotheliase has been deleted or inactivated by homologous recombination or insertional mutagenesis of the animal or an ancestor thereof, are provided. The endotheliase includes endotheliase 1 and endothliase 2. Inactivation can be effected by any means known to those of skill in the art, including, but are not limited to, recombination with a nucleic acid molecule encoding an endotheliase, such as any provided herein, that has been modified by a deletion, insertion or other mutation where, upon recombination the endogenous endotheliase is inactivated.

Also provided herein are articles of manufacture that contain: a) packaging material; b) an endotheliase or protease domain thereof, or a composition containing the endotheliase or protease domain thereof; and c) a label indicating that the article is for use in identifying a modulator of the activity of an endotheliase in a sample or for diagnostic, therapeutic or drug screening use.

DETAILED DESCRIPTION OF THE INVENTION

A. Definitions

Figure 1:
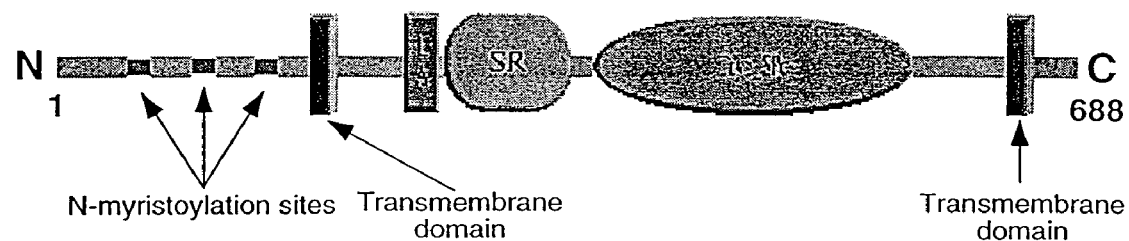
FIG. 1 depicts the domain organization of the endotheliase 2 splice variants. Each variant includes three repetitive sequences composed of ASPAGTPPGRASP (SEQ ID NO. 14) a sequence motif for N-myristoylation modification just before the transmembrane domain.
Figure 1:
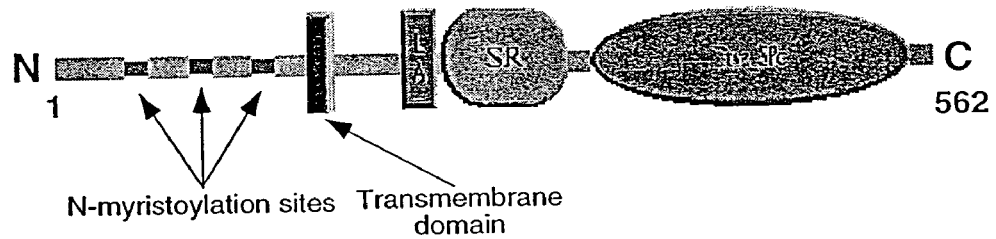

Unless defined otherwise, all technical and scientific terms used herein have the same meaning as is commonly understood by one of ordinary skill in the art to which this invention belongs. All patents, applications, published applications and other publications and sequences from GenBank and other data bases referred to herein are incorporated by reference in their entirety.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

As used herein, angiogenesis is intended to broadly encompass the totality of processes directly or indirectly involved in the establishment and maintenance of new vasculature (neovascularization), including, but not limited to, neovascularization associated with tumors.

As used herein, anti-angiogenic treatment or agent refers to any therapeutic regimen and compound, when used alone or in combination with other treatment or compounds, that can alleviate, reduce, ameliorate, prevent, or place or maintain in a state of remission of clinical symptoms or diagnostic markers associated with undesired and/or uncontrolled angiogenesis. Thus, for purposes herein an anti-angiogenic agent refers to an agent that inhibits the establishment or maintenance of vasculature. Such agents include, but are not limited to, anti-tumor agents, and agents for treatments of other disorders associated with undesirable angiogenesis, such as diabetic retinopathies, restenosis, hyperproliferative disorders and others.

As used herein, non-anti-angiogenic anti-tumor agents refer to anti-tumor agents that do not act primarily by inhibiting angiogenesis.

As used herein, pro-angiogenic agents are agents that promote the establishment or maintenance of the vasculature. Such agents include agents for treating cardiovascular disorders, including heart attacks and strokes.

As used herein, undesired and/or uncontrolled angiogenesis refers to pathological angiogenesis wherein the influence of angiogenesis stimulators outweighs the influence of angiogenesis inhibitors. As used herein, deficient angiogenesis refers to pathological angiogenesis associated with disorders where there is a defect in normal angiogenesis resulting in aberrant angiogenesis or an absence or substantial reduction in angiogenesis.

As used herein, endotheliase refers to a mammalian protein, including humans, that has a transmembrane domain and is expressed on the surface of endothelial cells and includes a protease domain, particularly an extracellular protease domain, and is preferably a serine protease. Thus, reference, for example, to endotheliase encompasses all proteins encoded by the endotheliase gene family, or an equivalent molecule obtained from any other source or that has been prepared synthetically or that exhibits the same activity. The endotheliase gene family are transmembrane proteases expressed in endothelial cells. These proteases include serine proteases. When more particularity is need, it refers to proteins that have these features and also include a protease domain that exhibits sequence homology to the endotheliases 1 and 2 exemplified herein. Endotheliase 1 and 2, for example exhibit about 40% or 45% identity. Sequence homology means sequence identity along its length when aligned to maximize identity of at least about 25%, 40%, 60%, 80%, 90% or greater number of residues. Sequence homology also is assessed by determining whether the encoding sequences of nucleic acids hybridize under conditions of at least moderate, or for more closely related proteins, high stringency to the nucleic acid molecules provided herein or to those that encode the same proteins but differ in sequence by virtue of the degeneracy of the genetic code. In addition, endotheliases encompass endotheliases with conservative amino acid substitutions, such as those set forth in Table 1, that do not substantially alter its proteolytic activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p. 224). Also included within the definition, is the catalytically active fragment of an endotheliase.

As used herein, the protease domain of an endotheliase refers to the polypeptide portion of the endotheliase that is the extracellular portion that exhibits protease activity. The protease domain is a polypeptide that includes at least the minimum number of amino acids, generally more than 50 or 100, required for protease activity. Protease activity may be assessed empirically, such as by testing the polypeptide for its ability to act as a protease. Assays, such as in the assays described in the EXAMPLES, except employing a known substrate in place of the test compounds as described in the Examples may be used. Furthermore, since proteases, particularly serine proteases, have characteristic structures and sequences or motifs, the protease domain may be readily identified by such structure and sequence or motif.

As used herein, the portion of protease domain of endotheliase refers to the protease domain of endotheliase that is located within or is the extracellular domain of an endotheliase and exhibits serine proteolytic activity. Hence it is at least the minimal portion of the extracellular domain that exhibits proteolytic activity as assessed by standard assays. An exemplary protease domain of an endotheliase is set forth in SEQ ID No. 2 and as amino acids 321-562 and 321-688 of SEQ ID Nos. 4 and 6. Smaller portions thereof that retain protease activity are contemplated. The protease domains vary in size and constitution, including insertions and deletions in surface loops. Such domains exhibit conserved structure, including at least one structural feature, such as the active site triad, primary specificity pocket, oxyanion hole and/or other features of serine protease domains of proteases. Thus, for purposes herein, the protease domain is a portion of an endotheliase, as defined herein, but is homologous in terms of structural features and retention of sequence of similarity or homology the protease domain of chymotrypsin or trypsin.

As used herein, homologous means about greater than about 25% sequence identity. By sequence identity, the number of conserved amino acids as determined by standard alignment algorithms programs, and used with default gap penalties established by each supplier. Also homology may be assessed by conserved nucleic acid sequence, which includes anything that hybridizes under at least low stringency conditions and encodes the domain. Similarly nucleic acid sequence alignment programs are commercially available (DNAStar "MegAlign" program (Madison, Wis.) and the University of Wisconsin Genetics Computer Group (UWG) "Gap" program (Madison Wis.)). Substantially homologous nucleic acid molecules would hybridize typically at moderate stringency or at high stringency all along the length of the nucleic acid of interest. Also contemplated are nucleic acid molecules that contain degenerate codons in place of codons in the hybridizing nucleic acid molecule.

As used herein, recitation that a polypeptide consists essentially of the protease domain means that the only endotheliase portion of the polypeptide is a protease domain or a catalytically active portion thereof. The polypeptide may optionally include additional non-endotheliase-derived sequences of amino acids.

As used herein, pro-angiogenic treatment or agent refers to any therapeutic regimen and compound, when used alone or in combination with other treatment or compounds, that can alleviate, reduce, ameliorate, prevent, or place or maintain in a state of remission of clinical symptoms or diagnostic markers associated with deficient angiogenesis.

As used herein, domain refers to a portion of a molecule, e.g., proteins or nucleic acids, that is structurally and/or functionally distinct from other portions of the molecule.

As used herein, protease refers to an enzyme catalyzing hydrolysis of proteins or peptides.

As used herein, serine protease refers to a diverse family of proteases wherein a serine residue is involved in the hydrolysis of proteins or peptides. The serine residue can be part of the catalytic triad mechanism, which includes a serine, a histidine and an aspartic acid in the catalysis, or be part of the hydroxyl/ε-amine or hydroxyl/α-amine catalytic dyad mechanism, which involves a serine and a lysine in the catalysis. Examples of serine proteases include, but are not limited to, chymotrypsin, trypsin, plasmin, thrombin and elastase.

As used herein, catalytic activity refers to the activity of the endotheliase as a proteases. Function of the endotheliase refers to its function in endothelial cell biology, including promotion of angiogenesis or involvement in angiogenesis.

As used herein, nucleic acids include DNA, RNA and analogs thereof, including protein nucleic acids (PNA) and mixture thereof. Nucleic acids can be single or double stranded. When referring to probes or primers, optionally labeled, with a detectable label, such as a fluorescent or radiolabel, single-stranded molecules are contemplated. Such molecules are typically of a length such that they are statistically unique of low copy number (typically less than 5, preferably less than 3) for probing or priming a library. Generally a probe or primer contains at least 14, 16 or 30 contiguous of sequence complementary to or identical a gene of interest. Probes and primers can be 10, 20, 30, 50, 100 or more nucleic acids long.

As used herein, nucleic acid encoding a fragment or portion of an endotheliase refers to a nucleic acid encoding only the recited fragment or portion of endotheliase protein, and not the other contiguous portions of the endotheliase as a continuous sequence.

As used herein, heterologous or foreign DNA and RNA are used interchangeably and refer to DNA or RNA that does not occur naturally as part of the genome in which it is present or which is found in a location or locations in the genome that differ from that in which it occurs in nature. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed. Any DNA or RNA that one of skill in the art would recognize or consider as heterologous or foreign to the cell in which it is expressed is herein encompassed by heterologous DNA. Heterologous DNA and RNA may also encode RNA or proteins that mediate or alter expression of endogenous DNA by affecting transcription, translation, or other regulatable biochemical processes.

As used herein, operative linkage of heterologous DNA to regulatory and effector sequences of nucleotides, such as promoters, enhancers, transcriptional and translational stop sites, and other signal sequences refers to the relationship between such DNA and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA in reading frame.

As used herein, a sequence complementary to at least a portion of an RNA, with reference to antisense oligonucleotides, means a sequence having sufficient complementarily to be able to hybridize with the RNA, preferably under moderate or high stringency conditions, forming a stable duplex; in the case of double-stranded endotheliase antisense nucleic acids, a single strand of the duplex DNA may thus be tested, or triplex formation may be assayed. The ability to hybridize depends on the degree of complementarily and the length of the antisense nucleic acid. Generally, the longer the hybridizing nucleic acid, the more base mismatches with an endotheliase encoding RNA it can contain and still form a stable duplex (or triplex, as the case may be). One skilled in the art can ascertain a tolerable degree of mismatch by use of standard procedures to determine the melting point of the hybridized complex.

For purposes herein, conservative amino acid substitutions may be made in any of endotheliases or protease domains thereof provided that the resulting protein exhibits protease activity. Amino acid substitutions are preferably made in accordance with those set forth in TABLE 1 as follows:

TABLE 1

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, a splice variant refers to a variant produced by differential processing of a primary transcript of genomic DNA that results in more than one type of mRNA.

As used herein, a probe or primer based on a nucleotide sequence disclosed herein, includes at least 10, 14, preferably at least 16 or 30 or 100 contiguous sequence of nucleotides of SEQ ID Nos. 1, 3 or 5.

As used herein, amelioration of the symptoms of a particular disorder by administration of a particular pharmaceutical composition refers to any lessening, whether permanent or temporary, lasting or transient that can be attributed to or associated with administration of the composition.

As used herein, antisense polynucleotides refer to synthetic sequences of nucleotide bases complementary to mRNA or the sense strand of double stranded DNA. Admixture of sense and antisense polynucleotides under appropriate conditions leads to the binding of the two molecules, or hybridization. When these polynucleotides bind to (hybridize with) mRNA, inhibition of protein synthesis (translation)

occurs. When these polynucleotides bind to double stranded DNA, inhibition of RNA synthesis (transcription) occurs. The resulting inhibition of translation and/or transcription leads to an inhibition of the synthesis of the protein encoded by the sense strand. Antisense nucleic acid molecule typically contain a sufficient number of nucleotides to specifically bind to a target nucleic acid, generally at least 5 contiguous nucleotides, often at least 14 or 16 or 30 contiguous nucleotides or modified nucleotides complementary to the coding portion of a nucleic acid molecule that encodes a gene of interest, in this instance a gene encoding an endotheliase.

As used herein, an array refers to a collection of elements, such as antibodies, containing three or more members. An addressable array is one in which the members of the array are identifiable, typically by position on a solid phase support. Hence, in general the members of the array will be immobilized to discrete identifiable loci on the surface of a solid phase.

As used herein, antibody refers to an immunoglobulin, whether natural or partially or wholly synthetically produced, including any derivative thereof that retains the specific binding ability the antibody. Hence antibody includes any protein having a binding domain that is homologous or substantially homologous to an immunoglobulin binding domain. Antibodies include members of any immunoglobulin claims, including IgG, IgM, IgA, IgD and IgE.

As used herein, antibody fragment refers to any derivative of an antibody that is less then full length, retaining at least a portion of the full-length antibody's specific binding ability. Examples of antibody fragments include, but are not limited to, Fab, Fab', F(ab)$_2$, single-chain Fvs (scFV), FV, dsFV diabody and Fd fragments. The fragment can include multiple chains linked together, such as by disulfide bridges. An antibody fragment generally contains at least about 50 amino acids and typically at least 200 amino acids.

As used herein, an Fv antibody fragment is composed of one variable heavy domain ($V_H$) and one variable light domain linked by noncovalent interactions.

As used herein, a dsFV refers to an Fv with an engineered intermolecular disulfide bond, which stabilizes the $V_H$-$V_L$ pair.

As used herein, an F(ab)$_2$ fragment is an antibody fragment that results from digestion of an immunoglobulin with pepsin at pH 4.0-4.5; it may be recombinantly produced.

As used herein, Fab fragments is an antibody fragment that results from digestion of an immunoglobulin with papain; it may be recombinantly produced.

As used herein, scFVs refer to antibody fragments that contain a variable light chain ($V_L$) and variable heavy chain ($V_H$) covalently connected by a polypeptide linker in any order. The linker is of a length such that the two variable domains are bridged without substantial interference. Preferred linkers are (Gly-Ser)$_n$ residues with some Glu or Lys residues dispersed throughout to increase solubility.

As used herein, humanized antibodies refer to antibodies that are modified to include human sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, diabodies are dimeric scFV; diabodies typically have shorter peptide linkers than scFvs, and they preferentially dimerize.

As used herein, humanized antibodies refer to antibodies that are modified to include human sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, production by recombinant means by using recombinant DNA methods means the use of the well known methods of molecular biology for expressing proteins encoded by cloned DNA.

As used herein the term assessing is intended to include quantitative and qualitative determination in the sense of obtaining an absolute value for the activity of an endotheliase, or a domain thereof, present in the sample, and also of obtaining an index, ratio, percentage, visual or other value indicative of the level of the activity. Assessment may be direct or indirect and the chemical species actually detected need not of course be the proteolysis product itself but may for example be a derivative thereof or some further substance.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in in vitro systems designed to test or use such activities. Thus, for purposes herein the biological activity of a luciferase is its oxygenase activity whereby, upon oxidation of a substrate, light is produced.

As used herein, a combination refers to any association between two or more items.

As used herein, a composition refers to any mixture. It may be a solution, a suspension, liquid, powder, a paste, aqueous, non-aqueous or any combination thereof.

As used herein, a conjugate refers to the compounds provided herein that include one or more endotheliases, or domains thereof, and one or more targeting agents. These conjugates include those produced by recombinant means as fusion proteins, those produced by chemical means, such as by chemical coupling, through, for example, coupling to sulfhydryl groups, and those produced by any other method whereby at least one endotheliase, or a domain thereof, is linked, directly or indirectly via linker(s) to a targeting agent.

As used herein, a targeting agent, is any moiety, such as a protein or effective portion thereof, that provides specific binding of the conjugate to a cell surface receptor, which preferably internalizes the conjugate or endotheliase portion thereof. A targeting agent may also be one that promotes or facilitates, for example, affinity isolation or purification of the conjugate; attachment of the conjugate to a surface; or detection of the conjugate or complexes containing the conjugate.

As used herein, an antibody conjugate refers to a conjugate in which the targeting agent is an antibody.

As used herein, humanized antibodies refer to antibodies that are modified to include human sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, derivative or analog of a molecule refers to a portion derived from or a modified version of the molecule.

As used herein, fluid refers to any composition that can flow. Fluids thus encompass compositions that are in the form of semi-solids, pastes, solutions, aqueous mixtures, gels, lotions, creams and other such compositions.

As used herein, an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein equivalent, when referring to two sequences of nucleic acids means that the two sequences in question encode the same sequence of amino acids or equivalent proteins. When equivalent is used in referring to two proteins or peptides, it means that the two proteins or peptides have substantially the same amino acid sequence with only conservative amino acid substitutions (see, e.g., Table 1, above) that do not substantially alter the activity or function of the protein or peptide. When equivalent refers to a property, the property does not need to be present to the same extent [e.g., two peptides can exhibit different rates of the same type of enzymatic activity], but the activities are preferably substantially the same. Complementary, when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein, inhibitor of an endotheliase encompasses any substances that prohibit or decrease production, post-translational modification(s), maturation, or membrane localization of the endotheliase, or any substances that interfere with or decrease the proteolytic efficacy of the endotheliase.

As used herein, a method for treating or preventing disease or disorder associated with undesired and/or uncontrolled angiogenesis means that the diseases and the symptoms associated with the undesired and/or uncontrolled angiogenesis are alleviated, reduced, ameliorated, prevented, placed in a state of remission, or maintained in a state of remission. It also means that the hallmarks of pathological angiogenesis are eliminated, reduced or prevented by the treatment. Non-limiting examples of the hallmarks of the pathological angiogenesis include uncontrolled degradation of the basement membrane and proximal extracellular matrix of the endothelial cells, migration, division, and organization of the endothelial cells into new functioning capillaries, and the persistence of such functioning capillaries.

As used herein, a method for treating or preventing disease or disorder associated with deficient angiogenesis means that the diseases and the symptoms associated with the deficient angiogenesis are alleviated, reduced, ameliorated, prevented, placed in a state of remission, or maintained in a state of remission.

As used herein, operatively linked or operationally associated refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, *J. Biol. Chem.*, 266: 19867-19870 (1991)) can be inserted immediately 5' of the start codon and may enhance expression. The desirability of (or need for) such modification may be empirically determined.

As used herein, pharmaceutically acceptable salts, esters or other derivatives of the conjugates include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

As used herein, a drug identified by the screening methods provided herein refers to any compound that is a candidate for use as a therapeutic or as lead compound for designed a therapeutic. Such compounds can be small molecules, including small organic molecules, peptides, peptide mimetics, antisense molecules, antibodies, fragments of antibodies, recombinant antibodies and other such compound which can serve as drug candidate or lead compound.

As used herein, production by recombinant means by using recombinant DNA methods means the use of the well known methods of molecular biology for expressing proteins encoded by cloned DNA.

As used herein, a promoter region or promoter element refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters.

As used herein, a receptor refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants [such as on viruses, cells, or other materials], drugs, polynucleotides, nucleic acids, peptides, cofactors, lectins, sugars, polysaccharides, cells, cellular membranes, and organelles.

Examples of receptors and applications using such receptors, include but are not restricted to:

a) enzymes: specific transport proteins or enzymes essential to survival of microorganisms, which could serve as targets for antibiotic [ligand] selection;

b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments such as for auto-immune diseases c) nucleic acids: identification of ligand, such as protein or RNA, binding sites;

d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant [see, e.g., U.S. Pat. No. 5,215,899];

e) hormone receptors: determination of the ligands that bind with high affinity to a receptor is useful in the development of hormone replacement therapies; for example, identification of ligands that bind to such receptors may lead to the development of drugs to control blood pressure; and f) opiate receptors: determination of ligands that bind to the opiate receptors in the brain is useful in the development of less-addictive replacements for morphine and related drugs.

As used herein, sample refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein: stringency of hybridization in determining percentage mismatch is as follows:
1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

It is understood that equivalent stringencies may be achieved using alternative buffers, salts and temperatures.

The term substantially identical or homologous or similar varies with the context as understood by those skilled in the relevant art and generally means at least 70%, preferably means at least 80%, more preferably at least 90%, and most preferably at least 95% identity.

As used herein, substantially identical to a product means sufficiently similar so that the property of interest is sufficiently unchanged so that the substantially identical product can be used in place of the product.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, target cell refers to a cell that expresses an endotheliase naturally.

As used herein, test substance refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on an endotheliase, or a domain thereof, is determined by the disclosed and/or claimed methods herein.

As used herein, the terms a therapeutic agent, therapeutic regimen, radioprotectant, chemotherapeutic mean conventional drugs and drug therapies, including vaccines, which are known to those skilled in the art. Radiotherapeutic agents are well known in the art.

As used herein, treatment means any manner in which the symptoms of a conditions, disorder or disease are ameliorated or otherwise beneficially altered. Treatment also encompasses any pharmaceutical use of the compositions herein.

As used herein, vector (or plasmid) refers to discrete elements that are used to introduce heterologous DNA into cells for either expression or replication thereof. The vectors typically remain episomal, but may be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, protein binding sequence refers to a protein or peptide sequence that is capable of specific binding to other protein or peptide sequences generally, to a set of protein or peptide sequences or to a particular protein or peptide sequence.

As used herein, epitope tag refers to a short stretch of amino acid residues corresponding to an epitope to facilitate subsequent biochemical and immunological analysis of the epitope tagged protein or peptide. Epitope tagging is achieved by appending the sequence of the epitope tag to the protein-encoding sequence in an appropriate expression vector. Epitope tagged proteins can be affinity purified using highly specific antibodies raised against the tags.

As used herein, metal binding sequence refers to a protein or peptide sequence that is capable of specific binding to metal ions generally, to a set of metal ions or to a particular metal ion.

As used herein, a composition refers to a any mixture. It may be a solution, a suspension, liquid, powder, a paste, aqueous, non-aqueous or any combination thereof.

As used herein, a combination refers to any association between two or among more items.

As used herein, fluid refers to any composition that can flow. Fluids thus encompass compositions that are in the form of semi-solids, pastes, solutions, aqueous mixtures, gels, lotions, creams and other such compositions.

For clarity of disclosure, and not by way of limitation, the detailed description is divided into the subsections that follow.

B. Endotheliase Proteins and Derivatives and Analogs

Protease Involvement in Angiogenesis

In the initial stages of angiogenesis, microvascular endothelial cells of preexisting blood vessels locally degrade the underlying basal lamina and invade into the stroma of the tissue to be vascularized. It has been shown that this process requires a wide array of degradative enzymes (Mignatti and Rifkin, *Enzyme Protein,* 49(1-3):117-37 (1996)). Components of the plasminogen activator (PA)-plasmin system and the matrix metalloproteinase (MMP) family play important roles. PAs trigger a proteinase cascade that results in the generation of high local concentrations of plasmin and active MMPs. This increase in proteolytic activity has three major consequences: it permits extracellular matrix degradation and invasion of the vessel basal lamina, generates extracellular matrix (ECM) degradation products that are chemotactic for endothelial cells, and activates and mobilizes growth factors localized in the ECM. Five proteases, urokinase-type plasminogen activator, factor XII, protein C, trypsinogen IV, and a membrane-type serine protease 1 (MTSP1) that may be involved in these processes have been identified.

At least nine different MMPs have been identified. Among these are gelatinase A, which degrades collagen types IV and V, elastin and laminin and which is frequently overexpressed in stromal cells of malignant tumors (Vassalli and Pepper, *Nature,* 370:14-5 (1994)). Nucleic acid encoding a matrix metalloproteinase with a potential transmembrane domain has been cloned (Sato et al., *Nature,* 370:61-5 (1994)). Expression of the cloned gene product on the cell surface induces specific activation of pro-gelatinase A in vitro and enhances cellular invasion of the reconstituted basement membrane. Tumor cells of invasive lung carcinomas, which contain activated forms of gelatinase A, were found to express the transcript and the gene product. Inhibition of protease activity through the use of wild-type and engineered ecotins results in inhibition of rat prostate differentiation and retardation of the growth of human PC-3 prostatic cancer tumors (see, Takeuchi et al. *Proc. Natl. Acad. Sci.* (*USA*), 96(20):11054-61 (1999)).

Thus, endothelial cells and proteases play key roles in angiogenesis and related processes. Furthermore, proteases can serve as therapeutic targets and points of intervention in processes relying on the protease activities.

Aberrant angiogenesis and processes related thereto have a role in a variety of disorders, including: cancers, diabetic retinopathies, hyperproliferative disorders, restenosis and others. As provided herein, because proteases are involved either directly or indirectly in angiogenesis, which is aberrant in a variety of disorders, altering the activity of proteases involved in angiogenesis could treat the disorders. Thus, proteases involved in angiogenesis can serve as therapeutic targets and also in drug screening methodologies to identify compounds that modulate, particularly inhibit, angiogenesis.

Provided herein is a class of proteases, designated herein as endotheliases. The proteases are endothelial cell transmembrane proteins, which, in view of the role(s) of endothelial cells and proteases in angiogenesis and related processes, are directly or indirectly involved in the process of angiogenesis or processes related thereto, including tumor formation and metastasis. Thus, these proteases are therapeutic, diagnostic, prognostic targets for intervention in the process of angiogenesis, either for inhibition or activation thereof. These proteases, and/or the protease domains thereof, extracellular domains, provide targets for screening for compounds that modulate angiogenesis and for identifying non-anti-angiogenic anti-tumor agents.

The endotheliases provided herein and the screening methods provided herein permit discovery of candidate compounds that modulate processes involved in the establishment and maintenance of the vasculature. The methods provide a means to select compounds that selectively bind to the endotheliases or interact therewith resulting an increase or decrease in the protease activity of the endotheliase. Since the endotheliases occur on endothelial cells, which are intimately involved in processes related to establishment and maintenance of the vasculature, the compounds identified by the methods herein can have activity as anti-angiogenic or pro-angiogenic agents, and also as non-anti-angiogenic anti-tumor agents.

Endotheliases

Thus, provided herein are endotheliases, including protease domains thereof. As noted, endotheliases are endothelial cell transmembrane proteins that include an extracellular domain that exhibits protease activity. By virtue of its expression on endothelial cells, these proteases participate directly or indirectly in processes involved in angiogenesis.

Substantially purified protease domains of endotheliase proteins and derivatives or analog thereof that can be bound by an antibody directed against such protease domain are provided. Also included are substantially purified protein that contain amino acid sequences that have at least 40%, more preferably 60% or greater, identity to the protease domain of the endotheliase proteins exemplified herein, where the percentage identity is determined over an amino acid sequence of identical size to the protease domain. More preferably, the sequence identity is at least 90% identical.

In exemplary embodiments, two different endotheliases, including variant forms thereof, are provided. These include an endotheliase 1 and two splice variants of an endotheliase 2. Other members of the family may be identified by probing for genes or searching libraries for genes that have sequence identity, particularly at least 40%, 60%, 80%, 90% or greater sequence identity to the protease domain of an endotheliase identified herein, or that hybridize under conditions of high stringency to the full-length of the nucleic acid encoding a protease domain of an endotheliase provided herein.

Alternatively, and as a way of identifying endotheliases that may have lower sequence identity, an endotheliase may be identified by the methods exemplified herein, such by identifying ESTs or other nucleic acid fragments that have sequences similar to a protease and then using such fragments as probes to identify and select cDNA clones encoding full-length proteases or protease domains thereof, identifying those that have the characteristics of transmembrane proteins, and then determining the gene expression profile to identify those that are expressed on the surface of endothelial cells. Encoded proteins that have protease activity, that include a transmembrane domain and an extracellular domain, and that are expressed in endothelial cells are endotheliases. Any method for identification of genes encoding proteins (or proteins) that encode a transmembrane protease expressed on an endothelial cell is contemplated herein.

As described below, exemplary nucleic acid molecules encoding an endotheliase and/or protease domain therein are provided. Full-length clones encoding endotheliase or a protease domain thereof can be obtained by any methods known in the art, including, but not limited to, PCR amplification using synthetic primers that hybridize to the 3' and 5' ends of an endotheliase and/or by cloning from a cDNA or genomic library using a PCR amplification product or an oligonucleotide specific for the gene sequence Homologs (e.g., nucleic acids of the above-listed genes of species other than human) or other related sequences (e.g., paralogs) can be obtained by low, moderate or high stringency hybridization with all or a portion of the particular sequence provided as a probe using methods well known in the art for nucleic acid hybridization and cloning.

For recombinant expression of one or more of the proteins, the nucleic acid containing all or a portion of the nucleotide sequence encoding the protein can be inserted into an appropriate expression vector, i.e., a vector that contains the necessary elements for the transcription and translation of the inserted protein coding sequence. The necessary transcriptional and translational signals can also be supplied by the native promoter for endotheliase genes, and/or their flanking regions.

Full-length endotheliases and domains thereof, particularly the protease domain of an endotheliase are provided herein. The domain or portion there of the endotheliase contains at least 10, 20, 30, 40, or 50 contiguous amino acids of an endotheliase. In specific embodiments, such domains or fragments are not larger than 35, 100, 200 or 500 amino acids. Derivatives or analogs of endotheliases include but are not limited to molecules containing regions that are substantially homologous to endotheliase in various embodiments, at least 30%, 40%, 50%, 60%, 70%, 80%, 90% or 95% identity over an amino acid sequence of identical size or when compared to an aligned sequence in which the alignment is done by a computer homology program known in the art or whose encoding nucleic acid is capable of hybridizing to a sequence encoding endotheliase under stringent, moderately stringent, or nonstringent conditions.

Endotheliase derivatives can be made by altering their sequences by substitutions, additions or deletions that provide for functionally equivalent molecules. Due to the degeneracy of nucleotide coding sequences, other DNA sequences which encode substantially the same amino acid sequence as an endotheliase gene can be used herein. These include but are not limited to nucleotide sequences containing all or portions of endotheliase genes that are altered by the substitution of different codons that encode the amino acid residue within the sequence, thus producing a silent change. Endotheliase derivatives include, but are not limited to, those containing, as a primary amino acid sequence, all or part of the amino acid sequence of endotheliase, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Exemplary of the endotheliase provided herein are endotheliase 1 and endotheliase 2.

Endotheliase 1 and Nucleic Acids Encoding Endotheliase 1 Nucleic Acids

The identification and cloning of nucleic acids encoding the protease domain of endotheliase 1 is described in Example 1. Provided herein is a nucleic acid that encodes the protease domain of an endotheliase 1. Such nucleic acid molecule encodes the sequence of amino acids set forth in SEQ ID NO: 2; it also includes the amino acid 190- or 191-422 of sequence of SEQ ID NO 22; (the Arg is optionally included). Also provided herein are nucleic acids that hybridize to a nucleic acid containing the sequence of nucleotides set forth in the SEQ ID No. 1. Hybridization is preferably under moderate conditions and more preferably high stringency conditions and is such that the nucleic acid of interest hybridizes along its full length to the nucleic acid that encodes the protease domain endotheliase 1 and is considered to be an endotheliase 1 by virtue of its expression in endothelial cells, activity as a protease and similarity as assessed by hybridization or by having sequence identity of at least about 60%, more preferably more than about 75% sequence identity, more preferably more than about 90% to the protease domain of endotheliase 1 exemplified herein. Such proteins will also exhibit protease activity. Also contemplated herein are proteins that include conservative amino acid sequence changes, such as those set forth in Table 1 above, and retain protease activity.

The endotheliase 1 protease domain and encoding nucleic acid is contemplated for use in the methods and cells and vectors described herein. The protease domain may be used as purified protein or may be part of a larger protein, such as the full length endotheliase 1.

Also contemplated for use in the methods, vectors and cells is a full-length endotheliase 1. Exemplary of full-length endotheliase are endotheliases that include the sequence of amino acids set forth in SEQ ID No. 22, which provides full length endotheliases (see, International PCT application No. WO 00/50061. International PCT application No. WO 00/50061 provides a gene designated DESC1 used for diagnosis of squamous cell carcinoma or prostate cancer. DESC1 is shown herein to encode an endotheliase 1. DESC1 and the encoded protein (see SEQ ID No. 22) are contemplated for use in the methods, cells and vectors provided herein. The PCT application does not suggest using the protease domain thereof for any purpose.

Proteins

Provided herein are protease domains of an endotheliase, including endotheliase 1. A substantially purified protease domain of an endotheliase protein that is encoded by the nucleic acid molecules that encode the nucleic acids are provided. In particular, the protease domain contains the sequence of amino acids set forth in SEQ ID No. 2 or a fragment thereof that exhibits protease activity or contains a sequence of amino acids that hybridizes to a nucleic acid molecule that encodes the protein of SEQ ID NO. 2.

In one exemplary embodiment, the substantially purified protease domain is encoded by the sequence of nucleic acids set forth in SEQ. ID No. 1 or hybridizes thereto along its full length under high stringency conditions and has activity as a protease. In other embodiments, a substantially purified derivative or analog of the protease domain of the endotheliase protein is provided, which derivative or analog is able to be bound by an antibody directed against such protease domain.

In another embodiment, the substantially purified protein contains a sequence of amino acids that has at least 60% identity to the protease domain of the endotheliase 1 protein is provided, wherein the percentage identity is determined over an amino acid sequence of identical size to the protease domain. More preferably, the sequence identity is at least 90% identical.

In specific aspects, the protease domain peptide, derivatives or analogs of the protease domain of the endotheliase protein are from animals, including mammals, such as, but are not limited to, mouse, rat, chicken and human origin and is functionally active, i.e., capable of exhibiting one or more functional activities associated with the domains, e.g., serine protease activity, immunogenicity or antigenicity.

Endotheliase 2 and Nucleic Acids Encoding Endotheliase 2

The cloning of endotheliase 2 and expression profile thereof is described in Example 2. Two splice variant forms of endotheliase 2 designated endotheliase 2-S and endotheliase 2-L are also provided (see FIG. 1 for the domain organization thereof; see also EXAMPLE 2). The open reading frame of the nucleic acid encoding endotheliase 2-S (SEQ ID No. 3) is composed of 1,689 bp, which translates to a 562-amino acid protein (SEQ ID No. 4), while the ORF of endotheliase 2-L is composed of 2,067 bp (SEQ ID No. 5), which translates to a 688-amino acid protein (SEQ ID No. 6).

The nucleic acid encoding the protease domain of endotheliase 2-S is composed of 729 bp which translates to a 242-amino acid protein (amino acids 321-562 of SEQ ID Nos. 3 and 4), while that of endotheliase 2-L is composed of 1,107 bp, which translates to a 368-amino acid protein (amino acids 321-688 of SEQ ID Nos. 5 and 6). The domain organization of each form is depicted in FIG. 1.

The full-length and protease domains of endotheliase 2 as well as other domains (see FIG. 1) are provided herein as are cells, vectors and methods that use the proteins and/or encoding nucleic acid.

Also provided herein are nucleic acids that hybridize to a nucleic acid containing the sequence of nucleotides set forth in SEQ. ID No. 3 or 5. Hybridization is preferably effected under moderate conditions and more preferably high stringency conditions and is such that the nucleic acid of interest hybridizes along its full length the nucleic acid that encodes the protease domain of endotheliase 2 and is considered to encode an endotheliase 2 by virtue of endogenous expression of the protein in endothelial cells, activity as a protease and similarity as assessed by hybridization or by having sequence identify of at least about 60%, more preferably more than about 85% sequence identity, more preferably more than about 90% to the protease domain of endotheliase 2 exemplified herein. Such encoded proteins will also exhibit protease activity. The nucleic acids are contemplated for use in vectors, cells and methods provided herein.

Endotheliase-2 Proteins

Any and all of the above-noted endotheliases and/or protease domains thereof, such as those that include the sequences of amino acids in SEQ ID Nos. 2, 4, 6 and 22 or are encoded by nucleic acid that hybridize thereto under the conditions as described above are contemplated for use in the methods herein. Also contemplated herein are proteins that include conservative amino acid sequence changes, such as those set forth in Table 1 above, and retain protease activity.

Vectors, Plasmids and Cells that Contain Nucleic Acids Encoding an Endotheliase or Protease Domain Thereof Also provided are vectors that contain nucleic acid encoding the endotheliases. Cells containing the vectors are also provided. The cells include eukaryotic and prokaryotic cells, and the vectors are suitable for use therein.

Prokaryotic and eukaryotic cells, including endothelial cells, containing the vectors are provided. Such cells include bacterial cells, yeast cells, fungal cells. plant cells, insect cells and animal cells. The cells are used to produce an endotheliase or protease domain thereof by growing the above-described cells under conditions whereby the encoded endotheliase or protease domain of the endotheliase is expressed by the cell, and recovering the expressed protease domain protein. For purposes herein, the protease domain is preferably secreted into the medium.

In one embodiment, the vectors include a sequence of nucleotides that encodes a polypeptide that has protease activity and contains all or a portion of only the protease domain, or multiple copies thereof, of an endotheliase are provided. Also provided are vectors that comprise a sequence of nucleotides that encodes the protease domain and additional portions of an endotheliase up to and including a full length endotheliase, as well as multiple copies thereof, are also provided. The vectors may be selected for expression of the endotheliase or protease domain thereof in the cell or such that the endotheliase is expressed as a transmembrane protein. Alternatively, the vectors may include signals necessary for secretion of encoded proteins. When the protease domain is expressed the nucleic acid is preferably linked to a secretion signal, such as the *Saccharomyces cerevisiae* α mating factor signal sequence or a portion thereof.

A variety of host-vector systems may be used to express the protein coding sequence. These include but are not limited to mammalian cell systems infected with virus (e.g. vaccinia virus, adenovirus, etc.); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system used, any one of a number of suitable transcription and translation elements may be used.

Any methods known to those of skill in the art for the insertion of DNA fragments into a vector may be used to construct expression vectors containing a chimeric gene containing of appropriate transcriptional/translational control signals and protein coding sequences. These methods may include in vitro recombinant DNA and synthetic techniques and in vivo recombinants (genetic recombination). Expression of nucleic acid sequences encoding endotheliase, or domains, derivatives, fragments or homologs thereof, may be regulated by a second nucleic acid sequence so that the genes or fragments thereof are expressed in a host transformed with the recombinant DNA molecule(s). For example, expression of the proteins may be controlled by any promoter/enhancer known in the art. In a specific embodiment, the promoter is not native to the genes for endotheliase. Promoters which may be used include but are not limited to the SV40 early promoter (Bernoist and Chambon, *Nature* 290:304-310 (1981)), the promoter contained in the 3' long terminal repeat of Rous sarcoma virus (Yamamoto et al., *Cell* 22:787-797 (1980)), the herpes thymidine kinase promoter (Wagner et al., *Proc. Natl. Acad. Sci. USA* 78:1441-1445 (1981)), the regulatory sequences of the metallothionein gene (Brinster et al., *Nature* 296:39-42 (1982)); prokaryotic expression vectors such as the β-lactamase promoter (Villa-Kamaroff et al., *Proc. Natl. Acad. Sci. USA* 75:3727-3731 1978)) or the tac promoter (DeBoer et al., *Proc. Natl. Acad. Sci. USA* 80:21-25 (1983)); see also "Useful Proteins from Recombinant Bacteria": in Scientific American 242:79-94 (1980)); plant expression vectors containing the nopaline synthetase promoter (Herrar-Estrella et al., *Nature* 303:209-213 (1984)) or the cauliflower mosaic virus 35S RNA promoter (Garder et al., *Nucleic Acids Res.* 9:2871 (1981)), and the promoter of the photosynthetic enzyme ribulose bisphosphate carboxylase (Herrera-Estrella et al., *Nature* 310: 115-120 (1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., *Cell* 38:639-646 (1984); Ornitz et al., *Cold Spring Harbor Symp. Quant. Biol.* 50:399-409 (1986); MacDonald, *Hepatology* 7:425-515 (1987)); insulin gene control region which is active in pancreatic beta cells (Hanahan et al., *Nature* 315:115-122 (1985)), immunoglobulin gene control region which is active in lymphoid cells (Grosschedl et al., *Cell* 38:647-658 (1984); Adams et al., *Nature* 318:533-538 (1985); Alexander et al., *Mol. Cell. Biol.* 7:1436-1444 (1987)), mouse mammary tumor virus control region which is active in testicular, breast, lymphoid and mast cells (Leder et al., *Cell* 45:485-495 (1986)), albumin gene control region which is active in liver (Pinckert et al., *Genes and Devel.* 1:268-276 (1987)), alpha-fetoprotein gene control region which is active in liver (Krumlauf et al., *Mol. Cell. Biol.* 5:1639-1648 (1985); Hammer et al., *Science* 235:53-58 1987)), alpha-1 antitrypsin gene control region which is active in liver (Kelsey et al., *Genes and Devel.* 1:161-171 (1987)), beta globin gene control region which is active in myeloid cells (Mogram et al., *Nature* 315:338-340 (1985); Kollias et al., *Cell* 46:89-94 (1986)), myelin basic protein gene control region which is active in oligodendrocyte cells of the brain (Readhead et al., *Cell* 48:703-712 (1987)), myosin light chain-2 gene control region which is active in skeletal muscle (Sani, *Nature* 314:283-286 (1985)), and gonadotrophic releasing hormone gene control region which is active in gonadotrophs of the hypothalamus (Mason et al., *Science* 234:1372-1378 (1986)).

In a specific embodiment, a vector is used that contains a promoter operably linked to nucleic acids encoding an endotheliase, or a domain, fragment, derivative or homolog, thereof, one or more origins of replication, and optionally, one or more selectable markers (e.g., an antibiotic resistance gene). Expression vectors containing the coding sequences, or portions thereof, of an endotheliase, is made, for example, by subcloning the coding portions into the EcoRI restriction site of each of the three pGEX vectors (glutathione S-transferase expression vectors (Smith and Johnson, *Gene* 7:31-40 (1988)). This allows for the expression of products in the correct reading frame. Preferred vectors and systems for expression of the protease domains of the endotheliases are the *Pichia* vectors, particularly those designed for secretion of the encoded proteins. One exemplary vector is described in the EXAMPLES.

The vectors are introduced into host cells and the proteins expressed therein. Once a recombinant cell expressing an endotheliase protein, or a domain, fragment or derivative thereof, is identified, the individual gene product can be isolated and analyzed. This is achieved by assays based on the physical and/or functional properties of the protein, including, but not limited to, radioactive labeling of the product followed by analysis by gel electrophoresis, immunoassay, cross-linking to marker-labeled product The endotheliase proteins may be isolated and purified by standard methods known in the art (either from natural sources or recombinant host cells expressing the complexes or proteins), including but not restricted to column chromatography (e.g., ion exchange, affinity, gel exclusion, reversed-phase high pressure, fast protein liquid, etc.), differential centrifugation, differential solubility, or by any other standard technique used for the purification of proteins. Functional properties may be evaluated using any suitable assay known in the art.

Alternatively, once an endotheliase or its domain or derivative is identified, the amino acid sequence of the protein can be deduced from the nucleotide sequence of the gene which encodes it. As a result, the protein or its domain or derivative can be synthesized by standard chemical methods known in the art (e.g. see Hunkapiller et al, *Nature* 310:105-111 (1984)).

Manipulations of endotheliase sequences may be made at the protein level. Also contemplated herein are endotheliase proteins, domains thereof, derivatives or analogs or fragments thereof, which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

In specific embodiments, the endotheliases are modified to include a fluorescent label. In other specific embodiments, the endotheliase is modified to have a heterofunctional reagent, such heterofunctional reagents can be used to crosslink the members of the complex.

In addition, domains, analogs and derivatives of an endotheliase can be chemically synthesized. For example, a peptide corresponding to a portion of an endotheliase, which includes the desired domain or which mediates the desired activity in vitro can be synthesized by use of a peptide synthesizer. Furthermore, if desired, nonclassical amino acids or chemical amino acid analogs can be introduced as a substitution or addition into the endotheliase sequence. Non-classical amino acids include but are not limited to the D-isomers of the common amino acids, a-amino isobutyric acid, 4-aminobutyric acid, Abu, 2-aminobutyric acid, $\epsilon$-Abu, e-Ahx, 6-amino hexanoic acid, Aib, 2-amino isobutyric acid, 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

In cases where natural products are suspected of being mutant or are isolated from new species, the amino acid sequence of the endotheliase isolated from the natural source, as well as those expressed in vitro, or from synthesized expression vectors in vivo or in vitro, can be determined from analysis of the DNA sequence, or alternatively, by direct sequencing of the isolated protein. Such analysis may be performed by manual sequencing or through use of an automated amino acid sequenator.

C. Identification and Isolation of Endotheliase Genes

Any method known to those of skill in the art for identification of nucleic acids that encode desired genes may be used. Any method available in the art can be used to obtain a full length (i.e., encompassing the entire coding region) cDNA or genomic DNA clone encoding an endotheliase. In particular, the polymerase chain reaction (PCR) can be used to amplify a sequence identified as being differentially expressed in tissues with aberrant level of angiogenesis, e.g., nucleic acids containing the nucleotide sequences of endotheliase (SEQ. NO: 1, 3, 5 or 22), in a genomic or cDNA library. Oligonucleotide primers that hybridize to sequences at the 3' and 5' termini of the identified sequences can be used as primers to amplify by PCR sequences from a nucleic acid sample (RNA or DNA), preferably a cDNA library, from an appropriate source (e.g., tumor or cancer tissue).

PCR can be carried out, e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to amplify nucleic acid homologs (e.g., to obtain endotheliase sequences from species other than humans or to obtain human sequences with homology to endotheliase) by allowing for greater or lesser degrees of nucleotide sequence similarity between the known nucleotide sequence and the nucleic acid homolog being isolated. For cross species hybridization, low stringency conditions are preferred. For same species hybridization, moderately stringent conditions are preferred. After successful amplification of the nucleic acid containing all or a portion of the identified endotheliase sequence or of a nucleic acid encoding all or a portion of an endotheliase homolog, that segment may be molecularly cloned and sequenced, and used as a probe to isolate a complete cDNA or genomic clone. This, in turn, will permit the determination of the gene's complete nucleotide sequence, the analysis of its expression, and the production of its protein product for functional analysis. Once the nucleotide sequence is determined, an open reading frame encoding the endotheliase gene protein product can be determined by any method well known in the art for determining open reading frames, for example, using publicly available computer programs for nucleotide sequence analysis. Once an open reading frame is defined, it is routine to determine the amino acid sequence of the protein encoded by the open reading frame. In this way, the nucleotide sequences of the entire endotheliase genes as well as the amino acid sequences of endotheliase proteins and analogs may be identified.

Any eukaryotic cell potentially can serve as the nucleic acid source for the molecular cloning of the endotheliase gene. The nucleic acids can be isolated from vertebrate, mammalian, human, porcine, bovine, feline, avian, equine, canine, as well as additional primate sources, insects, plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, a portion of the endotheliase (of any species) gene (e.g., a PCR amplification product obtained as described above or an oligonucleotide having a sequence of a portion of the known nucleotide sequence) or its specific RNA, or a fragment thereof be purified and labeled, and the generated DNA fragments may be screened by nucleic acid hybridization to the labeled probe (Benton and Davis, *Science* 196:180 (1977); Grunstein and Hogness, *Proc. Natl. Acad. Sci. U.S.A.* 72:3961 (1975)). Those DNA fragments with substantial homology to the probe will hybridize. It is also possible to identify the appropriate fragment by restriction enzyme digestion(s) and comparison of fragment sizes with those expected according to a known restriction map if such is available or by DNA sequence analysis and comparison to the known nucleotide sequence of endotheliase. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, antigenic properties, serine protease activity or ability to promote angiogenesis, as known for the endotheliase. If an anti-endotheliase antibody is available, the protein may be identified by binding of labeled antibody to the putatively endotheliase synthesizing clones, in an ELISA (enzyme-linked immunosorbent assay)-type procedure.

Alternatives to isolating the endotheliase genomic DNA include, but are not limited to, chemically synthesizing the gene sequence from a known sequence or making cDNA to the mRNA that encodes the endotheliase protein. For example, RNA for cDNA cloning of the endotheliase gene can be isolated from cells expressing the protein. The identified and isolated nucleic acids can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene, La Jolla, Calif.). The insertion into a cloning vector can, for example, be accomplished by ligating the DNA fragment into a cloning vector which has complementary cohesive termini. I the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and endotheliase gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated endotheliase gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

D. Screening Methods

1. Methods for Screening for Compounds that Modulate the Activity of an Endotheliase Methods for identifying compounds that bind to or interact with an endotheliase, particularly, the protease domain thereof, are provided. The identified compounds are candidates or leads for identification of compounds for treatments of tumors and other disorders and diseases involving aberrant angiogenesis. The endotheliases used in the methods include any endotheliase as defined herein, and preferably use the endotheliases 1 and 2 provided herein, and preferably the protease domains thereof. A variety of methods are provided herein. These methods may be performed in solution or in solid phase reactions in which the endotheliase(s) or protease domain(s) thereof are linked, either directly or indirectly via a linker, to a solid support. Screening assays are described in the Examples, and these assays have been used to identify candidate compounds.

One method include the steps of (a) contacting the endotheliase or protease domain thereof with one or a plurality of test compounds under conditions conducive to interaction between the ligand and the compounds; and (b) identifying one or more compounds in the plurality that specifically binds to the ligand.

Another method provided herein includes the steps of a) contacting an endotheliase or protease domain thereof with a substrate of the endotheliase, and detecting the proteolysis of the substrate, whereby the activity of the endotheliase is assessed; b) contacting the endotheliase with a substrate of the endotheliase in the presence of a test substance, and detecting the proteolysis of the substrate, whereby the activity of the endotheliase is assessed; and c) comparing the activity of the endotheliase assessed in steps a) and b), whereby the activity measured in step a) differs from the activity measured in step b) indicates that the test substance modulates the activity of the endotheliase.

In another embodiment, a plurality of the test substances are screened for simultaneously in the above screening method. In another embodiment, the endotheliase to be screened against is isolated from a target cell. In another embodiment, the test substance is a therapeutic compound, such that a difference of the endotheliase activity measured in the presence and in the absence of the test substance indicates that the target cell responds to the therapeutic compound.

In comparing the activity of an endotheliase in the presence and absence of a test substance to assess whether the test substance is a modulator of the endotheliase, it is unnecessary to assay the activity in parallel, although such parallel measurement is preferred. It is possible to measure the activity of the endotheliase at one time point and compare the measured activity to a historical value of the activity of the endotheliase. For instance, one can measure the activity of the endotheliase in the presence of a test substance and compare with historical value of the activity of the endotheliase measured previously in the absence of the test substance, and vice versa. This can be accomplished, for example, by providing the activity of the endotheliase on an insert or pamphlet provided with a kit for conducting the assay.

Preferably, the endotheliase to be screened against is isolated from a target cell. More preferably, the test substance to be screened for is a therapeutic compound, and whereby a difference of the endotheliase measured in the presence and in the absence of the test substance indicates whether the target cell responds to the test substance.

Combinations and kits containing the combinations optionally including instructions for performing the assays are provided. The combinations include an endotheliase and a substrate of the endotheliase to be assayed; and, optionally reagents for detecting proteolysis of the substrate. The substrates, which are typically proteins subject to proteolysis by a particular endotheliase, can be identified empirically by testing the ability of the endotheliase to cleave the test substrate. Substrates that are cleaved most effectively (i.e., at the lowest concentrations and/or fastest rate or under desirable conditions), are identified.

Additionally provided herein is a kit containing the above-described combination. Preferably, the kit further includes instructions for identifying a modulator of the activity of an endotheliase. Any endotheliase is contemplated as target for identifying modulators of the activity thereof.

A variety of formats and detection protocols are known for performing screening assays. Any such formats and protocols may be adapted for identifying modulators of endotheliase activities. The following includes a discussion of exemplary protocols.

1. High Throughput Screening Assays

Although the above-described assay can be conducted where a single endotheliase is screened against, and/or a single test substance is screened for in one assay, the assay is preferably conducted in a high throughput screening mode, i.e., a plurality of the endotheliases are screened against and/or a plurality of the test substances are screened for simultaneously (See generally, *High Throughput Screening: The Discovery of Bioactive Substances* (Devlin, Ed.) Marcel Dekker, 1997; Sittampalam et al., *Curr. Opin. Chem. Biol.*, 1(3):384-91 (1997); and Silverman et al., *Curr. Opin. Chem. Biol.*, 2(3):397-403 (1998)). For example, the assay can be conducted in a multi-well (e.g., 24-, 48-, 96-, or 384-well), chip or array format.

High-throughput screening (HTS) is the process of testing a large number of diverse chemical structures against disease targets to identify "hits" (Sittampalam et al., *Curr. Opin. Chem. Biol.*, 1(3):384-91 (1997)). Current state-of-the-art HTS operations are highly automated and computerized to handle sample preparation, assay procedures and the subsequent processing of large volumes of data.

Detection technologies employed in high-throughput screens depend on the type of biochemical pathway being investigated (Sittampalam et al., *Curr. Opin. Chem. Biol.*, 1(3):384-91 (1997)). These methods include, radiochemical methods, such as the scintillation proximity assays (SPA), which can be adapted to a variety of enzyme assays (Lerner et al., *J. Biomol. Screening*, 1:135-143 (1996); Baker et al., *Anal. Biochem.*, 239:20-24 (1996); Baum et al., *Anal. Biochem.*, 237:129-134 (1996); and Sullivan et al., *J. Biomol. Screening*, 2:19-23 (1997)) and protein—protein interaction assays (Braunwalder et al., *J. Biomol. Screening*, 1:23-26 (1996); Sonatore et al., *Anal. Biochem.*, 240:289-297 (1996); and Chen et al., *J. Biol. Chem.*, 271:25308-25315 (1996)), and non-isotopic detection methods, including but are not limited to, calorimetric and luminescence detection methods, resonance energy transfer (RET) methods, time-resolved fluorescence (HTRF) methods, cell-based fluorescence assays, such as fluorescence resonance energy transfer (FRET) procedures (see, e.g., Gonzalez et al., *Biophys. J.*, 69:1272-1280 (1995)), fluorescence polarization or anisotropy methods (see, e.g., Jameson et al., *Methods Enzymol.*, 246:283-300 (1995); Jolley, *J. Biomol. Screening*, 1:33-38 (1996); Lynch et al., *Anal. Biochem.*, 247:77-82 (1997)), fluorescence correlation spectroscopy (FCS) and other such methods.

2. Test Substances

Test compounds, including small molecules and libraries and collections thereof can be screened in the above-described assays and assays described below to identify compounds that modulate the activity of an endotheliase. Rational drug design methodologies that rely on computational chemistry may be used to screen and identify candida compounds.

The compounds identified by the screening methods include inhibitors, including antagonists, and may be agonists Compounds for screening are any compounds and collections of compounds available, know or that can be prepared.

a. Selection of Compounds

Compounds can be selected for their potency and selectivity of inhibition of serine proteases, especially endotheliase. As described herein, and as generally known, a target serine protease and its substrate are combined under assay conditions permitting reaction of the protease with its substrate. The assay is performed in the absence of test compound, and in the presence of increasing concentrations of the test compound. The concentration of test compound at which 50% of the serine protease activity is inhibited by the test compound is the $IC_{50}$ value (Inhibitory Concentration) or $EC_{50}$ (Effective Concentration) value for that compound. Within a series or group of test compounds, those having lower $IC_{50}$ or $EC_{50}$ values are considered more potent inhibitors of the serine protease than those compounds having higher $IC_{50}$ or $EC_{50}$ values. The $IC_{50}$ measurement is often used for more simplistic assays, whereas the $EC_{50}$ is often used for more complicated assays, such as those employing cells.

Preferred compounds according to this aspect have an $IC_{50}$ value of 100 nM or less as measured in an in vitro assay for inhibition of endotheliase activity. Especially preferred compounds have an $IC_{50}$ value of less than 100 nM.

The test compounds also are evaluated for selectivity toward a serine protease. As described herein, and as generally known, a test compound is assayed for its potency toward a panel of serine proteases and other enzymes and an $IC_{50}$ value or $EC_{50}$ value is determined for each test compound in each assay system. A compound that demonstrates a low $IC_{50}$ value or $EC_{50}$ value for the target enzyme, e.g., endotheliase, and a higher $IC_{50}$ value or $EC_{50}$ value for other enzymes within the test panel (e.g., urokinase tissue plasminogen activator, thrombin, Factor Xa), is considered to be selective toward the target enzyme. Generally, a compound is deemed selective if its $IC_{50}$ value or $EC_{50}$ value in the target enzyme assay is at least one order of magnitude less than the next smallest $IC_{50}$ value or $EC_{50}$ value measured in the selectivity panel of enzymes.

Presently preferred compounds have an $IC_{50}$ value of 100 nM or less as measured in an in vitro assay for inhibition of urokinase activity. Especially preferred compounds have an $IC_{50}$ value in the in vitro urokinase inhibition assay that is at least one order of magnitude smaller than the $IC_{50}$ value measured in the in vitro tPA inhibition assay. Compounds having a selectivity ratio of $IC_{50}$ u-PA assay: $IC_{50}$ endotheliase assay of greater than 100 are especially preferred.

Compounds are also evaluated for their activity in vivo. The type of assay chosen for evaluation of test compounds will depend on the pathological condition to be treated or prevented by use of the compound, as well as the route of administration to be evaluated for the test compound.

For instance, to evaluate the activity of a compound to reduce tumor growth through inhibition of endotheliase, the procedures described by Jankun et al., *Canc. Res.*, 57:559-563 (1997) to evaluate PAI-1 can be employed. Briefly, the ATCC cell lines DU145 and LnCaP are injected into SCID mice. After tumors are established, the mice are given test compound according to a dosing regime determined from the compound's in vitro characteristics. The Jankun et al. compound was administered in water. Tumor volume measurements are taken twice a week for about five weeks. A compound is deemed active if an animal to which the compound was administered exhibited decreased tumor volume, as compared to animals receiving appropriate control compounds.

Another in vivo experimental model designed to evaluate the effect of p-aminobenzamidine, a swine protease inhibitor, on reducing tumor volume is described by Billström et al., *Int. J. Cancer,* 61:542-547 (1995).

To evaluate the ability of a compound to reduce the occurrence of, or inhibit, metastasis, the procedures described by Kobayashi et al., *Int. J. Canc.,* 57:727-733d (1994) can be employed. Briefly, a murein xenograft selected for high lung colonization potential in injected into C57B1/6 mice i.v. (experimental metastasis) or s.c. into the abdominal wall (spontaneous metastasis). Various concentrations of the compound to be tested can be admixed with the tumor cells in Matrigel prior to injection. Daily i.p. injections of the test compound are made either on days 1-6 or days 7-13 after tumor inoculation. The animals are sacrificed about three or four weeks after tumor inoculation, and the lung tumor colonies are counted. Evaluation of the resulting data permits a determination as to efficacy of the test compound, optimal dosing and route of administration.

The activity of the tested compounds toward decreasing tumor volume and metastasis can be evaluated in a model described in Rabbani et al., *Int. J. Cancer* 63:840-845 (1995) to evaluate their inhibitor. There, Mat LyLu tumor cells were injected into the flank of Copenhagen rats. The animals were implanted with osmotic minipumps to continuously administer various doses of test compound for up to three weeks. The tumor mass and volume of experimental and control animals were evaluated during the experiment, as were metastatic growths. Evaluation of the resulting data permits a determination as to efficacy of the test compound, optimal dosing, and route of administration. Some of these authors described a related protocol in Xing et al., *Canc. Res.,* 57:3585-3593 (1997).

To evaluate the inhibitory activity of a compound toward neovascularization, a rabbit cornea neovascularization model can be employed. Avery et al., *Arch. Ophthalmol.,* 108:1474-1475 (1990) describe anesthetizing New Zealand albino rabbits and then making a central corneal incision and forming a radial corneal pocket. A slow release prostaglandin pellet was placed in the pocket to induce neovascularization. Test compound was administered i.p. for five days, at which time the animals were sacrificed. The effect of the test compound is evaluated by review of periodic photographs taken of the limbus, which can be used to calculate the area of neovascular response and, therefore, limbal neovascularization. A decreased area of neovascularization as compared with appropriate controls indicates the test compound was effective at decreasing or inhibiting neovascularization.

As angiogenesis model used to evaluate the effect of a test compound in preventing angiogenesis is described by Min et al., *Canc. Res.,* 56:2428-2433 (1996). C57BL6 mice receive subcutaneous injections of a Matrigel mixture containing bFGF, as the angiogenesis-inducing agent, with and without the test compound. After five days, the animals are sacrificed and the Matrigel plugs, in which neovascularization can be visualized, are photographed. An experimental animal receiving Matrigel and an effective dose of test compound will exhibit less vascularization than a control animal or an experimental animal receiving a less- or non-effective dose of compound.

An in vivo system designed to test compound for their ability to limit the spread of primary tumors is described by Crowley et al., *Proc. Natl. Acad. Sci.,* 90:5021-5025 (1993). Nude mice are injected with tumor cells (PC3) engineered to express CAT (chloramphenicol acetyltransferase). Compounds to be tested for their ability to decrease tumor size and/or metastases are administered to the animals, and subsequent measurements of tumor size and/or metastatic growths are made. In addition, the level of CAT detected in various organs provides an indication of the ability of the test compound to inhibit metastasis; detection of less CAT in tissues of a treated animal versus a control animal indicates less CAT-expressing cells migrated to that tissue.

In vivo experimental modes designed to evaluate the inhibitory potential of a test serine protease inhibitors, using a tumor cell line F3II, the to be highly invasive, are described by Alonso et al., *Breast Canc. Res. Treat.,* 40:209-223 (1996). This group describes in vivo studies for toxicity determination, tumor growth, invasiveness, spontaneous metastasis, experimental lung metastasis, and an angiogenesis assay.

The CAM model (chick embryo chorioallantoic membrane model), first described by L. Ossowski in 1998 (*J. Cell Biol.,* 107:2437-2445 (1988)), provides another method for evaluating the urokinase inhibitory activity of a test compound. In the CAM model, tumor cells invade through the chorioallantoic membrane containing CAM with tumor cells in the presence of several serine protease inhibitors results in less or no invasion of the tumor cells through the membrane. Thus, the CAM assay is performed with CAM and tumor cells in the presence and absence of various concentrations of test compound. The invasiveness of tumor cells is measured under such conditions to provide an indication of the compound's inhibitory activity. A compound having inhibitory activity correlates with less tumor invasion.

The CAM model is also used in a standard assay of angiogenesis (i.e., effect on formation of new blood vessels (Brooks et al., *Methods in Molecular Biology,* 129:257-269 (1999)). According to this model, a filter disc containing an angiogenesis inducer, such as basic fibroblast growth factor (bFGF) is placed onto the CAM. Diffusion of the cytokine into the CAM induces local angiogenesis, which may be measured in several ways such as by counting the number of blood vessel branch points within the CAM directly below the filter disc. The ability of identified compounds to inhibit cytokine-induced angiogenesis can be tested using this model. A test compound can either be added to the filter disc that contains the angiogenesis inducer, be placed directly on the membrane or be administered systemically. The extent of new blood vessel formation in the presence and/or absence of test compound can be compared using this model. The formation of fewer new blood vessels in the presence of a test compound would be indicative of anti-angiogenesis activity. Demonstration of anti-angiogenesis activity for inhibitors of an endotheliase indicates a role in angiogenesis for that endotheliase.

b. Known Serine Protease Inhibitors

Compounds for screening can be serine protease inhibitors, which can be tested for their ability to inhibit the activity of the endotheliase protein at least partially encoded by a nucleic acid that hybridizes to a DNA having a nucleotide sequence set forth in the SEQ. ID NO:1.

Exemplary, but not limiting serine proteases, are the following known serine protease inhibitors are used in the screening assays: Serine Protease Inhibitor 3 (SPI-3) (Chen, M. C., et al., *Cytokine,* 11(11):856-862 (1999)); Aprotinin (Iijima, R., et al., *J. Biochem. (Tokyo),* 126(5):912-916 (1999)); Kazal-type serine protease inhibitor-like proteins (Niimi, T., et al., *Eur. J. Biochem.,* 266(1):282-292 (1999)); Kunitz-type serine protease inhibitor (Ravichandran, S., et al., *Acta Crystallogr. D. Biol. Crystallogr.*, 55(11):1814-1821 (1999)); Tissue factor pathway inhibitor-2/Matrix-associated serine rotease inhibitor (TFPI-2/MSPI), (Liu, Y., et al., *Arch. Biochem. Biophys.*, 370(1):112-8 (1999)); Bukunin, (Cui, C. Y., et al., *J. Invest. Dermatol.*, 113(2):182-8 (1999)); Nafmostat mesilate (Ryo, R., et al., *Vox Sang.*, 76(4):241-6 (1999)); TPCK (Huang, Y., et al., *Oncogene*, 18(23):3431-9 (1999)); A synthetic cotton-bound serine protease inhibitor (Edwards, J. V., et al., *Wound Repair Regen.*, 7(2):106-18 (1999)); FUT-175 (Sawada, M., et al., *Stroke*, 30(3):644-50 (1999)); Combination of serine protease inhibitor FUT-0175 and thromboxane synthetase inhibitor OKY-046 (Kaminogo, M., et al., *Neurol. Med. Chir. (Tokyo)*, 38(11):704-8; discussion 708-9 (1998)); The rat serine protease inhibitor 2.1 gene (LeCam, A., et al., *Biochem. Biophys. Res. Commun.*, 253(2):311-4 (1998)); A new intracellular serine protease inhibitor expressed in the rat pituitary gland complexes with granzyme B (Hill, R. M., et al., *FEBS Lett.*, 440(3):361-4 (1998)); 3,4-Dichloroisocoumarin (Hammed, A., et al., *Proc. Soc. Exp. Biol. Med.*, 219(2): 132-7 (1998)); LEX032 (Bains, A. S., et al., *Eur. J. Pharmacol.*, 356(1):67-72 (1998)); N-tosyl-L-phenylalanine chloromethyl ketone (Dryjanski, M., et al., *Biochemistry*, 37(40):14151-6 (1998)); Mouse gene for the serine protease inhibitor neuroserpin (P112) (Berger, P., et al., *Gene*, 214 (1-2):25-33 (1998)); Rat serine protease inhibitor 2.3 gene (Paul, C., et al., *Eur. J. Biochem.*, 254(3):538-46 (1998)); Ecotin (Yang, S. Q., et al., *J. Mol. Biol.*, 279(4):945-57 (1998)); A 14 kDa plant-related serine protease inhibitor (Roch, P., et al., *Dev. Comp. Immunol.*, 22(1):1-12 (1998)); Matrix-associated serine protease inhibitor TFPI-2/33 kDa MSPI (Rao, C. N., et al., *Int. J. Cancer*, 76(5):749-56 (1998)); ONO-3403 (Hiwasa, T., et al., *Cancer Lett.*, 126 (2):221-5 (1998)); Bdellastasin (Moser, M., et al., *Eur. J. Biochem.*, 253(1):212-20 (1998)); Bikunin (Xu, Y., et al., *J. Mol. Biol.*, 276(5):955-66 (1998)); Nafamostat mesilate (Mellgren, K., et al., *Thromb. Haemost.*, 79(2):342-7 (1998)); The growth hormone dependent serine protease inhibitor, Spi 2.1 (Maake, C., et al., *Endocrinology*, 138(12): 5630-6 (1997)); Growth factor activator inhibitor type 2, a Kunitz-type serine protease inhibitor (Kawaguchi, T., et al., *J. Biol. Chem.*, 272(44):27558-64 (1997)); Heat-stable serine protease inhibitor protein from ovaries of the desert locust, *Schistocerga gregaria* (Hamdaoui, A., et al., *Biochem. Biophys. Res. Commun.*, 238(2):357-60 (1997)); Bikunin, (Delaria, K. A., et al., *J. Biol. Chem.*, 272(18): 12209-14 (1997)); Human placental bikunin (Marlor, C. W., et al., *J. Biol. Chem.*, 272(10):12202-8 (1997)); Hepatocyte growth factor activator inhibitor, a novel Kunitz-type serine protease inhibitor (Shimomura, T., et al., *J. Biol. Chem.*, 272(10):6370-6 (1997)); FUT-187, oral serine protease inhibitor, (Shiozaki, H., et al., *Gan To Kaguku Ryoho*, 23(14): 1971-9 (1996)); Extracellular matrix-associated serine protease inhibitors (Mr 33,000, 31,000, and 27,000 (Rao, C. N., et al., *Arch. Biochem. Biophys.*, 335(1):82-92 (1996)); An irreversible isocoumarin serine protease inhibitor (Palencia, D. D., et al., *Biol. Reprod.*, 55(3):536-42 (1996)); 4-(2-aminoethyl)-benzenesulfonyl fluoride (AEBSF) (Nakabo, Y., et al., *J. Leukoc. Biol.*, 60(3):328-36 (1996)); Neuroserpin (Osterwalder, T., et al., *EMBO J.*, 15(12):2944-53 (1996)); Human serine protease inhibitor alpha-1-antitrypsin (Forney, J. R., et al., *J. Parasitol.* 82(3): 496-502 (1996)); Rat serine protease inhibitor 2.3 (Simar-Blanchet, A. E., et al., *Eur. J. Biochem.*, 236(2):638-48 (1996)); Gebaxate mesilate (parodi, F., et al., *J. Cardiothorac. Vasc. Anesth.*, 10(2):235-7 (1996)); Recombinant serine protease inhibitor, CPTI II (Stankiewicz, M., et al., (*Acta Biochim. Pol.*, 43(3):525-9 (1996)); A cysteine-rich serine protease inhibitor (Guamerin II) (Kim, D. R., et al., *J. Enzym. Inhib.*, 10(2):81-91 (1996)); Diisopropylfluorophosphate (Lundqvist, H., et al., *Inflamm. Res.*, 44(12):510-7 (1995)); Nexin 1 (Yu, D. W., et al., *J. Cell Sci.*, 108(Pt 12):3867-74 (1995)); LEX032 (Scalia, R., et al., *Shock*, 4(4):251-6 (1995)); Protease nexin I (Houenou, L. J., et al., *Proc. Natl. Acad. Sci. U.S.A.*, 92(3):895-9 (1995)); Chymase-directed serine protease inhibitor (Woodard S. L., et al., *J. Immunol.*, 153(11):5016-25 (1994)); N-alpha-tosyl-L-lysyl-chloromethyl ketone (TLCK) (Bourinbaiar, A. S., et al., *Cell Immunol.*, 155(1):230-6 (1994)); Smpi56 (Ghendler, Y., et al., *Exp. Parasitol.*, 78(2):121-31 (1994)); *Schistosoma haematobium* serine protease (Blanton, R. E., et al., *Mol. Biochem. Parasitol.*, 63(1):1-11 (1994)); Spi-1 (Warren, W. C., et al., *Mol. Cell. Endocrinol.*, 98(1):27-32 (1993)); TAME (Jessop, J. J., et al., *Inflammation*, 17(5): 613-31 (1993)); Antithrombin III (Kalaria, R. N., et al., *Am. J. Pathol.*, 143(3):886-93 (1993)); FOY-305 (Ohkoshi, M., et al., *Anticancer Res.*, 13(4):963-6 (1993)); Camostat mesilate (Senda, S., et al., *Intern. Med.*, 32(4):350-4 (1993)); Pigment epithelium-derived factor (Steele, F. R., et al., *Proc. Natl. Acad. Sci. U.S.A.*, 90(4):1526-30 (1993)); Antistasin (Holstein, T. W., et al., *FEBS Lett.*, 309(3):288-92 (1992)); The vaccinia virus K2L gene encodes a serine protease inhibitor (Zhou, J., et al., *Virology*, 189(2):678-86 (1992)); Bowman-Birk serine-protease inhibitor (Werner, M. H., et al., *J. Mol. Biol.*, 225(3):873-89 (1992); FUT-175 (Yanamoto, H., et al., *Neurosurgery*, 30(3):358-63 (1992)); FUT-175; (Yanamoto, H., et al., *Neurosurgery*, 30(3):351-6, discussion 356-7 (1992)); PAI-I (Yreadwell, B. V., et al., *J. Orthop. Res.*, 9(3):309-16 (1991)); 3,4-Dichloroisocoumarin (Rusbridge, N. M., et al., *FEBS Lett.*, 268(1):133-6 (1990)); Alpha 1-antichymotrypsin (Lindmark, B. E., et al., *Am. Rev. Respir. Des.*, 141(4 Pt 1):884-8 (1990)); P-toluenesulfonyl-L-arginine methyl ester (TAME) (Scuderi, P., *J. Immunol.*, 143(1):168-73 (1989)); Aprotinin (Seto, S., et al., *Adv. Exp. Med. Biol.*, 247B:49-54 (1989)); Alpha 1-antichymotrypsin (Abraham, C. R., et al., *Cell*, 52(4):487-501 (1988)); Contrapsin (Modha, J., et al., *Parasitology*, 96 (Pt 1):99-109 (1988)); (FOY-305) (Yamauchi, Y., et al., *Hiroshima J. Med. Sci.*, 36(1):81-7 No abstract available (1987)); Alpha 2-antiplasmin (Holmes, W. E., et al., *J. Biol. Chem.*, 262(4):1659-64 (1987)); 3,4-dichloroisocoumarin (Harper, J. W., et al., *Biochemistry*, 24(8):1831-41 (1985)); Diisopropylfluorophosphate (Tsutsui, K., et al., *Biochem. Biophys. Res. Commun.*, 123(1):271-7 (1984)); Gabexate mesilate (Hesse, B., et al., *Pharmacol. Res. Commun.*, 16(7):637-45 (1984)); Phenyl methyl sulfonyl fluoride (Dufer, J., et al., *Scand. J. Haematol.*, 32(1):25-32 (1984)); Aprotinin (Seto, S., et al., *Hypertension*, 5(6):893-9 (1983)); Protease inhibitor CI-2 (McPhalen, C. A., et al., *J. Mol. Biol.*, 168(2):445-7 (1983)); Phenylmethylsulfonyl fluoride (Sekar V., et al., *Biochem. Biophys. Res. Commun.*, 89(2): 474-8 (1979)); PGE1 (Feinstein, M. D., et al., *Prostaglandine*, 14(6):1075-93 (1977).

c. Combinatorial Libraries and Other Libraries

The source of compounds for the screening assays, can be libraries, including, but are not limited to, combinatorial libraries. Methods for synthesizing combinatorial libraries and characteristics of such combinatorial libraries are known in the art (See generally, *Combinatorial Libraries: Synthesis, Screening and Application Potential* (Cortese Ed.) Walter de Gruyter, Inc., 1995; Tietze and Lieb, *Curr. Opin. Chem. Biol.*, 2(3):363-71 (1998); Lam, *Anticancer Drug Des.*, 12(3):145-67 (1997); Blaney and Martin, *Curr. Opin.*

Chem. Biol., 1(1):54-9 (1997); and Schultz and Schultz, Biotechnol. Prog., 12(6):729-43 (1996)).

Methods and strategies for generating diverse libraries, primarily peptide- and nucleotide-based oligomer libraries, have been developed using molecular biology methods and/or simultaneous chemical synthesis methodologies (see, e.g., Dower et al., *Annu. Rep. Med. Chem.*, 26:271-280 (1991); Fodor et al., *Science*, 251:767-773 (1991); Jung et al., *Angew. Chem. Ind. Ed. Engl.*, 31:367-383 (1992); Zuckerman et al., *Proc. Natl. Acad. Sci. USA*, 89:4505-4509 (1992); Scott et al., *Science*, 249:386-390 (1990); Devlin et al., *Science*, 249:404-406 (1990); Cwirla et al., *Proc. Natl. Acad. Sci. USA*, 87:6378-6382 (1990); and Gallop et al., *J. Medicinal Chemistry*, 37:1233-1251 (1994)). The resulting combinatorial libraries potentially contain millions of compounds and that can be screened to identify compounds that exhibit a selected activity.

The libraries fall into roughly three categories: fusion-protein-displayed peptide libraries in which random peptides or proteins are presented on the surface of phage particles or proteins expressed from plasmids; support-bound synthetic chemical libraries in which individual compounds or mixtures of compounds are presented on insoluble matrices, such as resin beads (see, e.g., Lam et al., *Nature*, 354:82-84 (1991)) and cotton supports (see, e.g., Eichler et al., *Biochemistry* 32:11035-11041 (1993)); and methods in which the compounds are used in solution (see, e.g., Houghten et al., *Nature*, 354:84-86 (1991); Houghten et al., *BioTechniques*, 313:412-421 (1992); and Scott et al., *Curr. Opin. Biotechnol*, 5:40-48 (1994)). There are numerous examples of synthetic peptide and oligonucleotide combinatorial libraries and there are many methods for producing libraries that contain non-peptidic small organic molecules. Such libraries can be based on basis set of monomers that are combined to form mixtures of diverse organic molecules or that can be combined to form a library based upon a selected pharmacophore monomer.

Either a random or a deterministic combinatorial library can be screened by the presently disclosed and/or claimed screening methods. In either of these two libraries, each unit of the library is isolated and/or immobilized on a solid support. In the deterministic library, one knows a priori a particular unit's location on each solid support. In a random library, the location of a particular unit is not known a priori although each site still contains a single unique unit. Many methods for preparing libraries are known to those of skill in this art (see, e.g., Geysen et al., *Proc. Natl. Acad. Sci. USA*, 81:3998-4002 (1984), Houghten et al., *Proc. Natl. Acad. Sci. USA*, 81:5131-5135 (1985)). Combinatorial library generated by the any techniques known to those of skill in the art are contemplated (see, e.g., Table 1 of Schultz and Schultz, Biotechnol. Prog., 12(6):729-43 (1996)) for screening; Bartel et al., *Science*, 261:1411-1418 (1993); Baumbach et al. *BioPharm*, (May):24-35 (1992); Bock et al. *Nature*, 355:564-566 (1992); Borman, S., Combinatorial chemists focus on small molecules, molecular recognition, and automation, *Chem. Eng. News*, 74:29 (1996); Boublik, et al., Eukaryotic Virus Display: Engineering the Major Surface Glycoproteins of the Autographa California Nuclear Polyhedrosis Virus (ACNPV) for the Presentation of Foreign Proteins on the Virus Surface, *Bio/Technology*, 13:1079-1084 (1995); Brenner, et al., Encoded Combinatorial Chemistry, *Proc. Natl. Acad. Sci. U.S.A.*, 89:5381-5383 (1992); Caflisch, et al., Computational Combinatorial Chemistry for De Novo Ligand Design: Review and Assessment, *Perspect. Drug Discovery Des.*, 3:51-84 (1995); Cheng, et al., Sequence-Selective Peptide Binding with a Peptido-A,B-trans-steroidal Receptor Selected from an Encoded Combinatorial Library, *J. Am. Chem. Soc.*, 118: 1813-1814 (1996); Chu, et al., Affinity Capillary Electrophoresis to Identify the Peptide in A Peptide Library that Binds Most Tightly to Vancomycin, *J. Org. Chem.*, 58:648-652 (1993); Clackson, et al., Making Antibody Fragments Using Phage Display Libraries, *Nature*, 352:624-628 (1991); Combs, et al., Protein Structure-Based Combinatorial Chemistry: Discovery of Non-Peptide Binding Elements to Src SH3 Domain, *J. Am. Chem. Soc.*, 118:287-288 (1996); Cwirla, et al., Peptides On Phage: A Vast Library of Peptides for Identifying Ligands, *Proc. Natl. Acad. Sci. U.S.A.*, 87:6378-6382 (1990); Ecker, et al., Combinatorial Drug Discovery: Which Method will Produce the Greatest Value?, *Bio/Technology*, 13:351-360 (1995); Ellington, et al., In Vitro Selection of RNA Molecules That Bind Specific Ligands, *Nature*, 346:818-822 (1990); Ellman, J. A., Variants of Benzodiazephines, *J. Am. Chem. Soc.*, 114:10997 (1992); Erickson, et al., *The Proteins*; Neurath, H., Hill, R. L., Eds.: Academic: New York, 1976; pp. 255-257; Felici, et al., *J. Mol. Biol.*, 222:301-310 (1991); Fodor, et al., Light-Directed, Spatially Addressable Parallel Chemical Synthesis, *Science*, 251:767-773 (1991); Francisco, et al., Transport and Anchoring of Beta-Lactamase to the External Surface of E. Coli., *Proc. Natl. Acad. Sci. U.S.A.*, 89:2713-2717 (1992); Georgiou, et al., Practical Applications of Engineering Gram-Negative Bacterial Cell Surfaces, *TIBTECH*, 11:6-10 (1993); Geysen, et al., Use of peptide synthesis to probe viral antigens for epitopes to a resolution of a single amino acid, *Proc. Natl. Acad. Sci. U.S.A.*, 81:3998-4002 (1984); Glaser, et al., Antibody Engineering by Condon-Based Mutagenesis in a Filamentous Phage Vector System, *J. Immunol.*, 149:3903-3913 (1992); Gram, et al., In vitro selection and affinity maturation of antibodies from a naive combinatorial immunoglobulin library, *Proc. Natl. Acad. Sci.*, 89:3576-3580 (1992); Han, et al., Liquid-Phase Combinatorial Synthesis, *Proc. Natl. Acad. Sci. U.S.A.*, 92:6419-6423 (1995); Hoogenboom, et al., Multi-Subunit Proteins on the Surface of Filamentous Phage: Methodologies for Displaying Antibody (Fab) Heavy and Light Chains, *Nucleic Acids Res.*, 19:4133-4137 (1991); Houghten, et al., General Method for the Rapid Solid-Phase Synthesis of Large Numbers of Peptides: Specificity of Antigen-Antibody Interaction at the Level of Individual Amino Acids, *Proc. Natl. Acad. Sci. U.S.A.*, 82:5131-5135 (1985); Houghten, et al., The Use of Synthetic Peptide Combinatorial Libraries for the Determination of Peptide Ligands in Radio-Receptor Assays-Opiod-Peptides, *Bioorg. Med. Chem. Lett*, 3:405-412 (1993); Houghten, et al., Generation and Use of Synthetic Peptide Combinatorial Libraries for Basic Research and Drug Discovery, *Nature*, 354:84-86 (1991); Huang, et al., Discovery of New Ligand Binding Pathways in Myoglobin by Random Mutagenesis, *Nature Struct. Biol.*, 1:226-229 (1994); Huse, et al., Generation of a Large Combinatorial Library of the Immunoglobulin Repertoire In Phage Lambda, *Science*, 246:1275-1281 (1989); Janda, K. D., New Strategies for the Design of Catalytic Antibodies, *Biotechnol. Prog.*, 6:178-181 (1990); Jung, et al., Multiple Peptide Synthesis Methods and Their Applications, *Angew. Chem. Int. Ed. Engl.*, 31:367-486 (1992); Kang, et al., Linkage of Recognition and Replication Functions By Assembling Combinatorial Antibody Fab Libraries Along Phage Surfaces, *Proc. Natl. Acad. Sci. U.S.A.*, 88:4363-4366 (1991a); Kang, et al., Antibody Redesign by Chain Shuffling from Random Combinatorial Immunoglobulin Libraries, *Proc. Natl. Acad. Sci. U.S.A.*, 88:11120-11123 (1991b); Kay, et al., An M13 Phage Library Displaying Random 38-Amino- Acid-Peptides as a Source of Novel Sequences with Affinity to Selected Targets Genes, *Gene,* 128:59-65 (1993); Lam, et al., A new type of synthetic peptide library for identifying ligand-binding activity, *Nature,* 354:82-84 (1991) (published errata appear in *Nature,* 358:434 (1992) and *Nature,* 360:768 (1992); Lebl, et al., One Bead One Structure Combinatorial Libraries, *Biopolymers (Pept. Sci.),* 37:177-198 (1995); Lerner, et al., Antibodies without Immunization, *Science,* 258:1313-1314 (1992); Li, et al., Minimization of a Polypeptide Hormone, *Science,* 270:1657-1660 (1995); Light, et al., Display of Dimeric Bacterial Alkaline Phosphatase on the Major Coat Protein of Filamentous Bacteriophage, *Bioorg. Med. Chem. Lett.,* 3:1073-1079 (1992); Little, et al., Bacterial Surface Presentation of Proteins and Peptides: An Alternative to Phage Technology?, *Trends Biotechnol.,* 11:3-5 (1993); Marks, et al., By-Passing Immunization. Human Antibodies from V-Gene Libraries Displayed on Phage, *J. Mol. Biol.,* 222:581-597 (1991); Matthews, et al., Substrate Phage: Selection of Protease Substrates by Monovalent Phage Display, *Science,* 260: 1113-1117 (1993); McCafferty, et al., Phage Enzymes: Expression and Affinity Chromatography of Functional Alkaline Phosphatase on the Surface of Bacteriophage, *Protein Eng.,* 4:955-961 (1991); Menger, et al., Phosphatase Catalysis Developed Via Combinatorial Organic Chemistry, *J. Org. Chem.,* 60:6666-6667 (1995); Nicolaou, et al., *Angew. Chem. Int. Ed. Engl.,* 34:2289-2291 (1995); Oldenburg, et al., Peptide Ligands for A Sugar-Binding Protein Isolated from a Random Peptide Library, *Proc. Natl. Acad. Sci. U.S.A.,* 89:5393-5397 (1992); Parmley, et al., Antibody-Selectable Filamentous fd Phage Vectors: Affinity Purification of Target Genes, *Genes,* 73:305-318 (1988); Pinilla, et al., Synthetic Peptide Combinatorial Libraries (SPCLS)—Identification of the Antigenic Determinant of Beta-Endorphin Recognized by Monoclonal Antibody-3E7, *Gene,* 128: 71-76 (1993); Pinilla, et al., Review of the Utility of Soluble Combinatorial Libraries, *Biopolymers,* 37:221-240 (1995); Pistor, et al., Expression of Viral Hemagglutinin On the Surface of *E. Coli., Klin. Wochenschr.,* 66:110-116 (1989); Pollack, et al., Selective Chemical Catalysis by an Antibody, *Science,* 234:1570-1572 (1986); Rigler, et al., Fluorescence Correlations, Single Molecule Detection and Large Number Screening: Applications in Biotechnology, *J. Biotechnol.,* 41:177-186 (1995); Sarvetnick, et al., Increasing the Chemical Potential of the Germ-Line Antibody Repertoire, *Proc. Natl. Acad. Sci. U.S.A.,* 90:4008-4011 (1993); Sastry, et al., Cloning of the Immunological Repertoire in *Escherichia Coli* for Generation of Monoclonal Catalytic Antibodies: Construction of a Heavy Chain Variable Region-Specific cDNA Library, *Proc. Natl. Acad. Sci. U.S.A.,* 86:5728-5732 (1989); Scott, et al., Searching for Peptide Ligands with an Epitope Library, *Science,* 249:386-390 (1990); Sears, et al., Engineering Enzymes for Bioorganic Synthesis: Peptide Bond Formation, *Biotechnol. Prog.,* 12:423-433 (1996); Simon, et. al., Peptides: A Modular Approach to Drug Discovery, *Proc. Natl. Acad. Sci. U.S.A.,* 89:9367-9371 (1992); Still, et al., Discovery of Sequence-Selective Peptide Binding by Synthetic Receptors Using Encoded Combinatorial Libraries, *Acc. Chem. Res.,* 29:155-163 (1996); Thompson, et al., Synthesis and Applications of Small Molecule Libraries, *Chem. Rev.,* 96:555-600 (1996); Tramontano, et al., Catalytic Antibodies, *Science,* 234:1566-1570 (1986); Wrighton, et al., Small Peptides as Potent Mimetics of the Protein Hormone Erythropoietin, *Science,* 273:458-464 (1996); York, et al., Combinatorial mutagenesis of the reactive site region in plasminogen activator inhibitor I, *J. Biol. Chem.,* 266:8595-8600 (1991); Zebedee, et al., Human Combinatorial Antibody Libraries to Hepatitis B Surface Antigen, *Proc. Natl. Acad. Sci. U.S.A.,* 89:3175-3179 (1992); Zuckermann, et al., Identification of Highest-Affinity Ligands by Affinity Selection from Equimolar Peptide Mixtures Generated by Robotic Synthesis, *Proc. Natl. Acad. Sci. U.S.A.,* 89:4505-4509 (1992).

For example, peptides that bind to an endotheliase or a protease domain of an endotheliase can be identified using phage display libraries. In an exemplary embodiment, this method can include a) contacting phage from a phage library with the endotheliase protein or a protease domain thereof; (b) isolating phage that bind to the protein; and (c) determining the identity of at least one peptide coded by the isolated phage to identify a peptide that binds to an endotheliase.

E. Modulators of the Activity of Endotheliases

Provided herein are compounds, identified by screening or produced using the endotheliases or protease domain in other screening methods, that modulate the activity of an endotheliase. These compounds act by directly interacting with the endotheliase or by altering transcription or translation thereof. Such molecules include, but are not limited to, antibodies that specifically react with an endotheliase, particularly with the protease domain thereof, antisense nucleic acids that alter expression of the endotheliase, antibodies, peptide mimetics and other such compounds.

1. Antibodies

Provided herein are antibodies that specifically bind to an endotheliase, preferably to the protease domain of the endotheliase protein. Preferably, the antibody is a monoclonal antibody, and preferably, the antibody immuno-specifically binds to the protease domain of the endotheliase protein. In particular embodiments, antibodies to the protease domain of endotheliase 1 are provided. Also provided are to endotheliase 2 and to the protease domain thereof are also provided.

The endotheliase protein and domains, fragments, homologs and derivatives thereof may be used as immunogens to generate antibodies that specifically bind such immunogens. Such antibodies include but are not limited to polyclonal, monoclonal, chimeric, single chain, Fab fragments, and an Fab expression library. In a specific embodiment, antibodies to human endotheliase are produced. In another embodiment, complexes formed from fragments of endotheliase, which fragments contain the serine protease domain, are used as immunogens for antibody production.

Various procedures known in the art may be used for the production of polyclonal antibodies to endotheliase protein, its domains, derivatives, fragments or analogs. For production of the antibody, various host animals can be immunized by injection with the native endotheliase protein or a synthetic version, or a derivative of the foregoing, such as a cross-linked endotheliase. Such host animals include but are not limited to rabbits, mice, rats, etc. Various adjuvants can be used to increase the immunological response, depending on the host species, and include but are not limited to Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and *corynebacterium parvum*.

For preparation of monoclonal antibodies directed towards an endotheliase or domains, derivatives, fragments or analogs thereof, any technique that provides for the production of antibody molecules by continuous cell lines in culture may be used. Such techniques include but are not restricted to the hybridoma technique originally developed by Kohler and Milstein (*Nature* 256:495-497 (1975)), the trioma technique, the human B-cell hybridoma technique (Kozbor et al., *Immunology Today* 4:72 (1983)), and the EBV hybridoma technique to produce human monoclonal antibodies (Cole et al., in *Monoclonal Antibodies and Cancer Therapy*, Alan R. Liss, Inc., pp. 77-96 (1985)). In an additional embodiment, monoclonal antibodies can be produced in germ-free animals utilizing recent technology (PCT/US90/02545). Human antibodies may be used and can be obtained by using human hybridomas (Cote et al., *Proc. Natl. Acad. Sci. USA* 80:2026-2030 (1983)). Or by transforming human B cells with EBV virus in vitro (Cole et al., in *Monoclonal Antibodies and Cancer Therapy*, Alan R. Liss, Inc., pp. 77-96 (1985)). Techniques developed for the production of "chimeric antibodies" (Morrison et al., *Proc. Natl. Acad. Sci. USA* 81:6851-6855 (1984); Neuberger et al., *Nature* 312:604-608 (1984); Takeda et al., *Nature* 314:452-454 (1985)) by splicing the genes from a mouse antibody molecule specific for the endotheliase protein together with genes from a human antibody molecule of appropriate biological activity can be used.

Techniques described for the production of single chain antibodies (U.S. Pat. No. 4,946,778) can be adapted to produce endotheliase-specific single chain antibodies. An additional embodiment uses the techniques described for the construction of Fab expression libraries (Huse et al., *Science* 246:1275-1281 (1989)) to allow rapid and easy identification of monoclonal Fab fragments with the desired specificity for endotheliase or endotheliase domains, derivatives, or analogs thereof. Non-human antibodies can be "humanized" by known methods (see, e.g., U.S. Pat. No. 5,225,539).

Antibody fragments that contain the idiotypes of endotheliase can be generated by techniques known in the art. For example, such fragments include but are not limited to: the F(ab')2 fragment which can be produced by pepsin digestion of the antibody molecule; the Fab' fragments that can be generated by reducing the disulfide bridges of the F(ab')2 fragment, the Fab fragments that can be generated by treating the antibody molecule with papain and a reducing agent, and Fv fragments.

In the production of antibodies, screening for the desired antibody can be accomplished by techniques known in the art, e.g., ELISA (enzyme-linked immunosorbent assay). To select antibodies specific to a particular domain of the endotheliase one may assay generated hybridomas for a product that binds to the fragment of the endotheliase that contains such a domain.

The foregoing antibodies can be used in methods known in the art relating to the localization and/or quantitation of endotheliase proteins, e.g., for imaging these proteins, measuring levels thereof in appropriate physiological samples, in diagnostic methods, etc.

In another embodiment, (see infra), anti-endotheliase antibodies, or fragments thereof, containing the binding domain are used as therapeutic agents.

2. Peptides and Peptide Mimetics

Provided herein are methods for identifying molecules that bind to and modulate the activity of endotheliases. Included among molecules that bind to endotheliases are peptides and peptide mimetics. Peptide mimetics are molecules or compounds that mimic the necessary molecular conformation of a ligand or polypeptide for specific binding to a target molecule such as, e.g., an endotheliase. In an exemplary embodiment, the peptides or peptide mimetics bind to the protease domain of the endotheliase. Such peptides and peptide mimetics include those of antibodies that specifically bind an endotheliase and, preferably, bind to the protease domain of an endotheliase. The peptides and peptide mimetics identified by methods provided herein can be agonists or antagonists of endotheliases.

Such peptides and peptide mimetics are useful for diagnosing, treating, preventing, and screening for a disease or disorder associated with endotheliase activity in a mammal. In addition, the peptides and peptide mimetics are useful for identifying, isolating, and purifying molecules or compounds that modulate the activity of an endotheliase, or specifically bind to an endotheliase, preferably, the protease domain of an endotheliase. Low molecular weight peptides and peptide mimetics can have strong binding properties to a target molecule, e.g., an endotheliase or, preferably, to the protease domain of an endotheliase.

Peptides and peptide mimetics that bind to endotheliases as described herein can be administered to mammals, including humans, to modulate endotheliase activity. Thus, methods for therapeutic treatment and prevention of diseases or disorders associated with angiogenesis that comprise administering a peptide or peptide mimetic compound in an amount sufficient to modulate such activity are provided. Thus, also provided herein are methods for treating a subject having such a disease or disorder in which a peptide or peptide mimetic compound is administered to the subject in a therapeutically effective dose or amount.

Compositions containing the peptides or peptide mimetics can be administered for prophylactic and/or therapeutic treatments. In therapeutic applications, compositions can be administered to a patient already suffering from a disease, as described above, in an amount sufficient to cure or at least partially arrest the symptoms of the disease and its complications. Amounts effective for this use will depend on the severity of the disease and the weight and general state of the patient.

In prophylactic applications, compositions containing the peptides and peptide mimetics are administered to a patient susceptible to or otherwise at risk of a particular disease. Such an amount is defined to be a "prophylactically effective dose". In this use, the precise amounts again depend on the patient's state of health and weight.

Accordingly, the peptides and peptide mimetics that bind to an endotheliase can be used generating pharmaceutical compositions containing, as an active ingredient, at least one of the peptides or peptide mimetics in association with a pharmaceutical carrier or diluent. The compounds can be administered, for example, by oral, pulmonary, parental (intramuscular, intraperitoneal, intravenous (IV) or subcutaneous injection), inhalation (via a fine powder formulation), transdermal, nasal, vaginal, rectal, or sublingual routes of administration and can be formulated in dosage forms appropriate for each route of administration (see, e.g., International PCT application Nos. WO 93/25221 and WO 94/17784; and European Patent Application 613,683).

Peptides and peptide mimetics that bind to endotheliases are useful in vitro as unique tools for understanding the biological role of endotheliases, including the evaluation of the many factors thought to influence, and be influenced by, the production of endotheliase. Such peptides and peptide mimetics are also useful in the development of other compounds that bind to and modulate the activity of an endotheliase, because such compounds provide important information on the relationship between structure and activity that should facilitate such development.

The peptides and peptide mimetics are also useful as competitive binders in assays to screen for new endotheliases or endotheliase agonists. In such assay embodiments, the compounds can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^{125}$I enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups. The compounds may also include spacers or linkers in cases where the compounds are to be attached to a solid support.

Moreover, based on their ability to bind to an endotheliase, the peptides and peptide mimetics can be used as reagents for detecting endotheliases in living cells, fixed cells, in biological fluids, in tissue homogenates, in purified, natural biological materials, etc. For example, by labelling such peptides and peptide mimetics, one can identify cells having endotheliases. In addition, based on their ability to bind an endotheliase, the peptides and peptide mimetics can be used in situ staining, FACS (fluorescence-activated cell sorting), Western blotting, ELISA, etc. In addition, based on their ability to bind to an endotheliase, the peptides and peptide mimetics can be used in purification of endotheliase polypeptides or in purifying cells expressing the endotheliase polypeptides, e.g., a polypeptide encoding the protease domain of an endotheliase.

The peptides and peptide mimetics can also be utilized as commercial reagents for various medical research and diagnostic uses. The activity of the peptides and peptide mimetics can be evaluated either in vitro or in vivo in one of the numerous models described in McDonald (1992) *Am. J. of Pediatric Hematology/Oncology*, 14:8-21, which is incorporated herein by reference.

Peptide and Peptide Mimetic Therapy

Peptides and peptide mimetics that can bind to endotheliases or the protease domain of endotheliases and modulate the activity thereof, or have endotheliase activity, can be used for treatment of diseases and disorders associated with angiogenesis. The peptides and peptide mimetics may be delivered, in vivo or ex vivo, to the cells of a subject in need of treatment. Further, peptides which have endotheliase activity can be delivered, in vivo or ex vivo, to cells which carry mutant or missing alleles encoding the endotheliase gene. Any of the techniques described herein or known to the skilled artisan can be used for preparation and in vivo or ex vivo delivery of such peptides and peptide mimetics that are substantially free of other human proteins. For example, the peptides can be readily prepared by expression in a microorganism or synthesis in vitro.

The peptides or peptide mimetics can be introduced into cells, in vivo or ex vivo, by microinjection or by use of liposomes, for example. Alternatively, the peptides or peptide mimetics may be taken up by cells, in vivo or ex vivo, actively or by diffusion. In addition, extracellular application of the peptide or peptide mimetic may be sufficient to effect treatment of a disease or disorder associated with angiogenesis. Other molecules, such as drugs or organic compounds, that: 1) bind to an endotheliase or protease domain thereof; or 2) have a similar function or activity to an endotheliase or protease domain thereof, may be used in methods for treatment.

Rational Drug Design

The goal of rational drug design is to produce structural analogs of biologically active polypeptides or peptides of interest or of small molecules or peptide mimetics with which they interact (e.g., agonists, antagonists, inhibitors) in order to fashion drugs which are, e.g., more active or stable forms thereof; or which, e.g., enhance or interfere with the function of a polypeptide in vivo (e.g., an endotheliase). In one approach, one first determines the three-dimensional structure of a protein of interest (e.g., an endotheliase or polypeptide having a protease domain) or, for example, of a endotheliase-ligand complex, by X-ray crystallography, by computer modeling or most typically, by a combination of approaches (see, e.g., Erickson et al. 1990). Also, useful information regarding the structure of a polypeptide may be gained by modeling based on the structure of homologous proteins. In addition, peptides can be analyzed by an alanine scan. In this technique, an amino acid residue is replaced by Ala, and its effect on the peptide's activity is determined. Each of the amino acid residues of the peptide is analyzed in this manner to determine the important regions of the peptide.

Also, a polypeptide or peptide that binds to an endotheliase or, preferably, the protease domain of an endotheliase, can be selected by a functional assay, and then the crystal structure of this polypeptide or peptide can be determined. The polypeptide can be, for example, an antibody specific for an endotheliase or the protein domain of an endotheliase. This approach can yield a pharmacore upon which subsequent drug design can be based. Further, it is possible to bypass the crystallography altogether by generating anti-idiotypic polypeptides or peptides, (anti-ids) to a functional, pharmacologically active polypeptide or peptide that binds to an endotheliase or protease domain of an endotheliase. As a mirror image of a mirror image, the binding site of the anti-ids is expected to be an analog of the original target molecule, e.g., an endotheliase or polypeptide having an endotheliase. The anti-id could then be used to identify and isolate peptides from banks of chemically or biologically produced banks of peptides. Selected peptides would then act as the pharmacore.

Thus, one may design drugs which have, e.g., improved activity or stability or which act as modulators (e.g., inhibitors, agonists, antagonists, etc.) of endotheliase activity, and are useful in the methods, particularly the methods for diagnosis, treatment, prevention, and screening of a disease or disorder associated with angiogenesis. By virtue of the availability of cloned endotheliase sequences, sufficient amounts of the endotheliase polypeptide may be made available to perform such analytical studies as X-ray crystallography. In addition, the knowledge of the amino acid sequence of an endotheliase or the protease domain thereof, e.g., the protease domain encoded by the amino acid sequence of SEQ ID NO: 2, can provide guidance on computer modeling techniques in place of, or in addition to, X-ray crystallography.

Methods of Identifying Peptides and Peptide Mimetics that Bind to Endotheliases

Peptides having a binding affinity to the endotheliase polypeptides provided herein (e.g., an endotheliase or a polypeptide having a protease domain of an endotheliase) can be readily identified, for example, by random peptide diversity generating systems coupled with an affinity enrichment process. Specifically, random peptide diversity generating systems include the "peptides on plasmids" system (see, e.g., U.S. Pat. Nos. 5,270,170 and 5,338,665); the "peptides on phage" system (see, e.g., U.S. Pat. No. 6,121, 238 and Cwirla, et al. (1990) *Proc. Natl. Acad. Sci. U.S.A.* 87:6378-6382); the "polysome system;" the "encoded synthetic library (ESL)" system; and the "very large scale immobilized polymer synthesis" system (see, e.g., U.S. Pat. No. 6,121,238; and Dower et al. (1991) *Ann. Rep. Med. Chem.* 26:271-280).

For example, using the procedures described above, random peptides can generally be designed to have a defined number of amino acid residues in length (e.g., 12). To generate the collection of oligonucleotides encoding the random peptides, the codon motif (NNK)x, where N is nucleotide A, C, G, or T (equimolar; depending on the methodology employed, other nucleotides can be employed), K is G or T (equimolar), and x is an integer corresponding to the number of amino acids in the peptide (e.g., 12) can be used to specify any one of the 32 possible codons resulting from the NNK motif: 1 for each of 12 amino acids, 2 for each of 5 amino acids, 3 for each of 3 amino acids, and only one of the three stop codons. Thus, the NNK motif encodes all of the amino acids, encodes only one stop codon, and reduces codon bias.

The random peptides can be presented, for example, either on the surface of a phage particle, as part of a fusion protein containing either the pIII or the pVIII coat protein of a phage fd derivative (peptides on phage) or as a fusion protein with the LacI peptide fusion protein bound to a plasmid (peptides on plasmids). The phage or plasmids, including the DNA encoding the peptides, can be identified and isolated by an affinity enrichment process using immobilized endotheliase polypeptide having a protease domain. The affinity enrichment process, sometimes called "panning," typically involves multiple rounds of incubating the phage, plasmids, or polysomes with the immobilized endotheliase polypeptide, collecting the phage, plasmids, or polysomes that bind to the endotheliase polypeptide (along with the accompanying DNA or mRNA), and producing more of the phage or plasmids (along with the accompanying LacI-peptide fusion protein) collected.

Characteristics of Peptides and Peptide Mimetics

Typically, the molecular weight of preferred peptides or peptide mimetics is from about 250 to about 8,000 daltons. If the peptides are oligomerized, dimerized and/or derivatized with a hydrophilic polymer (e.g., to increase the affinity and/or activity of the compounds), the molecular weights of such peptides can be substantially greater and can range anywhere from about 500 to about 120,000 daltons, more preferably from about 8,000 to about 80,000 daltons. Such peptides can comprise 9 or more amino acids wherein the amino acids are naturally occurring or synthetic (non-naturally occurring) amino acids. One skilled in the art would know how to determine the affinity and molecular weight of the peptides and peptide mimetics suitable for therapeutic and/or diagnostic purposes (e.g., see Dower et al., U.S. Pat. No. 6,121,238).

The peptides may be covalently attached to one or more of a variety of hydrophilic polymers. Suitable hydrophilic polymers include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. When the peptide compounds are derivatized with such polymers, their solubility and circulation half-lives can be increased with little, if any, diminishment in their binding activity. The peptide compounds may be dimerized and each of the dimeric subunits can be covalently attached to a hydrophilic polymer. The peptide compounds can be PEGylated, i.e., covalently attached to polyethylene glycol (PEG).

Peptide analogs are commonly used in the pharmaceutical industry as non-peptide drugs with properties analogous to those of the template peptide. These types of non-peptide compounds are termed "peptide mimetics" or "peptidomimetics" (Luthman et al., *A Textbook of Drug Design and Development*, 14:386-406, 2nd Ed., Harwood Academic Publishers (1996); Joachim Grante (1994) *Angew. Chem. Int. Ed. Engl.*, 33:1699-1720; Fauchere (1986) *J. Adv. Drug Res.*, 15:29; Veber and Freidinger (1985) *TINS*, p. 392; and Evans et al. (1987) *J. Med. Chem.* 30:1229). Peptide mimetics that are structurally similar to therapeutically useful peptides may be used to produce an equivalent or enhanced therapeutic or prophylactic effect. Preparation of peptidomimetics and structures thereof are known to those of skill in this art.

Systematic substitution of one or more amino acids of a consensus sequence with a D-amino acid of the same type (e.g., D-lysine in place of L-lysine) may be used to generate more stable peptides. In addition, constrained peptides containing a consensus sequence or a substantially identical consensus sequence variation may be generated by methods known in the art (Rizo et al. (1992) *Ann. Rev. Biochem.*, 61:387, incorporated herein by reference); for example, by adding internal cysteine residues capable of forming intramolecular disulfide bridges which cyclize the peptide.

Those skilled in the art would appreciate that modifications may be made to the peptides and mimetics without deleteriously effecting the biological or functional activity of the peptide. Further, the skilled artisan would know how to design non-peptide structures in three dimensional terms, that mimic the peptides that bind to a target molecule, e.g., an endotheliase or, preferably, the protease domain of endotheliases (see, e.g., Eck and Sprang (1989) *J. Biol. Chem.* 26: 17605-18795).

When used for diagnostic purposes, the peptides and peptide mimetics may be labeled with a detectable label and, accordingly, the peptides and peptide mimetics without such a label can serve as intermediates in the preparation of labeled peptides and peptide mimetics. Detectable labels can be molecules or compounds, which when covalently attached to the peptides and peptide mimetics, permit detection of the peptide and peptide mimetics in vivo, for example, in a patient to whom the peptide or peptide mimetic has been administered, or in vitro, e.g., in a sample or cells. Suitable detectable labels are well known in the art and include, by way of example, radioisotopes, fluorescent labels (e.g., fluorescein), and the like. The particular detectable label employed is not critical and is selected relative to the amount of label to be employed as well as the toxicity of the label at the amount of label employed. Selection of the label relative to such factors is well within the skill of the art.

Covalent attachment of a detectable label to the peptide or peptide mimetic is accomplished by conventional methods well known in the art. For example, when the $^{125}$I radioisotope is employed as the detectable label, covalent attachment of $^{125}$I to the peptide or the peptide mimetic can be achieved by incorporating the amino acid tyrosine into the peptide or peptide mimetic and then iodinating the peptide (see, e.g., Weaner et al. (1994) *Synthesis and Applications of Isotopically Labelled Compounds*, pp. 137-140). If tyrosine is not present in the peptide or peptide mimetic, incorporation of tyrosine to the N or C terminus of the peptide or peptide mimetic can be achieved by well known chemistry. Likewise, $^{32}$P can be incorporated onto the peptide or peptide mimetic as a phosphate moiety through, for example, a hydroxyl group on the peptide or peptide mimetic using conventional chemistry.

Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivatization (e.g., labeling) of peptidomimetics should not substantially interfere with the desired biological or pharmacological activity of the peptidomimetic.

Methods of Preparing Peptides and Peptide Mimetics

Peptides that bind to endotheliases can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology (see, e.g., Merrifield (1963) *J. Am. Chem. Soc.*, 85:2149, incorporated herein by reference.)

Using the "encoded synthetic library" or "very large scale immobilized polymer synthesis" systems (see, e.g., U.S. Pat. Nos. 5,925,525, and 5,902,723); one can not only determine the minimum size of a peptide with the activity of interest, one can also make all of the peptides that form the group of peptides that differ from the preferred motif (or the minimum size of that motif) in one, two, or more residues. This collection of peptides can then be screened for ability to bind to the target molecule, e.g., and endotheliase or, preferably, the protease domain of an endotheliase. This immobilized polymer synthesis system or other peptide synthesis methods can also be used to synthesize truncation analogs and deletion analogs and combinations of truncation and deletion analogs of the peptide compounds.

These procedures can also be used to synthesize peptides in which amino acids other than the 20 naturally occurring, genetically encoded amino acids are substituted at one, two, or more positions of the peptide. For instance, naphthylalanine can be substituted for tryptophan, facilitating synthesis. Other synthetic amino acids that can be substituted into the peptides include L-hydroxypropyl, L-3, 4-dihydroxy-phenylalanyl, d amino acids such as L-d-hydroxylysyl and D-d-methylalanyl, L-α-methylalanyl, βamino acids, and isoquinolyl. D amino acids and non-naturally occurring synthetic amino acids can also be incorporated into the peptides (see, e.g., Roberts et al. (1983) *Unusual Amino/Acids in Peptide Synthesis;* 5(6):341-449).

The peptides may also be modified by phosphorylation (see, e.g., W. Bannwarth et al. (1996) *Bioorganic and Medicinal Chemistry Letters,* 6(17):2141-2146), and other methods for making peptide derivatives (see, e.g., Hruby et al. (1990) *Biochem. J.,* 268(2):249-262). Thus, peptide compounds also serve as a basis to prepare peptide mimetics with similar biological activity.

Those of skill in the art recognize that a variety of techniques are available for constructing peptide mimetics with the same or similar desired biological activity as the corresponding peptide compound but with more favorable activity than the peptide with respect to solubility, stability, and susceptibility to hydrolysis and proteolysis (see, e.g., Morgan et al. (1989) *Ann. Rep. Med. Chem.,* 24:243-252). Methods for preparing peptide mimetics modified at the N-terminal amino group, the C-terminal carboxyl group, and/or changing one or more of the amido linkages in the peptide to a non-amido linkage are known to those of skill in the art.

Amino terminus modifications include alkylating, acetylating, adding a carbobenzoyl group, forming a succinimide group, etc. (see, e.g., Murray et al. (1995) *Burger's Medicinal Chemistry and Drug Discovery, 5th ed.,* Vol. 1, Manfred E. Wolf, ed., John Wiley and Sons, Inc.). C-terminal modifications include mimetics wherein the C-terminal carboxyl group is replaced by an ester, an amide or modifications to form a cyclic peptide.

In addition to N-terminal and C-terminal modifications, the peptide compounds, including peptide mimetics, can advantageously be modified with or covalently coupled to one or more of a variety of hydrophilic polymers. It has been found that when peptide compounds are derivatized with a hydrophilic polymer, their solubility and circulation half-lives may be increased and their immunogenicity is masked, with little, if any, diminishment in their binding activity. Suitable nonproteinaceous polymers include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. The hydrophilic polymers also can have an average molecular weights of about 5,000 daltons, 10,000 daltons and 20,000 daltons.

Methods for derivatizing peptide compounds or for coupling peptides to such polymers have been described (see, e.g., Zallipsky (1995) *Bioconjugate Chem.,* 6:150-165; Monfardini et al. (1995) *Bioconjugate Chem.,* 6:62-69; U.S. Pat. No. 4,640,835; U.S. Pat. No. 4,496,689; U.S. Pat. No. 4,301,144; U.S. Pat. No. 4,670,417; U.S. Pat. No. 4,791,192; U.S. Pat. No. 4,179,337 and WO 95/34326, all of which are incorporated by reference in their entirety herein).

Other methods for making peptide derivatives are described, for example, in Hruby et al. (1990), *Biochem J.,* 268(2):249-262, which is incorporated herein by reference. Thus, the peptide compounds also serve as structural models for non-peptidic compounds with similar biological activity. Those of skill in the art recognize that a variety of techniques are available for constructing compounds with the same or similar desired biological activity as a particular peptide compound but with more favorable activity with respect to solubility, stability, and susceptibility to hydrolysis and proteolysis (see, e.g., Morgan et al. (1989) *Ann. Rep. Med. Chem.,* 24:243-252, incorporated herein by reference). These techniques include replacing the peptide backbone with a backbone composed of phosphonates, amidates, carbamates, sulfonamides, secondary amines, and N-methylamino acids.

Peptide compounds may exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues may also be substituted with a homocysteine.

F. Conjugates

A conjugate, containing: a) a protease domain of an endotheliase protein encoded by a nucleic acid hybridizes to a nucleic acid having the nucleotide sequence set forth in the SEQ. ID NO:1; and b) a targeting agent linked to the endotheliase directly or via a linker, wherein the agent facilitates: i) affinity isolation or purification of the conjugate; ii) attachment of the conjugate to a surface; iii) detection of the conjugate; or iv) targeted delivery to a selected tissue or cell, is provided herein. The conjugate can be a chemical conjugate or a fusion protein mixture thereof.

The targeting agent is preferably a protein or peptide fragment, such as a tissue specific or tumor specific monoclonal antibody or growth factor or fragment thereof linked either directly or via a linker to an endotheliase or a protease domain thereof. The targeting agent may also be a protein or peptide fragment that contains a protein binding sequence, a nucleic acid binding sequence, a lipid binding sequence, a polysaccharide binding sequence, or a metal binding sequence, or a linker for attachment to a solid support.

In a particular embodiment, the conjugate contains a) an endotheliase or protease domain of an endotheliase protein encoded by a nucleic acid hybridizes to a nucleic acid molecule having the nucleotide sequence set forth in the SEQ. ID NO:1, 3, 5 or 22; and b) a targeting agent linked to the endotheliase directly or via a linker.

Conjugates, such as fusion proteins and chemical conjugates, of the endotheliase with a protein or peptide fragment (or plurality thereof) that functions, for example, to facilitate affinity isolation or purification of the endotheliase domain, attachment of the endotheliase domain to a surface, or detection of the endotheliase domain are provided. The conjugates can be produced by chemical conjugation, such as via thiol linkages, but are preferably produced by recombinant means as fusion proteins. In the fusion protein, the peptide or fragment thereof is linked to either the N-terminus or C-terminus of the endotheliase domain. In chemical conjugates the peptide or fragment thereof may be linked anywhere that conjugation can be effected, and there may be a plurality of such peptides or fragments linked to a single endotheliase domain or to a plurality thereof.

The targeting agent is preferably for in vitro delivery to a cell or tissue, and includes agents such as cell or tissue-specific antibodies, growth factors and other factors expressed on specific cells; and other cell or tissue specific agents the promote directed delivery of a linked protein.

Most preferably the targeting agent specifically delivers the endotheliase to selected cells by interaction with a cell surface protein and internalization of conjugate or endotheliase portion thereof. These conjugate are used in a variety of methods and are particularly suited for use in methods of activation of prodrugs, such as prodrugs that upon cleavage by the particular endotheliase are cytotoxic. The prodrugs are administered prior to simultaneously with or subsequently to the conjugate. Upon delivery to the targeted cells, the protease activates the prodrug, which then exhibits is therapeutic effect, such as a cytotoxic effect.

1. Conjugation

Conjugates with linked endotheliase domains can be prepared either by chemical conjugation, recombinant DNA technology, or combinations of recombinant expression and chemical conjugation. The endotheliase domains and the targeting agent may be linked in any orientation and more than one targeting agents and/or endotheliase domains may be present in a conjugate.

a. Fusion Proteins

Fusion proteins are proved herein. A fusion protein contains: a) one or a plurality of domains of an endotheliases and b) a targeting agent. The fusion proteins are preferably produced by recombinant expression of nucleic acids that encode the fusion protein.

b. Chemical Conjugation

To effect chemical conjugation herein, the endotheliase domain is linked via one or more selected linkers or directly to the targeting agent. Chemical conjugation must be used if the targeted agent is other than a peptide or protein, such a nucleic acid or a non-peptide drug. Any means known to those of skill in the art for chemically conjugating selected moieties may be used.

2. Linkers

Linkers for two purposes are contemplated herein. The conjugates may include one or more linkers between the endotheliase portion and the targeting agent. Additionally, linkers are used for facilitating or enhancing immobilization of an endotheliase or portion thereof on a solid support, such as a microtiter plate, silicon or silicon-coated chip, glass or plastic support, such as for high throughput solid phase screening protocols.

a. Exemplary Linkers

Any linker known to those of skill in the art for preparation of conjugates may be used herein. These linkers are typically used in the preparation of chemical conjugates; peptide linkers may be incorporated into fusion proteins.

Linkers can be any moiety suitable to associate a domain of endotheliase and a targeting agent. Such linkers and linkages include, but are not limited to, peptidic linkages, amino acid and peptide linkages, typically containing between one and about 60 amino acids, more generally between about 10 and 30 amino acids, chemical linkers, such as heterobifunctional cleavable cross-linkers, including but are not limited to, N-succinimidyl (4-iodoacetyl)-aminobenzoate, sulfosuccinimydil (4-iodoacetyl)-aminobenzoate, 4-succinimidyl-oxycarbonyl-a-(2-pyridyidithio)toluene, sulfosuccinimidyl-6-[a-methyl-a-(pyridyldithiol)-toluamido]hexanoate, N-succinimidyl-3-(-2-pyridyldithio)-proprionate, succinimidyl 6[3(-(-2-pyridyidithio)-proprionamido]hexanoate, sulfosuccinimidyl 6[3(-(-2-pyridyldithio)-propionamido]hexanoate, 3-(2-pyridyldithio)-propionyl hydrazide, Ellman's reagent, dichlorotriazinic acid, and S-(2-thiopyridyl)-L-cysteine. Other linkers include, but are not limited to peptides and other moieties that reduce stearic hindrance between the domain of endotheliase and the targeting agent, intracellular enzyme substrates, linkers that increase the flexibility of the conjugate, linkers that increase the solubility of the conjugate, linkers that increase the serum stability of the conjugate, photocleavable linkers and acid cleavable linkers.

Other exemplary linkers and linkages that are suitable for chemically linked conjugates include, but are not limited to, disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Other linkers include, acid cleavable linkers, such as bismaleimideothoxy propane, acid labile-transferrin conjugates and adipic acid dihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (see, Batra et al. *Molecular Immunol.*, 30:379-386 (1993)). In some embodiments, several linkers may be included in order to take advantage of desired properties of each linker.

Chemical linkers and peptide linkers may be inserted by covalently coupling the linker to the domain of endotheliase and the targeting agent. The heterobifunctional agents, described below, may be used to effect such covalent coupling. Peptide linkers may also be linked by expressing DNA encoding the linker and TA, linker and targeted agent, or linker, targeted agent and TA as a fusion protein. Flexible linkers and linkers that increase solubility of the conjugates are contemplated for use, either alone or with other linkers are also contemplated herein.

1) Acid Cleavable, Photocleavable and Heat Sensitive Linkers

Acid cleavable linkers, photocleavable and heat sensitive linkers may also be used, particularly where it may be necessary to cleave the domain of endotheliase to permit it to be more readily accessible to reaction. Acid cleavable linkers include, but are not limited to, bismaleimideothoxy propane; and adipic acid dihydrazide linkers (see, e.g., Fattom et al. (1992) *Infection & Immun.* 60:584-589) and acid labile transferrin conjugates that contain a sufficient portion of transferrin to permit entry into the intracellular transferrin cycling pathway (see, e.g., Welhöner et al. (1991) *J. Biol. Chem.* 266:4309-4314).

Photocleavable linkers are linkers that are cleaved upon exposure to light (see, e.g., Goldmacher et al. (1992) *Bioconj. Chem.* 3:104-107, which linkers are herein incorporated by reference), thereby releasing the targeted agent upon exposure to light. Photocleavable linkers that are cleaved upon exposure to light are known (see, e.g., Hazum et al. (1981) in *Pept., Proc. Eur. Pept. Symp.,* 16th, Brunfeldt, K (Ed), pp. 105-110, which describes the use of a nitrobenzyl group as a photocleavable protective group for cysteine; Yen et al. (1989) *Makromol. Chem* 190:69-82, which describes watersoluble photocleavable copolymers, including hydroxypropylmethacrylamide copolymer, glycine copolymer, fluorescein copolymer and methylrhodamine copolymer; Goldmacher et al. (1992) *Bioconj. Chem.* 3:104-107, which describes a cross-linker and reagent that undergoes photolytic degradation upon exposure to near UV light (350 nm); and Senter et al. (1985) *Photochem. Photobiol* 42:231-237, which describes nitrobenzyloxycarbonyl chloride cross linking reagents that produce photocleavable linkages), thereby releasing the targeted agent upon exposure to light. Such linkers would have particular use in treating dermatological or ophthalmic conditions that can be exposed to light using fiber optics. After administration of the conjugate, the eye or skin or other body part can be exposed to light, resulting in release of the targeted moiety from the conjugate. Such photocleavable linkers are useful in connection with diagnostic protocols in which it is desirable to remove the targeting agent to permit rapid clearance from the body of the animal.

2) Other Linkers for Chemical Conjugation

Other linkers, include trityl linkers, particularly, derivatized trityl groups to generate a genus of conjugates that provide for release of therapeutic agents at various degrees of acidity or alkalinity. The flexibility thus afforded by the ability to preselect the pH range at which the therapeutic agent will be released allows selection of a linker based on the known physiological differences between tissues in need of delivery of a therapeutic agent (see, e.g., U.S. Pat. No. 5,612,474). For example, the acidity of tumor tissues appears to be lower than that of normal tissues.

3) Peptide Linkers

The linker moieties can be peptides. Peptide linkers can be employed in fusion proteins and also in chemically linked conjugates. The peptide typically has from about 2 to about 60 amino acid residues, for example from about 5 to about 40, or from about 10 to about 30 amino acid residues. The length selected will depend upon factors, such as the use for which the linker is included.

Peptide linkers are advantageous when the targeting agent is proteinaceous. For example, the linker moiety can be a flexible spacer amino acid sequence, such as those known in single-chain antibody research. Examples of such known linker moieties include, but are not limited to, peptides, such as $(Gly_mSer)_n$ and $(Ser_mGly)_n$, in which n is 1 to 6, preferably 1 to 4, more preferably 2 to 4, and m is 1 to 6, preferably 1 to 4, more preferably 2 to 4, enzyme cleavable linkers and others.

Additional linking moieties are described, for example, in Huston et al., *Proc. Natl. Acad. Sci. U.S.A.* 85:5879-5883, 1988; Whitlow, M., et al., *Protein Engineering* 6:989-995, 1993; Newton et al., *Biochemistry* 35:545-553, 1996; A. J. Cumber et al., *Bioconj. Chem.* 3:397-401, 1992; Ladurner et al., *J. Mol. Biol.* 273:330-337, 1997; and U.S. Pat. No. 4,894,443. In some embodiments, several linkers may be included in order to take advantage of desired properties of each linker.

3. Targeting Agents

Any agent that facilitates detection, immobilization, or purification of the conjugate is contemplated for use herein. For chemical conjugates any moiety that has such properties is contemplated; for fusion proteins, the targeting agent is a protein, peptide or fragment thereof that sufficient is to effect the targeting activity. Preferred targeting agents are those that deliver the endotheliase or portion thereof to selected cells and tissues. Such agents include tumor specific monoclonal antibodies and portions thereof, growth factors, such as FGF, EGF, PDGF, VEGF, cytokines, including chemokines, and other such agents.

4. Nucleic Acids, Plasmids and Cells

Isolated nucleic acid fragments encoding fusion proteins are provided. The nucleic acid fragment that encodes the fusion protein includes: a) nucleic acid encoding a protease domain of an endotheliase protein encoded by a nucleic acid that hybridizes to a nucleic acid having the nucleotide sequence set forth in the SEQ. ID NO:1; and b) nucleic acid encoding a protein, peptide or effective fragment thereof that facilitates: i) affinity isolation or purification of the fusion protein; ii) attachment of the fusion protein to a surface; or iii) detection of the fusion protein. Preferably, the nucleic acid is DNA.

Plasmids for replication and vectors for expression that contain the above nucleic acid fragments are also provided. Cells containing the plasmids and vectors are also provided. The cells can be any suitable host including, but are not limited to, bacterial cells, yeast cells, fungal cells, plant cells, insect cell and animal cells. The nucleic acids, plasmids, and cells containing the plasmids can be prepared according to methods known in the art including any described herein.

Also provided are methods for producing the above fusion proteins. An exemplary method includes the steps of growing, i.e. culturing the cells so that they proliferate, cells containing a plasmid encoding the fusion protein under conditions whereby the fusion protein is expressed by the cell, and recovering the expressed fusion protein. Methods for expressing and recovering recombinant proteins are well known in the art (See generally, *Current Protocols in Molecular Biology* (1998) § 16, John Wiley & Sons, Inc.) and such methods can be used for expressing and recovering the expressed fusion proteins. Preferably, the recombinant expression and recovery methods disclosed in Section B can be used.

The recovered fusion proteins can be isolated or purified by methods known in the art such as centrifugation, filtration, chromatograph, electrophoresis, immunoprecipitation, etc., or by a combination thereof (See generally, *Current Protocols in Molecular Biology* (1998) § 10, John Wiley & Sons, Inc.). Preferably, the recovered fusion protein is isolated or purified through affinity binding between the protein or peptide fragment of the fusion protein and an affinity binding moiety. As discussed in the above sections regarding the construction of the fusion proteins, any affinity binding pairs can be constructed and used in the isolation or purification of the fusion proteins. For example, the affinity binding pairs can be protein binding sequences/protein, DNA binding sequences/DNA sequences, RNA binding sequences/RNA sequences, lipid binding sequences/lipid, polysaccharide binding sequences/polysaccharide, or metal binding sequences/metal.

6. Immobilization and Supports or Substrates Therefor

In certain embodiments, where the targeting agents are designed for linkage to surfaces, the endotheliase can be attached by linkage such as ionic or covalent, non-covalent or other chemical interaction, to a surface of a support or matrix material. Immobilization may be effected directly or via a linker. The endotheliase may be immobilized on any suitable support, including, but are not limited to, silicon chips, and other supports described herein and known to those of skill in the art. A plurality of endotheliase or protease domains thereof may be attached to a support, such as an array (i.e., a pattern of two or more) of conjugates on the surface of a silicon chip or other chip for use in high throughput protocols and formats.

It is also noted that the domains of the endotheliase can be linked directly to the surface or via a linker without a targeting agent linked thereto. Hence chips containing arrays of the domains of the endotheliase.

The matrix material or solid supports contemplated herein are generally any of the insoluble materials known to those of skill in the art to immobilize ligands and other molecules, and are those that used in many chemical syntheses and separations. Such supports are used, for example, in affinity chromatography, in the immobilization of biologically active materials, and during chemical syntheses of biomolecules, including proteins, amino acids and other organic molecules and polymers. The preparation of and use of supports is well known to those of skill in this art; there are many such materials and preparations thereof known. For example, naturally-occurring support materials, such as agarose and cellulose, may be isolated from their respective sources, and processed according to known protocols, and synthetic materials may be prepared in accord with known protocols.

The supports are typically insoluble materials that are solid, porous, deformable, or hard, and have any required structure and geometry, including, but not limited to: beads, pellets, disks, capillaries, hollow fibers, needles, solid fibers, random shapes, thin films and membranes. Thus, the item may be fabricated from the matrix material or combined with it, such as by coating all or part of the surface or impregnating particles.

Typically, when the matrix is particulate, the particles are at least about 10-2000 μM, but may be smaller or larger, depending upon the selected application. Selection of the matrices will be governed, at least in part, by their physical and chemical properties, such as solubility, functional groups, mechanical stability, surface area swelling propensity, hydrophobic or hydrophilic properties and intended use.

If necessary, the support matrix material can be treated to contain an appropriate reactive moiety. In some cases, the support matrix material already containing the reactive moiety may be obtained commercially. The support matrix material containing the reactive moiety may thereby serve as the matrix support upon which molecules are linked. Materials containing reactive surface moieties such as amino silane linkages, hydroxyl linkages or carboxysilane linkages may be produced by well established surface chemistry techniques involving silanization reactions, or the like. Examples of these materials are those having surface silicon oxide moieties, covalently linked to gamma-aminopropyl-silane, and other organic moieties; N-[3-(triethyoxysilyl)propyl]phthelamic acid; and bis-(2-hydroxyethyl)aminopropyltriethoxysilane. Exemplary of readily available materials containing amino group reactive functionalities, include, but are not limited to, para-aminophenyltriethyoxysilane. Also derivatized polystyrenes and other such polymers are well known and readily available to those of skill in this art (e.g., the Tentagel® Resins are available with a multitude of functional groups, and are sold by Rapp Polymere, Tubingen, Germany; see, U.S. Pat. No. 4,908,405 and U.S. Pat. No. 5,292,814; see, also Butz et al., *Peptide Res.*, 7:20-23 (1994); and Kleine et al., *Immunobiol.*, 190:53-66 (1994)).

These matrix materials include any material that can act as a support matrix for attachment of the molecules of interest. Such materials are known to those of skill in this art, and include those that are used as a support matrix. These materials include, but are not limited to, inorganics, natural polymers, and synthetic polymers, including, but are not limited to: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene and others (see, Merrifield, *Biochemistry*, 3:1385-1390 (1964)), polyacrylamides, latex gels, polystyrene, dextran, polyacrylamides, rubber, silicon, plastics, nitrocellulose, celluloses, natural sponges. Of particular interest herein, are highly porous glasses (see, e.g., U.S. Pat. No. 4,244,721) and others prepared by mixing a borosilicate, alcohol and water.

Synthetic supports include, but are not limited to: acrylamides, dextran-derivatives and dextran co-polymers, agarose-polyacrylamide blends, other polymers and co-polymers with various functional groups, methacrylate derivatives and co-polymers, polystyrene and polystyrene copolymers (see, e.g., Merrifield, *Biochemistry*, 3:1385-1390 (1964); Berg et al., in *Innovation Perspect. Solid Phase Synth. Collect. Pap.*, Int. Symp., 1st, Epton, Roger (Ed), pp. 453-459 (1990); Berg et al., *Pept., Proc. Eur. Pept. Symp.*, 20th, Jung, G. et al. (Eds), pp. 196-198 (1989); Berg et al., *J. Am. Chem. Soc.*, 111:8024-8026 (1989); Kent et al., *Isr. J. Chem.*, 17:243-247 (1979); Kent et al., *J. Org. Chem.*, 43:2845-2852 (1978); Mitchell et al., *Tetrahedron Lett.*, 42:3795-3798 (1976); U.S. Pat. No. 4,507,230; U.S. Pat. No. 4,006,117; and U.S. Pat. No. 5,389,449). Such materials include those made from polymers and co-polymers such as polyvinylalcohols, acrylates and acrylic acids such as polyethylene-co-acrylic acid, polyethylene-co-methacrylic acid, polyethylene-co-ethylacrylate, polyethylene-co-methyl acrylate, polypropylene-co-acrylic acid, polypropylene-co-methyl-acrylic acid, polypropylene-co-ethylacrylate, polypropylene-co-methyl acrylate, polyethylene-co-vinyl acetate, polypropylene-co-vinyl acetate, and those containing acid anhydride groups such as polyethylene-co-maleic anhydride and polypropylene-co-maleic anhydride. Liposomes have also been used as solid supports for affinity purifications (Powell et al. *Biotechnol. Bioeng.*, 33:173 (1989)).

Numerous methods have been developed for the immobilization of proteins and other biomolecules onto solid or liquid supports (see, e.g., Mosbach, *Methods in Enzymology*, 44 (1976); Weetall, *Immobilized Enzymes, Antigens, Antibodies, and Peptides*, (1975); Kennedy et al., *Solid Phase Biochemistry, Analytical and Synthetic Aspects*, Scouten, ed., pp. 253-391 (1983); see, generally, Affinity Techniques. Enzyme Purification: *Part B. Methods in Enzymology*, Vol. 34, ed. W. B. Jakoby, M. Wilchek, Acad. Press, N.Y. (1974); and Immobilized Biochemicals and Affinity Chromatography, *Advances in Experimental Medicine and Biology*, vol. 42, ed. R. Dunlap, Plenum Press, N.Y. (1974)).

Among the most commonly used methods are absorption and adsorption or covalent binding to the support, either directly or via a linker, such as the numerous disulfide linkages, thioether bonds, hindered disulfide bonds, and covalent bonds between free reactive groups, such as amine and thiol groups, known to those of skill in art (see, e.g., the PIERCE CATALOG, ImmunoTechnology Catalog & Handbook, 1992-1993, which describes the preparation of and use of such reagents and provides a commercial source for such reagents; Wong, *Chemistry of Protein Conjugation and Cross Linking*, CRC Press (1993); see also DeWitt et al., *Proc. Natl. Acad. Sci. U.S.A.*, 90:6909 (1993); Zuckermann et al., *J. Am. Chem. Soc.*, 114:10646 (1992); Kurth et al., *J. Am. Chem. Soc.*, 116:2661 (1994); Ellman et al., *Proc. Natl. Acad. Sci. U.S.A.*, 91:4708 (1994); Sucholeiki, *Tetrahedron Lttrs.*, 35:7307 (1994); Su-Sun Wang, *J. Org. Chem.*, 41:3258 (1976); Padwa et al., *J. Org. Chem.*, 41:3550 (1971); and Vedejs et al., *J. Org. Chem.*, 49:575 (1984), which describe photosensitive linkers).

To effect immobilization, a composition containing the protein or other biomolecule is contacted with a support material such as alumina, carbon, an ion-exchange resin, cellulose, glass or a ceramic. Fluorocarbon polymers have been used as supports to which biomolecules have been attached by adsorption (see, U.S. Pat. No. 3,843,443; Published International PCT Application WO/86 03840).

G. Prognosis and Diagnosis

Endotheliase proteins, domains, analogs, and derivatives thereof, endotheliase nucleic acids (and sequences complementary thereto), and anti-endotheliase antibodies, have uses in diagnostics. Such molecules can be used in assays, such as immunoassays, to detect, prognose, diagnose, or monitor various conditions, diseases, and disorders affecting endotheliase expression, or monitor the treatment thereof. In particular, such an immunoassay is carried out by a method including contacting a sample derived from a patient with an anti-endotheliase antibody under conditions such that immunospecific binding can occur, and detecting or measuring the amount of any immunospecific binding by the antibody. In a specific aspect, such binding of antibody, in tissue sections, can be used to detect aberrant endotheliase localization or aberrant (e.g., low or absent) levels of endotheliase protein. In a specific embodiment, antibody to endotheliase protein can be used to assay in a patient tissue or serum sample for the presence of endotheliase protein where an aberrant level of endotheliase protein is an indication of a diseased condition.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

Endotheliase genes and related nucleic acid sequences and subsequences, including complementary sequences, can also be used in hybridization assays. Endotheliase nucleic acid sequences, or subsequences thereof containing about at least 8 nucleotides, preferably 14 or 16 or more continuous nucleotides, can be used as hybridization probes. Hybridization assays can be used to detect, prognose, diagnose, or monitor conditions, disorders, or disease states associated with aberrant changes in endotheliase expression and/or activity as described supra. In particular, such a hybridization assay is carried out by a method by contacting a sample containing nucleic acid with a nucleic acid probe capable of hybridizing to endotheliase DNA or RNA, under conditions such that hybridization can occur, and detecting or measuring any resulting hybridization.

In a specific embodiment, a method of diagnosing a disease or disorder characterized by detecting an aberrant level of an endotheliase in a subject is provided herein by measuring the level of the DNA, RNA, protein or functional activity of the epithelial endotheliase at least partially encoded by a nucleic acid that hybridizes to a nucleic acid having the nucleotide sequence set forth in the SEQ. ID NO:1 in a sample derived from the subject, wherein an increase or decrease in the level of the DNA, RNA, protein or functional activity of the endotheliase, relative to the level of the DNA, RNA, protein or functional activity found in an analogous sample not having the disease or disorder indicates the presence of the disease or disorder in the subject.

In another specific embodiment, a method of diagnosing or screening for the presence of or a predisposition for developing a disease or disorder associated with undesired and/or uncontrolled angiogenesis in a subject is provided by measuring the level of DNA, RNA, protein, or functional activity of an endotheliase at least partially encoded by a nucleic acid that hybridizes to a nucleic acid having the nucleotide sequence set forth in the SEQ. ID NO:1 in a sample derived from the subject, wherein an increase in the level of the DNA, RNA, protein, or functional activity in the sample, relative to the level of the DNA, RNA, protein, or functional activity found in an analogous sample not having the undesired and/or uncontrolled angiogenesis, indicates the presence of the undesired and/or uncontrolled angiogenesis.

In still another specific embodiment, a method of diagnosing or screening for the presence of or a predisposition for developing a disease or disorder associated with deficient angiogenesis in a subject is provided herein, which method by measuring the level of DNA, RNA, protein, or functional activity of an endotheliase at least partially encoded by a nucleic acid that hybridizes to a nucleic acid having the nucleotide sequence set forth in the SEQ. ID NO:1 in a sample derived from the subject, wherein a decrease in the level of the DNA, RNA, protein, or functional activity in the sample, relative to the level of the DNA, RNA, protein, or functional activity found in an analogous sample not having the deficient angiogenesis, indicates the presence of the deficient angiogenesis.

Kits for diagnostic use are also provided, that comprise in one or more containers an anti-endotheliase antibody, and, optionally, a labeled binding partner to the antibody. Alternatively, the anti-endotheliase antibody can be labeled (with a detectable marker, e.g., a chemiluminescent, enzymatic, fluorescent, or radioactive moiety). A kit is also provided that includes in one or more containers a nucleic acid probe capable of hybridizing to endotheliase-encoding RNA. In a specific embodiment, a kit can comprise in one or more containers a pair of primers (e.g., each in the size range of 6-30 nucleotides) that are capable of priming amplification, e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art under appropriate reaction conditions of at least a portion of an endotheliase-encoding nucleic acid. A kit can optionally further comprise in a container a predetermined amount of a purified endotheliase protein or nucleic acid, e.g., for use as a standard or control.

H. Pharmaceutical Compositions and Modes of Administration

1. Components of the Compositions

Pharmaceutical compositions containing the identified compounds that modulate the activity of an endotheliase are provided herein. Also provided are combinations of a compound that modulates the activity of an endotheliase and another treatment or compound for treatment of a disorder involving aberrant angiogenesis, such as a pro-angiogenic treatment or agent, or an anti-angiogenic treatment or agent. In certain embodiments, the compounds that modulate the activity of an endotheliase inhibit its activity and other compound is an anti-angiogenic treatment or agent.

The endotheliase modulator and the anti-angiogenic or pro-angiogenic agent can be packaged as separate compositions for administration together or sequentially or intermittently. Alternatively, they can be contained in a single composition for administration as a single composition. The combinations can be packaged as kits.

a. Endotheliase Inhibitors

Any endotheliase inhibitors, including those described herein when used alone or in combination with other compounds, that can alleviate, reduce, ameliorate, prevent, or place or maintain in a state of remission of clinical symptoms or diagnostic markers associated with undesired and/or uncontrolled angiogenesis, particularly vascular malformations and cardiovascular disorders, chronic inflammatory diseases and aberrant wound repairs, circulatory disorders, crest syndromes, dermatological disorders, or ocular disorders, can be used in the present combinations.

In one embodiment, the endotheliase inhibitor is an antibody or fragment thereof that specifically reacts with an endotheliase or the protease domain thereof, an inhibitor of the endotheliase production, an inhibitor of the epithelial endotheliase membrane-localization, or any inhibitor of the expression of or activity of an endotheliase.

b. Anti-Angiogenic Agents and Anti-Tumor Agents

Any anti-angiogenic agents and anti-tumor agents, including those described herein, when used alone or in combination with other compounds, that can alleviate, reduce, ameliorate, prevent, or place or maintain in a state of remission of clinical symptoms or diagnostic markers associated with undesired and/or uncontrolled angiogenesis and/or tumor growth and metastatis, particularly solid neoplasms, vascular malformations and cardiovascular disorders, chronic inflammatory diseases and aberrant wound repairs, circulatory disorders, crest syndromes, dermatological disorders, or ocular disorders, can be used in the combinations. Also contemplated are anti-tumor agents for use in combination with an inhibitor of an endotheliase.

For example, an anti-angiogenic agent used in the combination is an inhibitor of basement membrane degradation, an inhibitor of cell migration, an inhibitor of endothelial cell proliferation, an inhibitor of three-dimensional organization and establishment of patency, or a physiological or physical anti-angiogenic treatment. Other examples of anti-angiogenic agents and anti-tumor agents, include, but are not limited to, protease inhibitors, endostatin, taxol, TGF-β, FGF inhibitors (see, Auerbach and Auerbach, *Pharmacol. Ther.*, 63(3):265-311 (1994) for a comprehensive listing of well known anti-angiogenic agents). Particular anti-angiogenic agents used in the combination include AGM-1470 (TNP-470), angiostatic steroids, angiostatin, antibodies against avβ3, antibodies against bFGF, antibodies against IL-1, antibodies against TNF-α, antibodies against VEGF, auranofin, azathioprine, BB-94, BB-2516, basic FGF-soluble receptor, carboxyamido-trizole (CAI), cartilage-derived inhibitor (CDI), chitin, chloroquine, cisplatin, CM 101, cortisone/heparin, cortisone/hyaluroflan, cortexolone/heparin, CT-2584, cyclophosphamide, cyclosporin A, dexamethasone, diclofenac/hyaluronan, eosinophilic major basic protein, fibronectin peptides, glioma-derived angiogenesis inhibitory factor (GD-AIF), GM 1474, gold chloride, gold thiomalate, heparinases, hyaluronan (high and low molecular-weight species), hydrocortisone/beta-cyclodextran, ibuprofen, indomethacin, interferon-alpha, interferon gamma-inducible protein 10, interferon-gamma, IL-1, IL-2, IL-4, IL-12, laminin, levamisole, linomide, LM609, marimastat (BB-2516), medroxyprogesterone, Metastat (Col-3), methotrexate, minocycline, nitric oxide, octreotide (somatostatin analogue), Paclitaxel, D-penicillamine, pentosan polysulfate, placental proliferin-related protein, placental Rnase inhibitor, plasminogen activator inhibitor (PAIs), platelet factor-4 (PF4), prednisolone, prolactin (16-Kda fragment), proliferin-related protein, prostaglandin synthase inhibitor, protamine, retinoids, Roquinimex (LS-2616. linomide), somatostatin, substance P, suramin, SU101, tecogalan sodium (DS-4152), tetrahydrocortisol-thrombospondins (TSPs), tissue inhibitor of metalloproteinases (TIMP 1, 2, 3), vascular endothelial growth factor inhibitors, vitamin A, Vitaxin, vitreous fluids, thalidomide, 3-aminothalidomide, 3-hydroxy-thalidomide and metabolites or hydrolysis products of thalidomide, 3-aminothalidomide, or 3-hydroxythalidomide ((O'Reilly, *Investigational New Drugs*, 15:5-13 (1997); *J. Nat'l Cancer Instit.*, 88:786-788 (1996); U.S. Pat. Nos. 5,593,990, 5,629,327 and 5,712,291).

c. Pro-Angiogenic Agent

Any pro-angiogenic agents, including those described herein, when used alone or in combination with other compounds, that can promote physiological angiogenesis, particularly angiogenesis involved in normal placental, embryonic, fetal and post-natal development and growth, physiologically cyclical development in the ovarian follicle, corpus luteum and post-menstrual endometrium or wound healing, can be used in the present combinations.

The pro-angiogenic agent used in the combination can be a pro-angiogenic cytokine (Desai and Libutti, *J. Immunother.*, 22(3):186-211 (1999)). More preferably, the pro-angiogenic cytokine used is a basic fibroblast growth factor such as bFGF and FGF-2, a vascular endothelial growth factor/vascular permeability factor such as VEGF/VPF and vasculotropin, a platelet-derived endothelial cell growth factor such as PD-EDGF and thymidine phosphorylase, a transforming growth factor-beta (TGF-β), or angiopoietin-1 (Ang-1).

2. Formulations and Route of Administration

The compounds herein and agents are preferably formulated as pharmaceutical compositions, preferably for single dosage administration. The concentrations of the compounds in the formulations are effective for delivery of an amount, upon administration, that is effective for the intended treatment. Typically, the compositions are formulated for single dosage administration. To formulate a composition, the weight fraction of a compound or mixture thereof is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems, such as the assays provided herein.

The concentration of active compound in the drug composition will depend on absorption, inactivation and excretion rates of the active compound, the physicochemical characteristics of the compound, the dosage schedule, and amount administered as well as other factors known to those of skill in the art.

Typically a therapeutically effective dosage is contemplated. The amounts administered may be on the order of 0.001 to 1 mg/ml, preferably about 0.005-0.05 mg/ml, more preferably about 0.01 mg/ml, of blood volume. Pharmaceutical dosage unit forms are prepared to provide from about 1 mg to about 1000 mg and preferably from about 10 to about 500 mg, more preferably about 25-75 mg of the essential active ingredient or a combination of essential ingredients per dosage unit form. The precise dosage can be empirically determined.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or use of the claimed compositions and combinations containing them.

Preferred pharmaceutically acceptable derivatives include acids, salts, esters, hydrates, solvates and prodrug forms. The derivative is typically selected such that its pharmacokinetic properties are superior to the corresponding neutral compound.

Thus, effective concentrations or amounts of one or more of the compounds provided herein or pharmaceutically acceptable derivatives thereof are mixed with a suitable pharmaceutical carrier or vehicle for systemic, topical or local administration to form pharmaceutical compositions. Compounds are included in an amount effective for ameliorating or treating the disorder for which treatment is contemplated. The concentration of active compound in the composition will depend on absorption, inactivation, excretion rates of the active compound, the dosage schedule, amount administered, particular formulation as well as other factors known to those of skill in the art.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as Tween®, or dissolution in aqueous sodium bicarbonate. Derivatives of the compounds, such as prodrugs of the compounds may also be used in formulating effective pharmaceutical compositions. For ophthalmic indications, the compositions are formulated in an opthalmically acceptable carrier. For the ophthalmic uses herein, local administration, either by topical administration or by injection is preferred. Time release formulations are also desirable. Typically, the compositions are formulated for single dosage administration, so that a single dose administers an effective amount.

Upon mixing or addition of the compound with the vehicle, the resulting mixture may be a solution, suspension, emulsion or other composition. The form of the resulting mixture depends upon a number of factors, including the intended mode of administration and the solubility of the compound in the selected carrier or vehicle. If necessary, pharmaceutically acceptable salts or other derivatives of the compounds are prepared.

The compound is included in the pharmaceutically acceptable carrier in an amount sufficient to exert a therapeutically useful effect in the absence of undesirable side effects on the patient treated. It is understood that number and degree of side effects depends upon the condition for which the compounds are administered. For example, certain toxic and undesirable side effects are tolerated when treating life-threatening illnesses that would not be tolerated when treating disorders of lesser consequence.

The compounds can also be mixed with other active materials, that do not impair the desired action, or with materials that supplement the desired action known to those of skill in the art for treating diseases or disorders associated with aberrant angiogenesis and other disorders for which the treatments provided herein are contemplated.

The formulations of the compounds and agents for use herein include those suitable for oral, rectal, topical, inhalational, buccal (e.g., sublingual), parenteral (e.g., subcutaneous, intramuscular, intradermal, or intravenous), transdermal administration or any route. The most suitable route in any given case will depend on the nature and severity of the condition being treated and on the nature of the particular active compound which is being used. The formulations are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art (see, e.g., Remington's Pharmaceutical Sciences, Mack Publishing Company, Easton, Pa., 15th Edition, 1975). The composition or formulation to be administered will contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, the pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well-known in the art.

The pharmaceutical preparation may also be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid).

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin or to the eye preferably take the form of an ointment, cream, lotion, paste, gel, spray, aerosol and oil. Carriers which may be used include vaseline, lanoline, polyethylene glycols, alcohols, and combinations of two or more thereof. The topical formulations may further advantageously contain 0.05 to 15 percent by weight of thickeners selected from among hydroxypropyl methyl cellulose, methyl cellulose, polyvinylpyrrolidone, polyvinyl alcohol, poly (alkylene glycols), poly/hydroxyalkyl, (meth)acrylates or poly(meth)acrylamides. A topical formulation is often applied by instillation or as an ointment into the conjunctival sac. It can also be used for irrigation or lubrication of the eye, facial sinuses, and external auditory meatus. It may also be injected into the anterior eye chamber and other places. The topical formulations in the liquid state may be also present in a hydrophilic three-dimensional polymer matrix in the form of a strip, contact lens, and the like from which the active components are released.

For administration by inhalation, the compounds for use herein can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

Formulations suitable for buccal (sublingual) administration include, for example, lozenges containing the active compound in a flavored base, usually sucrose and acacia or tragacanth; and pastilles containing the compound in an inert base such as gelatin and glycerin or sucrose and acacia.

The compounds may be formulated for parenteral administration by injection, e.g., by bolus injection or continuous infusion. Formulations for injection may be presented in unit dosage form, e.g., in ampules or in multi-dose containers, with an added preservative. The compositions may be suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile pyrogen-free water or other solvents, before use.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 to 0.2M concentration with respect to the active compound. Formulations suitable for transdermal administration may also be delivered by iontophoresis (see, e.g., Pharmaceutical Research 3 (6), 318 (1986)) and typically take the form of an optionally buffered aqueous solution of the active compound.

The pharmaceutical compositions may also be administered by controlled release means and/or delivery devices (see, e.g., in U.S. Pat. Nos. 3,536,809; 3,598,123; 3,630,200; 3,845,770; 3,847,770; 3,916,899; 4,008,719; 4,687,610; 4,769,027; 5,059,595; 5,073,543; 5,120,548; 5,354,566; 5,591,767; 5,639,476; 5,674,533 and 5,733,566).

Desirable blood levels may be maintained by a continuous infusion of the active agent as ascertained by plasma levels. It should be noted that the attending physician would know how to and when to terminate, interrupt or adjust therapy to lower dosage due to toxicity, or bone marrow, liver or kidney dysfunctions. Conversely, the attending physician would also know how to and when to adjust treatment to higher levels if the clinical response is not adequate (precluding toxic side effects).

The efficacy and/or toxicity of the endotheliase inhibitor(s), alone or in combination with the anti-angiogenic agent or pro-angiogenic agent can also be assessed by the methods known in the art (see generally, O'Reilly, *Investigational New Drugs*, 15:5-13 (1997)). For example, the in vitro angiogenesis assays based on target compound's ability to inhibit endothelial cell proliferation, migration, and tube formation in vitro can be used. Alternatively, the in vivo angiogenesis assays such as the chicken chorioallantoic membrane (CAM) assay and the disc angiogenesis assays can be used. Preferably, the established pre-clinical models for the evaluation of angiogenesis inhibitors in vivo such as corneal angiogenesis assays, primate model of ocular angiogenesis, metastasis models, primary tumor growth model and transgenic mouse model of tumor growth can be used.

The active compounds or pharmaceutically acceptable derivatives may be prepared with carriers that protect the compound against rapid elimination from the body, such as time release formulations or coatings.

Kits containing the compositions and/or the combinations with instructions for administration thereof are provided. The kit may further include a needle or syringe, preferably packaged in sterile form, for injecting the complex, and/or a packaged alcohol pad. Instructions are optionally included for administration of the active agent by a clinician or by the patient.

Finally, the compounds or endotheliases or protease domains thereof or compositions containing any of the preceding agents may be packaged as articles of manufacture containing packaging material, a compound or suitable derivative thereof provided herein, which is effective for treatment of a diseases or disorders contemplated herein, within the packaging material, and a label that indicates that the compound or a suitable derivative thereof is for treating the diseases or disorders contemplated herein. The label can optionally include the disorders for which the therapy is warranted.

I. Methods of Treatment

1. Treatment of Undesired Angiogenesis

The compounds and combinations are used for treating or preventing a disease or disorder associated with undesired and/or uncontrolled angiogenesis in a mammal is provided herein. In one embodiment, the method includes administering to a mammal an effective amount of an inhibitor of an endotheliase, whereby the disease or disorder is treated or prevented. In a preferred embodiment, the endotheliase inhibitor used in the treatment or prevention is administered with a pharmaceutically acceptable carrier or excipient. The mammal treated can be a human.

The treatment or prevention method can further include administering an anti-angiogenic treatment or agent or anti-tumor agent simultaneously with, prior to or subsequent to the endotheliase inhibitor, which can be any compound identified that inhibits the activity of an endotheliase, and includes an antibody or a fragment or derivative thereof containing the binding region thereof against the endotheliase, an antisense nucleic acid encoding the endotheliase, and a nucleic acid containing at least a portion of a gene encoding the endotheliase into which a heterologous nucleotide sequence has been inserted such that the heterologous sequence inactivates the biological activity of at least a portion of the gene encoding the endotheliase, in which the portion of the gene encoding the endotheliase flanks the heterologous sequence so as to promote homologous recombination with a genomic gene encoding the endotheliase.

The undesired or aberrant angiogenesis to be treated or prevented is associated with solid neoplasms, vascular malformations and cardiovascular disorders, chronic inflammatory diseases and aberrant wound repairs, circulatory disorders, crest syndromes, dermatological disorders, or ocular disorders. Vascular malformations and cardiovascular disorders to be treated or prevented include angiofibroma, angiolipoma, atherosclerosis, restenosis/reperfusion injury, arteriovenous malformations, hemangiomatosis and vascular adhesions, dyschondroplasia with vascular hamartomas (Fafucci's syndrome), hereditary hemorrhagic telangiectasia (Rendu-Osler-Weber syndrome), or Von Hipple Lindau syndrome; the chronic inflammatory diseases to be treated or prevented are diabetes mellitus, hemophiliac joints, inflammatory bowel disease, nonhealing fractures, periodontitis (rapidly progressing and juvenile), psoriasis, rheumatoid arthritis, venous stasis ulcers, granulations-burns, hypertrophic scars, liver cirrhosis, osteoradionecrosis, postoperative adhesions, pyogenic granuloma, or systemic sclerosis; the circulatory disorder to be treated or prevented is Raynaud's phenomenon; the crest syndromes to be treated or prevented are calcinosis, esophageal dysmotility, sclerodactyly and telangiectasis; the dermatological disorders to be treated or prevented are systemic vasculitis, scleroderma, pyoderma gangrenosum, vasculopathy, venous, arterial ulcers, Sturge-Weber syndrome, Port-wine stains, blue rubber bleb nevus syndrome, Klippel-Trenaunay-Weber syndrome or Osler-Weber-Rendu syndrome; and the ocular disorders to be treated or prevented are blindness caused by ocular neovascular disease, corneal graft neovascularization, macular degeneration in the eye, neovascular glaucoma, trachoma, diabetic retinopathy, myopic degeneration, retinopathy of prematurity, retrolental fibroplasia, or corneal neovascularization.

a. Antisense Treatment

In a specific embodiment, as described hereinabove, endotheliase function is reduced or inhibited by endotheliase antisense nucleic acids, to treat or prevent disease or disorder associated with undesired and/or uncontrolled angiogenesis. The therapeutic or prophylactic use of nucleic acids of at least six nucleotides that are antisense to a gene or cDNA encoding endotheliase or a portion thereof. An endotheliase "antisense" nucleic acid as used herein refers to a nucleic acid capable of hybridizing to a portion of an endotheliase RNA (preferably mRNA) by virtue of some sequence complementarily. The antisense nucleic acid may be complementary to a coding and/or noncoding region of an endotheliase mRNA. Such antisense nucleic acids have utility as therapeutics that reduce or inhibit endotheliase function, and can be used in the treatment or prevention of disorders as described supra.

The endotheliase antisense nucleic acids are of at least six nucleotides and are preferably oligonucleotides (ranging from 6 to about 150 nucleotides, or more preferably 6 to 50 nucleotides). In specific aspects, the oligonucleotide is at least 10 nucleotides, at least 15 nucleotides, at least 100 nucleotides, or at least 125 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., *Proc. Natl. Acad. Sci. U.S.A.* 86:6553-6556 (1989); Lemaitre et al., *Proc. Natl. Acad. Sci. U.S.A.* 84:648-652 (1987); PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., *BioTechniques* 6:958-976 (1988)) or intercalating agents (see, e.g., Zon, *Pharm. Res.* 5:539-549 (1988)).

The endotheliase antisense nucleic acid is preferably an oligonucleotide, more preferably of single-stranded DNA. In a preferred aspect, the oligonucleotide includes a sequence antisense to a portion of human endotheliase. The oligonucleotide may be modified at any position on its structure with substituents generally known in the art.

The endotheliase antisense oligonucleotide may comprise at least one modified base moiety which is selected from the group including, but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide includes at least one modified sugar moiety selected from the group including but not limited to arabinose, 2-fluoroarabinose, xylulose, and hexose. The oligonucleotide can include at least one modified phosphate backbone selected from a phosphorothioate, a phosphorodithioate, a phosphoramidothioate, a phosphoramidate, a phosphordiamidate, a methylphosphonate, an alkyl phosphotriester, and a formacetal or analog thereof.

The oligonucleotide can be an α-anomeric oligonucleotide. An α-anomeric oligonucleotide forms specific double-stranded hybrids with complementary RNA in which the strands run parallel to each other (Gautier et al., *Nucl. Acids Res.* 15:6625-6641 (1987)).

The oligonucleotide may be conjugated to another molecule, e.g., a peptide, hybridization triggered cross-linking agent, transport agent and hybridization-triggered cleavage agent.

The oligonucleotides may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448-7451 (1988)), etc.

In a specific embodiment, the endotheliase antisense oligonucleotide includes catalytic RNA, or a ribozyme (see, e.g., PCT International Publication WO 90/11364, published Oct. 4, 1990; Sarver et al., *Science* 247:1222-1225 (1990)). In another embodiment, the oligonucleotide is a 2'-O-methylribonucleotide (Inoue et al., *Nucl. Acids Res.* 15:6131-6148 (1987)), or a chimeric RNA-DNA analogue (Inoue et al., *FEBS Lett.* 215:327-330 (1987)).

In an alternative embodiment, the endotheliase antisense nucleic acid is produced intracellularly by transcription from an exogenous sequence. For example, a vector can be introduced in vivo such that it is taken up by a cell, within which cell the vector or a portion thereof is transcribed, producing an antisense nucleic acid (RNA). Such a vector would contain a sequence encoding the endotheliase antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the endotheliase antisense RNA can be by any promoter known in the art to act in mammalian, preferably human, cells. Such promoters can be inducible or constitutive. Such promoters include but are not limited to: the SV40 early promoter region (Bernoist and Chambon, *Nature* 290:304-310 (1981)), the promoter contained in the 3' long terminal repeat of Rous sarcoma virus (Yamamoto et al., *Cell* 22:787-797 (1980)), the herpes thymidine kinase promoter (Wagner et al., *Proc. Natl. Acad. Sci. U.S.A.* 78:1441-1445 (1981)), the regulatory sequences of the metallothionein gene (Brinster et al., *Nature* 296:39-42 (1982)), etc.

The antisense nucleic acids include sequence complementary to at least a portion of an RNA transcript of an endotheliase gene, preferably a human endotheliase gene. Absolute complementarily, although preferred, is not required.

The amount of endotheliase antisense nucleic acid that will be effective in the treatment or prevention of disease or disorder associated with undesired and/or uncontrolled angiogenesis will depend on the nature of the disease, and can be determined empirically by standard clinical techniques. Where possible, it is desirable to determine the antisense cytotoxicity in cells in vitro, and then in useful animal model systems prior to testing and use in humans.

2. Treatment of Deficient Angiogenesis

In another specific embodiment, a method for treating or preventing a disease or disorder associated with deficient angiogenesis in a mammal is provided herein by administering to a mammal an effective amount of an endotheliase protein at least partially encoded by a nucleic acid that hybridizes to a nucleic acid having the nucleotide sequence set forth in the SEQ. ID NO:1, a domain, a derivative or analog of the protein that is active in promoting angiogenesis, a nucleic acid encoding the protein, and a nucleic acid encoding a domain, a derivative or analog of the protein that is active in promoting angiogenesis, whereby the disease or disorder is treated or prevented.

In a preferred embodiment, the endotheliase protein, a domain, a derivative or analog of the protein, a nucleic acid encoding the protein, and a nucleic acid encoding a domain, a derivative or analog of the protein is administered with a pharmaceutically acceptable carrier or excipient.

In yet another preferred embodiment, the mammal to be treated is a human. The treatment or prevention methods can further include administering an pro-angiogenic treatment or agent. In yet another preferred embodiment, the treatment is used to promote physiological angiogenesis, particularly angiogenesis involved in normal placental, embryonic, fetal and post-natal development and growth, physiologically cyclical development in the ovarian follicle, corpus luteum and post-menstrual endometrium or wound healing.

The pro-angiogenic agent used in the treatment can be, for example, a basic fibroblast growth factor such as bFGF and FGF-2, a vascular endothelial growth factor/vascular permeability factor such as VEGF/VPF and vasculotropin, a platelet-derived endothelial cell growth factor such as PD-EDGF and thymidine phosphorylase, a transforming growth factor-beta (TGF-β), or angiopoietin-1 (Ang-1).

Gene Therapy

In an exemplary embodiment, nucleic acids that include a sequence of nucleotides encoding an endotheliase protein or functional domains or derivative thereof, are administered to promote endotheliase protein function, by way of gene therapy. Gene therapy refers to therapy performed by the administration of a nucleic acid to a subject. In this embodiment, the nucleic acid produces its encoded protein that mediates a therapeutic effect by promoting endotheliase protein function. Any of the methods for gene therapy available in the art can be used (see, Goldspiel et al., *Clinical Pharmacy* 12:488-505 (1993); Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIBTECH* 11(5):155-215 (1993). For example, one therapeutic composition for gene therapy includes an endotheliase-encoding nucleic acid that is part of an expression vector that expresses an endotheliase protein or domain, fragment or chimeric protein thereof in a suitable host. In particular, such a nucleic acid has a promoter operably linked to the endotheliase coding region, the promoter being inducible or constitutive, and, optionally, tissue-specific. In another particular embodiment, a nucleic acid molecule is used in which the endotheliase coding sequences and any other desired sequences are flanked by regions that promote homologous recombination at a desired site in the genome, thus providing for intrachromosomal expression of the endotheliase nucleic acid (Koller and Smithies, *Proc. Natl. Acad. Sci. USA* 86:8932-8935 (1989); Zijlstra et al., *Nature* 342:435-438 (1989)).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, *J. Biol. Chem.* 262:4429-4432 (1987)) (which can be used to target cell types specifically expressing the receptors), etc. In another embodiment, a nucleic acid-ligand complex can be formed in which the ligand is a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, *Proc. Natl. Acad. Sci. USA* 86:8932-8935 (1989); Zijlstra et al., *Nature* 342:435-438 (1989)).

In a specific embodiment, a viral vector that contains the endotheliase nucleic acid is used. For example, a retroviral vector can be used (see Miller et al., *Meth. Enzymol.* 217:581-599 (1993)). These retroviral vectors have been modified to delete retroviral sequences that are not necessary for packaging of the viral genome and integration into host cell DNA. The endotheliase nucleic acid to be used in gene therapy is cloned into the vector, which facilitates delivery of the gene into a patient. More detail about retroviral vectors can be found in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); and Mastrangeli et al., *J. Clin. Invest.* 91:225-234 (1993).

Adeno-associated virus (AAV) has also been proposed for use in gene therapy (Walsh et al., *Proc. Soc. Exp. Biol. Med.* 204:289-300 (1993).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, *Meth. Enzymol.* 217:599-618 (1993); Cohen et al., *Meth. Enzymol.* 217:618-644 (1993); Cline, *Pharmac. Ther.* 29:69-92 (1985)) and may be used, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient. In an embodiment in which recombinant cells are used in gene therapy, an endotheliase nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment. Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, *Cell* 71:973-985 (1992)).

Epithelial stem cells (ESCs) or keratinocytes can be obtained from tissues such as the skin and the lining of the gut by known procedures (Rheinwald, *Meth. Cell Bio.* 21A:229 (1980)). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, *Meth. Cell Bio.* 21A:229 (1980); Pittelkow and Scott, *Mayo Clinic Proc.* 61:771 (1986)). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment, human bone marrow cells can be obtained from the posterior iliac crest by needle aspiration (see, e.g., Kodo et al., *J. Clin. Invest.* 73:1377-1384 (1984)). In a preferred embodiment, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., *J. Cell Physiol.* 91:335 (1977) or Witlock-Witte culture techniques (Witlock and Witte, *Proc. Natl. Acad. Sci. USA* 79:3608-3612 (1982)).

In a specific embodiment, the nucleic acid to be introduced for purposes of gene therapy includes an inducible promoter operably linked to the coding region, such that expression of the nucleic acid is controllable by controlling the presence or absence of the appropriate inducer of transcription.

J. Animal Models

Transgenic animal models are provided herein. In one embodiment, animal models for diseases and disorders involving deficient angiogenesis are provided. Such an animal can be initially produced by promoting homologous recombination between an endotheliase gene in its chromosome and an exogenous endotheliase gene that has been rendered biologically inactive (preferably by insertion of a heterologous sequence, e.g., an antibiotic resistance gene). In a preferred aspect, this homologous recombination is carried out by transforming embryo-derived stem (ES) cells with a vector containing the insertionally inactivated endotheliase gene, such that homologous recombination occurs, followed by injecting the ES cells into a blastocyst, and implanting the blastocyst into a foster mother, followed by the birth of the chimeric animal ("knockout animal") in which an endotheliase gene has been inactivated (see Capecchi, *Science* 244:1288-1292 (1989)). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing diseases or disorders involving deficient angiogenesis and thus can have use as animal models of such diseases and disorders, e.g., to screen for or test molecules for the ability to treat or prevent such diseases or disorders.

In a separate embodiment, animal models for diseases and disorders involving uncontrolled and/or undesired angiogenesis are provided. Such an animal can be initially produced by promoting homologous recombination between an endotheliase gene in its chromosome and an exogenous endotheliase gene that would be over-expressed or mis-expressed (preferably by expression under a strong promoter). In a preferred aspect, this homologous recombination is carried out by transforming embryo-derived stem (ES) cells with a vector containing the over-expressed or mis-expressed endotheliase gene, such that homologous recombination occurs, followed by injecting the ES cells into a blastocyst, and implanting the blastocyst into a foster mother, followed by the birth of the chimeric animal in which an endotheliase gene has been over-expressed or mis-expressed (see Capecchi, *Science* 244:1288-1292 (1989)). The chimeric animal can be bred to produce additional animals with over-expressed or mis-expressed endotheliase. Such animals can be mice, hamsters, sheep, pigs, cattle, etc., and are preferably non-human mammals. In a specific embodiment, a mouse with over-expressed or mis-expressed endotheliase is produced.

Such animals are expected to develop or be predisposed to developing diseases or disorders involving diseases or disorders involving uncontrolled and/or undesired angiogenesis and thus can have use as animal models of such diseases and disorders, e.g., to screen for or test molecules for the ability to inhibit function of endotheliase genes and proteins and thus treat or prevent such diseases or disorders.

The following examples are included for illustrative purposes only and are not intended to limit the scope of the invention.

EXAMPLE 1

Cloning and Expression of Endotheliase-1
Cell Type and Growth of Cells

Human umbilical vein endothelial cells (HUVEC P145, hereafter called HUVEC) were purchased from Clonetics (catalog number CC-2519; BioWhittaker Inc., Walkersville, Md.). The cells were cultured at 37° C., 5% $CO_2$ in endothelial growth medium (EGM; catalog number CC-3124; Clonetics) supplemented with u0.4% bovine brain extract with heparin, 2% fetal bovine serum, 1 µg/mL hydrocortisone, 10 ng/mL epidermal growth factor, 50 ng/mL amphotericin-B and 50 µg/mL gentamicin sulfate. All subsequent cell manipulations were carried out according to the manufacturer's instructions. HUVEC were allowed to grow to about 90% confluent, then briefly washed with 1× phosphate buffered saline.

Isolation of Total RNA, and Purification and Enrichment of PolyA+RNA

HUVEC were lysed in Trizol reagent (catalog number 15596; Life Technologies, Rockville, Md.) and total RNA was isolated according to the manufacturer's protocol. The concentration of total RNA was estimated from absorbance reading at 260 nm. PolyA+RNAs were purified and enriched using oligo-dT beads (catalog number 70061; Oligotex, Qiagen, Chatsworth, Calif.).

Reverse-Transcription and Polymerase Chain Reaction (PCR)

HUVEC polyA+RNAs were converted to single-stranded cDNA (sscDNA) by reverse transcription using ProSTAR first-strand RT-PCR kit (catalog No. 200420; Stratagene, La Jolla, Calif.) and SuperScript II RNase H-reverse transcriptase (catalog number 18064-022; Life Technologies). An aliquot of HUVEC sscDNA (4 µL) was subjected to PCR using 2 µM each of the sense and anti-sense degenerate oligonucleotide primers and Taq polymerase. The sequence of the sense primer was 5'-TGGRT(I)VT(I)WS(I)GC(I)RC(I)CAYTG-3' SEQ ID NO. 9 and that of the anti-sense was 5'-(I)GG(I)CC(I)CC(I)SWRTC(I)CCYT(I)RCA(I)GHRTC-3' SEQ ID No. 10, where R=A,G; V=G,A,C; W=A,T; S=G,C; Y=C,T; H=A,T,C. The primer sequences correspond to two highly conserved regions in all serine proteases and amplify PCR products ranging from 400 to 500 base pairs.

Clone Screening and Sequencing

The PCR products were separated on a 2% agarose gel and purified using a gel extraction kit (catalog number 28706; QIAquick gel extraction kit; Qiagen). The purified DNA fragments were ligated into TA vectors (catalog number K4500-01; TOPO-TA cloning kit, Invitrogen, Carlsbad, Calif.). After transformation into *E. coli* cells, plasmid DNAs were isolated and analyzed by digestion with EcoRI restriction enzyme. Clones that had insert DNAs were further characterized by sequencing using a fluorescent dye-based DNA sequencing method (catalog number 4303149; BigDye terminator cycle sequencing kit with AmpliTaq DNA polymerase; Perkin Elmer, Lincoln, Calif.). A total of 170 clones were sequenced and analyzed. All sequences were analyzed by a multiple nucleotide sequence alignment algorithm (blastn) to identify identical or closely related cDNA clones deposited in GenBank (NCBI, Bethesda, Md.). Those that did not show significant homology were further analyzed using blastx, which compares the six-frame conceptual translation products of a nucleotide sequence (both strands) against a protein sequence database (SwissProt). Two clones yielded a cDNA fragment that encodes a serine protease. One of these clones (H117) encodes the protease domain of an endothelial serine protease, the protein herein designated endotheliase 1.

Gene Expression Profile of the Endothelial Serine Protease Endotheliase 1

To obtain information regarding the tissue distribution of endotheliase 1, the DNA insert of clone H117 was used to probe an RNA blot composed of 76 different human tissues (catalog number 7775-1; human multiple tissue expression (MTE) array; CLONTECH, Palo Alto, Calif.). Significant expression was observed in the esophagus, with minor expression levels in the stomach, salivary gland, pancreas, prostate, bladder, trachea and uterus. Northern analysis using RNA blots (catalog numbers 7765-1 & 7782-1; human muscle and digestive system multiple tissue northern (MTN) blots; CLONTECH) confirmed that the expression was restricted to the esophagus. Two transcripts (approximately 1.7 and 2 kb) were detected in the esophagus.

Presence of Endotheliase 1 in Human Umbilical Vein Endothelial Cells

Single-stranded cDNA clones were reverse-transcribed from polyA+RNAs isolated and purified from human umbilical vein endothelial cells (HUVEC) using Superscript II (Life Technologies, Rockville, Md.) and oligo-dT primer. Endotheliase 1-specific primers (sense primer: 5'-CCTGCCAGATGGACTGCTTCCTTTG-3' (SEQ ID No. 7) antisense primer: 5'-GGCATGCATCTGTTTTTCCTTCTAAGG-3' (SEQ ID NO. 8) were used to amplify a 390-bp fragment from the sscDNAs of HUVEC. To prevent non-specific amplification of other serine proteases, the primers were designed so that they hybridize outside of the highly conserved sequences common to all trypsin-like serine proteases. RT-PCR of endotheliase 1 transcripts from HUVEC cells showed a ~400-bp DNA fragment plus another smaller, non-specific band after separation on a 2% agarose gel. The gel was blotted onto a positively charged nylon membrane and hybridized at 60° C. with an endotheliase 1 cDNA fragment isolated from the H117 clone using ExpressHyb™ hybridization solution (CLONTECH). After washing at high stringency (68° C. in 0.1×SSC; 0.1% SDS), a strong positive signal was observed on the ~400-bp fragment only, indicating that this band corresponds to the endotheliase 1 cDNA, and that HUVEC cells express endotheliase 1.

5'- and 3'-Rapid Amplification of cDNA Ends (RACE)

To obtain cDNA that encodes the entire protease domain of endotheliase 1,5'- and 3'-RACE reactions were performed. Since the presence of the transcript was detected in the prostate, a human prostate Marathon-Ready cDNA (catalog # 7418-1; Clontech) was used to isolate the 5' and 3' ends of the cDNA encoding endotheliase 1. Marathon-Ready cDNAs are specifically made for RACE reactions. Two gene specific primers were used: 5'-GGCATGCATCTGTTTTTC-CTTCTAAGG-3' (SEQ ID No. 8) for 5'-RACE reaction and 5'-CCTGCCAGATGGACTGCTTCCTTTG-3' (SEQ ID No. 7) for 3'-RACE reaction.

Two fragments, approximately 1.2 kbp and 1.4 kbp, were isolated that corresponded to the missing 5' and 3' end sequences. These fragments were confirmed by Southern analysis using the internal cDNA fragment as probe and by DNA sequence analysis.

Sequence Analysis

All derived DNA and protein sequences were analyzed using MacVector (version 6.5; Oxford Molecular Ltd., Madison, Wis.). The cDNA encoding the protease domain of endotheliase1 is composed of 696 base pairs (SEQ ID No. 1) which translate to a 232-amino acid protein sequence (SEQ ID No. 2).

The cDNA encoding this protein was cloned into a derivative of the *Pichia pastoris* vector pPIC9K (available from Invitrogen; see SEQ ID NO. 21). Plasmid pPIC9k features include the 5' AOX1 promoter fragment at 1-948; 5' AOX1 primer site at 855-875; alpha-factor secretion signal(s) at 949-1218; alpha-factor primer site at 1152-1172; multiple cloning site at 1192-1241; 3' AOX1 primer site at 1327-1347; 3' AOX1 transcription termination region at 1253-1586; HIS4 ORF at 4514-1980; kanamycin resistance gene at 5743-4928; 3' AOX1 fragment at 6122-6879; ColE1 origin at 7961-7288; and the ampicillin resistance gene at 8966-8106. The plasmid used herein is derived from pPIC9K by eliminating the XhoI site in the kanamycin resistance gene and the resulting vector is herein designated pPIC9KX.

For expression in *Pichia pastoris*, the cDNA encoding the protease domain was amplified using the same pair of gene-specific primers, except that restriction sites were introduced at the 5' ends of each primer to facilitate cloning into the *Pichia* vector, pPIC9KX. The primers were as follows:

forward (SEQ ID No. 23) 5'-TCTCTCGAGAAAA-GAATCGTTGGTGGGACAGAAGTAGAAGAG-3'; and

Reverse (SEQ ID NO. 24) 5'-ATTCGCGGCCGCTTA-GATACCAGTTTTTGAAGTAATCCA-3'.

EXAMPLE 2

Cloning and Expression of Endotheliase 2

Identification of Endotheliase 2

The UniGene (http://www.ncbi.nim.nih.gov/UniGene) tool for data mining at the National Center for Biotechnology Information was searched for a serine protease sequence cluster. A UniGene cluster is a non-redundant set of sequences that represents a unique human, mouse, or rat gene. The database includes well-characterized genes and expressed sequence tag (EST) sequences, including information regarding tissue distribution and chromosomal map location.

A UniGene cluster (Hs.245327/Hs.266308) was identified that had ESTs which were weakly similar to the human serine protease, hepsin (accession number P05981). This cluster contains 12 EST sequences that were expressed in the ovary, placenta, uterus, breast and colon. One EST sequence (AI909842) derived from human breast carcinoma was used to isolate the full-length cDNA encoding this novel serine protease (hereafter referred to as endotheliase 2). The sequence contained in AI909842 did not show 100% identity to any known serine protease sequence deposited in GenBank. Using blastx to identify homologous protein sequences deposited in the protein database, the closest matches were found to be hepsin (53 to 55%), human TMPRSS2 (47%), human MTSP2 (47%), and human plasma kallikrein B1 precursor (47%). A search of the unfinished human genome database (High Throughput Genomic Sequences (HTGS)) using blastn indicated that the gene encoding endotheliase 2 is located in chromosome 11 (11 q23).

5'- and 3'-Rapid Amplification of cDNA Ends (RACE)

To obtain a full-length cDNA clone encoding endotheliase 2,5'- and 3'-RACE reactions were performed. The Marathon-Ready cDNA library from human mammary carcinoma (GI-101; CLONTECH; catalog number 7493-1) was used to isolate the 5' and 3' ends of the cDNA encoding endotheliase 2. Marathon-Ready cDNAs are specifically made for RACE reactions. Two gene specific primers were used: 5'-GGAG-GCAAGCAGGGTGGATGTGAGCGGAC-3' (SEQ ID NO. 11) for 5'-RACE reaction and 5'-CGGATCGTGG-GAGGGGCGCTGGCCTC-3' (SEQ ID NO. 12) for 3'-RACE reaction. A ~1.5 kbp cDNA fragment was obtained from the 5'-RACE reaction. The initial 3'-RACE reaction, however, did not produce any fragment. A nested PCR was used on the initial 3'-RACE reaction products to obtain the rest of the 3' end of endotheliase 2. The nested 3' gene-specific primer used was 5'-CAAGTGAGTCTGCACT-TCGGCACCACC-3' SEQ ID NO. 13 and produced a ~1.2 kbp cDNA fragment. The fragments were subcloned into pCR2.1-TOPO TA cloning vector (Invitrogen, Carlsbad, Calif.). The resulting clones were analyzed by Southern analysis using the cDNA insert of EST clone AI909842 as a probe and by DNA sequence analysis.

Domain Organization of Endotheliase 2

Sequence analysis of the translated endotheliase 2 coding sequence indicated that endotheliase 2 is a type-II membrane-type serine protease. It has a transmembrane domain at the N-terminus, followed by a single low density lipoprotein-A receptor domain and a single scavenger-receptor cysteine-rich domain. The C-terminus contains the trypsin-like serine protease domain characterized by the presence of the catalytic triad residues (histidine, aspartate and serine) in 3 highly-conserved regions of the catalytic domain. In addition, three repetitive sequences composed of ASPAGT- PPGRASP (SEQ ID NO. 14) are found just before the transmembrane domain, and represent a sequence motif for N-myristoylation modification.

PCR Amplification of cDNA Encoding Full-Length Protease Domain of Endotheliase 2

To obtain the cDNA fragment encoding the protease domain of endotheliase 2, an end-to-end PCR amplification using gene-specific primers and the Marathon-Ready cDNA library from human mammary carcinoma was used. The two primers used were: 5'-CGGATCGTGGGAGGGGCGCTG-GCCTCG-3' (SEQ ID NO. 15) for the 5' end, and 5'-CAG-CAGGCCAGCTGGTTAGGATTTTATGAATCGCAC-3' (SEQ ID NO. 16) for the 3' end. The 5' primer contained the sequence that encodes the start of the endotheliase 2 protease domain (RIVGGALAS SEQ ID NO. 17). The 3' primer corresponds to the sequence flanking the stop codon (underlined). A ~730-bp fragment was amplified, subcloned into pCR2.1-TOPO TA cloning vector and sequenced.

For expression in *Pichia pastoris*, the cDNA encoding the protease domain was amplified using the same pair of gene-specific primers, except that restriction sites (XhoI site and NotI site for 5' and 3' primers, respectively) were introduced at the 5' ends of each primer to facilitate cloning into the *Pichia* vector, pPIC9KX. The primers were as follows:

forward (SEQ ID NO. 25) 5'-TCTCTCGAGAAAA-GAATCGTGGGAGGGGCGCTGGCCTCG-3' reverse (SEQ ID No. 26) 5'-ATAGCGGCCGCTGGTTAG-GATTTTATGAATCGCACCTCGC-3'.

Gene Expression Profile and Transcript Size of Endotheliase 2 in Normal and Tumor Tissues To obtain information regarding the gene expression profile of the endotheliase 2 transcript, the cDNA insert of EST clone AI909842 was used to probe an RNA dot blot composed of 76 different human tissues (human multiple tissue expression (MTE) array; catalog number 7775-1; CLONTECH, Palo Alto, Calif.) and a human tissue northern blot (human 12-lane multiple tissue northern (MTN) blot; catalog number 7780-1; CLONTECH). The RNA dot blot showed strong signals in placenta, pancreas, thyroid gland, liver and lung. Moderate signals were observed in mammary gland, salivary gland, kidney, trachea, esophagus, appendix, heart and fetal lung. Weak signals were seen in several other tissues. Endotheliase 2 is also expressed in several tumor cell lines including leukemia K-562>HeLa S3=Burkitt's lymphomas (Raji and Daudi)=colorectal adenocarcinoma (SW480)=lung carcinoma (A549)=leukemia MOLT-4=leukemia HL-60.

Northern analysis detected several transcripts in the tissues tested with strong signals observed in the heart, skeletal muscle, kidney, liver and placenta. The predominant transcript had a size of ~3 kb, while other transcripts were approximately 2.8 kb, 1.5 kb and 1 kb.

PCR amplification of the endotheliase 2 transcript from cDNA libraries made from several human primary tumors xenografted in nude mice (human tumor multiple tissue cDNA panel, catalog number K1522-1, CLONTECH) was performed using endotheliase 2-specific primers. The endotheliase 2 transcript was detected in breast carcinoma (GI-101), lung carcinomas (LX-1>GI-117), colon adenocarcinomas (GI-112>CX-1), pancreatic adenocarcinoma (GI-103), and ovarian carcinoma (GI-102). The endotheliase 2 transcript was also detected in LNCaP and PC-3 prostate cancer cell lines as well as in HT-1080 human fibrosarcoma cell line.

Presence of Endotheliase 2 in Endothelial Cells

Single-stranded cDNAs were reverse-transcribed from polyA+RNAs isolated and purified from human umbilical vein endothelial cells (HUVEC) and human lung microvascular endothelial cells (HMVEC-L) using Superscript II (Life Technologies, Rockville, Md.) and oligo-dT primer. endotheliase 2-specific primers (sense primer: 5'-TCCAG-GAAAGCCTCCACAGGTC-3' SEQ ID NO. 18; anti-sense primer: 5'-GGAGGCAAGCAGGGTGGATGTGAGCG-GAC-3' SEQ ID NO. 19) were used to amplify a 422-bp fragment from the sscDNAs of endothelial cells. This 422-bp fragment spans the scavenger receptor cysteine-rich domain and the serine protease domain. RT-PCR of endotheliase 2 transcripts from HUVEC and HMVEC-L cells showed a ~420-bp DNA fragment plus other non-specific bands after separation on a 2% agarose gel. The gel was blotted onto a positively charged nylon membrane and hybridized at 60° C. with an endotheliase 2 cDNA originally isolated from human mammary gland carcinoma using ExpressHyb™ hybridization solution (CLONTECH). After washing at high stringency (68° C. in 0.1×SSC; 0.1% SDS), a strong positive signal was observed on the ~420-bp fragment only, indicating that this DNA fragment corresponds to the endotheliase 2 cDNA, and that HUVEC and HMVEC-L cells express endotheliase 2.

Presence of Another Form of Endotheliase 2 in Placenta and LNCaP Cells.

Since multiple endotheliase 2 mRNAs were present in placenta, another 3'-RACE reaction was performed using a endotheliase 2-specific primer (5'-TTCCTCCGGGAGGTG-CAGGTCAATC-3' SEQ ID NO. 20). Several products were observed, but only two fragments (~2.2 kbp and ~1 kbp) showed strong hybridization with the endotheliase 2 probe. Upon subcloning and sequence analysis, the longer fragment showed sequence identity to the endotheliase 2 cDNA initially isolated from human mammary carcinoma. The sequence of the shorter fragment showed sequence identity to that of the human mammary carcinoma-derived endotheliase 2 in all but the last 24 bp of the coding region. Replacing these 24 bp was a 402-bp fragment which extended the coding region by an additional 134 amino acids. Interestingly, another transmembrane domain is found within this additional protein sequence. Using a set of endotheliase 2 primers (one primer common to both forms and the other one was specific to each form), the human mammary carcinoma and LNCaP cDNA libraries were screened for the presence of either or both forms. After subcloning and sequence analysis, the results showed that mammary breast carcinoma only expressed the mRNA encoding the shorter protein (endotheliase 2-S), while LNCaP only expressed the longer form (endotheliase 2-L).

Sequence Analysis

Endotheliase 2-encoding DNA and the encoded protein were analyzed using MacVector (version 6.5; Oxford Molecular Ltd., Madison, Wis.). The ORF of endotheliase 2-S is composed of 1,689 bp which translate to a 562-amino acid protein, while the ORF of endotheliase 2-L is composed of 2,067 bp which translate to a 688-amino acid protein. The cDNA encoding the protease domain in endotheliase 2-S is composed of 729 bp which translate to a 242-amino acid protein sequence, while that of endotheliase 2-L is composed of 1,107 bp which translate to a 368-amino acid protein sequence. The nucleic acid sequences and the protein sequences of endotheliase 2-S and endotheliase 2-L are set forth in SEQ ID Nos. 3-6. SEQ ID NO. 3 sets forth the nucleic acid sequence of endotheliase 2-S; SEQ ID NO. 4 sets forth the endotheliase 2-S encoded protein; SEQ ID NO.

5 sets forth the nucleic acid sequence of Endotheliase 2-L; and SEQ ID NO. 6 sets forth the Endotheliase 2-L encoded protein.

EXAMPLE 3

High Throughput Assay for Identification of Candidate Angiogenesis Modulators

Assay for Identifying Inhibitors of Endotheliase 1

The ability of test compounds to act as inhibitors of Endotheliase-1 (ET1) catalytic activity was assessed in an amidolytic assay. The inhibitor-induced inhibition of amidolytic activity by the recombinant (rET1) expressed in *Pichia*, as measured by IC50 values was assessed.

The assay buffer was HBSA (10 mM Hepes, 150 mM sodium chloride, pH 7.4, 0.1% bovine serum albumin). All reagents were from Sigma Chemical Co. (St. Louis, Mo.), unless otherwise indicated. Two IC50 assays at 30-minute (a 30-minute preincubation of test compound and enzyme) and at 0-minutes (no preincubation of test compound and enzyme) were conducted. For the IC50 assay at 30-minute, the following reagents were combined in appropriate wells of a Corning microtiter plate: 50 microliters of HBSA, 50 microliters of the test compound, diluted (covering a broad concentration range) in HBSA (or HBSA alone for uninhibited velocity measurement), and 50 microliters of the rET-1 (Corvas International) diluted in buffer, yielding a final enzyme concentration of 250 pM. Following a 30-minute incubation at ambient temperature, the assay was initiated by the addition of 50 microliters of the substrate Spectrozyme tPA (Methylsulfonyl-D-cyclohexyltyrosyl-L-glycyl-L-arginine-p-nitroaniline acetate, obtained from American Diagnostica, Inc. (Greenwich, Conn.) and reconstituted in deionized water, followed by dilution in HBSA prior to the assay) were added to the wells, yielding a final volume of 200 microliters and a final substrate concentration of 300 µM (about 1.5-times Km).

For the IC50 assay at 0-minute, the same reagents were combined: 50 microliters of HBSA, 50 microliters of the test compound, diluted (covering the identical concentration range) in HBSA (or HBSA alone for uninhibited velocity measurement), and 50 microliters of the substrate Spectrozyme tPA. The assay was initiated by the addition of 50 microliters of rET-1. The final concentrations of all components were identical in both IC50 assays (at 30- and 0-minute incubations).

The initial velocity of chromogenic substrate hydrolysis was measured in both assays by the change of absorbance at 405 nM using a Thermo Max¿ Kinetic Microplate Reader (Molecular Devices) over a 5 minute period, in which less than 5% of the added substrate was used. The concentration of added inhibitor, which caused a 50% decrease in the initial rate of hydrolysis was defined as the respective IC50 value in each of the two assays (30- and 0-minute).

Assay for Identifying Inhibitors of Endotheliase 2

Test compounds for inhibition of the protease activity of the protease domain of endotheliase-2 was assayed in Costar 96 well tissue culture plates (Corning N.Y.). Approximately 2-3 nM endotheliase 2 was mixed with varying concentrations of inhibitor in 29.2 mM Tris, pH 8.4, 29.2 mM imidazole, 217 mM NaCl (100 mL final volume), and allowed to incubate at room temperature for 30 minutes. 400 mM substrate S 2765 (DiaPharma, Westchester, Ohio) was added, and the reaction was monitored in a SpectraMAX Plus microplate reader (Molecular Devices, Sunnyvale Calif.) by following the change in absorbance at 405 nm for 1 hour at 37° C.

Since modifications will be apparent to those of skill in this art, it is intended that this invention be limited only by the scope of the appended claims.

What is claimed is:

1. A substantially purified protein, consisting of a protease domain of an endotheliase protein that has catalytic activity, wherein:

the protease domain of the endotheliase is selected from the group consisting of:

a) a polypeptide consisting of the sequence of amino acid residues set forth as amino acids 320-562 of SEQ ID No. 4;

b) a polypeptide consisting of the sequence of amino acid residues set forth as amino acids 320-688 of SEQ ID No. 6; and c) a protease domain of an endotheliase protein consisting of a sequence of amino acid residues that has at least 95% sequence identity to the sequence of amino acids set forth as amino acid residues 320-562 in SEQ IN No. 4 or amino acid residues set forth as amino acid residues 320-688 of SEQ ID No.6.

2. An isolated substantially purified endotheliase 1 protease domain, consisting of the sequence of amino acid residues as set forth in SEQ ID No. 2 or the sequence of amino acid residues set forth as residues 190-422 of SEQ ID No. 27, wherein the isolated purified endotheliase 1 protease domain has protease activity.

3. A substantially purified protein, comprising an endotheliase protein, wherein the endotheliase protein is an endotheliase 2 that comprises the sequence of amino acid residues set forth in SEQ ID No. 4 or 6.

4. The protein of claim 1 that is an endotheliase 2-L.

5. The protein of claim 1 that is an endotheliase 2-S.

6. A substantially purified endotheliase protein, comprising:
the sequence of amino acids set forth in SEQ ID No. 4 or 6; or
a sequence of amino acid residues that has at least 95% sequence identity to the sequence of amino acids set forth as SEQ ID No. 4 or 6, wherein the endotheliase protein is catalytically active.

7. A protein of claim 6 that specifically binds to an antibody that specifically binds to a protease domain of a protein comprising the sequence of amino acids set forth in SEQ ID No. 4 or 6.

8. A kit, comprising a protein of claim 1 and reagents for diagnostic, therapeutic or drug screening.

9. A kit, comprising a protein of claim 6 and reagents for diagnostic, therapeutic or drug screening.

10. A conjugate, comprising:
a) a protein of claim 1, and
b) a targeting agent linked to the protein directly or via a linker;
wherein the conjugate has serine protease activity.

11. The conjugate of claim 10, wherein the targeting agent permits
i) affinity isolation or purification of the conjugate;
ii) attachment of the conjugate to a surface;
iii) detection of the conjugate; or
iv) targeted delivery to a selected tissue or cell.

12. A conjugate, comprising an endotheliase of claim 6 and a targeting agent linked to the protein directly or via a linker, wherein the conjugate has serine protease activity.

13. A solid support, comprising two or more proteins of claim 1 immobilized thereon either directly or via a linker.

14. A solid support, comprising two or more proteins of claim 3 immobilized thereon either directly or via a linker.

15. The support of claim 13, wherein the proteins comprise an array.

16. The support of claim 14, wherein the proteins comprise an array.

17. A substantially purified endotheliase 2 that is encoded by SEQ ID No. 3 or SEQ ID No. 5.

18. A substantially purified endotheliase 2, comprising the sequence of amino acids set forth in SEQ ID No. 6 or consisting of amino acids 320-688 of SEQ ID No. 6.

19. A substantially purified endotheliase 2, comprising the sequence of amino acids set forth in SEQ ID No. 4 or consisting of amino acids 320-562 of SEQ ID No. 4.

20. A substantially purified endotheliase that has at least about 97% sequence identity with a protein that comprises the sequence of amino acids set forth in SEQ ID No. 4 or 6, wherein the substantially purified endotheliase comprises a catalytic triad.

21. A conjugate, comprising:
a) an endotheliase protein of claim 20, and
b) a targeting agent linked to the protein directly or via a linker;
wherein the conjugate has serine protease activity.

22. An endotheliase protein, wherein the protease domain comprises the sequence of amino acids set forth in amino acids 321-562 of SEQ ID No. 4.

23. A substantially purified isolated polypeptide, consisting of an endotheliase protease domain that has at least 95% sequence identity with the sequence of amino acids set forth in SEQ ID No. 2 or amino acids 190-422 of SEQ ID No. 27 or a contiguous portion thereof that exhibits protease activity.

24. The conjugate of claim 21, wherein the targeting agent permits
i) affinity isolation or purification of the conjugate;
ii) attachment of the conjugate to a surface;
iii) detection of the conjugate; or
iv) targeted delivery to a selected tissue or cell.

25. The conjugate of claim 12, wherein the targeting agent permits
i) affinity isolation or purification of the conjugate;
ii) attachment of the conjugate to a surface;
iii) detection of the conjugate; or
iv) targeted delivery to a selected tissue or cell.

26. A conjugate, comprising:
a) a polypeptide of claim 23, and
b) a targeting agent linked to the protein directly or via a linker;
wherein the conjugate has serine protease activity.

27. The conjugate of claim 26, wherein the targeting agent permits
i) affinity isolation or purification of the conjugate;
ii) attachment of the conjugate to a surface;
iii) detection of the conjugate; or
iv) targeted delivery to a selected tissue or cell.

28. A kit, comprising a polypeptide of claim 23 and reagents for diagnostic, therapeutic or drug screening.

29. A solid support, comprising two or more polypeptides of claim 23 immobilized thereon either directly or via a linker.

30. A substantially purified protein, comprising the sequence of amino acid residues set forth in SEQ ID NO. 4 or 6.

31. A substantially purified protein of claim 30, consisting of the sequence of amino acid residues set forth in SEQ ID NO. 4 or 6.

32. A substantially purified protein, comprising the sequence of amino acid residues set forth in SEQ ID NO. 4.

* * * * *

UNITED STATES PATENT AND TRADEMARK OFFICE
CERTIFICATE OF CORRECTION

| | |
|---|---|
| PATENT NO. | : 7,276,364 B1 |
| APPLICATION NO. | : 09/717473 |
| DATED | : October 2, 2007 |
| INVENTOR(S) | : Edwin Madison and Edgar Ong |

It is certified that error appears in the above-identified patent and that said Letters Patent is hereby corrected as shown below:

ON THE TITLE PAGE:
In Item [56] References Cited, in OTHER PUBLICATIONS:
    in Berger et al., please replace "(P/12)" with --(PI12)--
    in the first Coombs et al., please replace "24074-24074" with --24074-24079--
    in the second Morgan et al., please insert --(1989)-- between "252" and the last period
    in Wallrapp et al., please replace "(TMPRSSE)" with --(TMPRSS3)--
    in Yahagi et al., please insert --(1996)-- between "812" and the last period
    in Zijlstra et al., please replace "$\beta_3$" with --$\beta_2$--
    in Matthews et al., please replace "*Sciene*" with --*Science*--
    please insert the following omitted reference:
      --GenBank Database Accession No. ABS74430--
    please insert the following omitted reference:
      --Tramontano et al., "Catalytic Antibodies", *Science* 234:1566-1570 (1986).--

UNITED STATES PATENT AND TRADEMARK OFFICE
CERTIFICATE OF CORRECTION

PATENT NO.         : 7,276,364 B1
APPLICATION NO. : 09/717473
DATED                : October 2, 2007
INVENTOR(S)      : Edwin Madison and Edgar Ong It is certified that error appears in the above-identified patent and that said Letters Patent is hereby corrected as shown below:

Please replace Claim 1 with the following amended claim:

1. A substantially purified protein, consisting of a protease domain of an endotheliase protein that has catalytic activity, wherein:
        the protease domain of the endotheliase is selected from the group consisting of:
        a) a polypeptide consisting of the sequence of amino acid residues set forth as amino acids 320-562 of SEQ ID No. 4;
        b) a polypeptide consisting of the sequence of amino acid residues set forth as amino acids 320-688 of SEQ ID No. 6; and
        c) a protease domain of an endotheliase protein consisting of a sequence of amino acid residues that has at least 95% sequence identity to the sequence of amino acids set forth as amino acid residues 320-562 in SEQ ID No. 4 or amino acid residues set forth as amino acid residues 320-688 of SEQ ID No. 6.

Signed and Sealed this

Nineteenth Day of August, 2008

JON W. DUDAS
*Director of the United States Patent and Trademark Office*